(12) United States Patent
Shenoy et al.

(10) Patent No.: US 7,833,525 B2
(45) Date of Patent: Nov. 16, 2010

(54) CRYSTALS OF WHOLE ANTIBODIES AND FRAGMENTS THEREOF AND METHODS FOR MAKING AND USING THEM

(76) Inventors: Bhami Shenoy, 16 Westgate Dr., T-6, Woburn, MA (US) 01801; Chandrika P. Govardhan, 9 Scotland Rd., Lexington, MA (US) 02420; Mark X. Yang, 59 Bridge St., Newton, MA (US) 02458; Alexey L. Margolin, 193 Upland Ave., Newton, MA (US) 02161

( * ) Notice: Subject to any disclaimer, the term of this patent is extended or adjusted under 35 U.S.C. 154(b) by 605 days.

(21) Appl. No.: 10/034,950

(22) Filed: Dec. 26, 2001

(65) Prior Publication Data

US 2002/0136719 A1   Sep. 26, 2002

Related U.S. Application Data

(60) Provisional application No. 60/258,704, filed on Dec. 28, 2000.

(51) Int. Cl.
*A61K 39/395* (2006.01)
*A61K 39/00* (2006.01)
*G01N 31/00* (2006.01)

(52) U.S. Cl. ............ 424/130.1; 436/4; 424/178.1
(58) Field of Classification Search ............ 530/387.1, 530/387.3, 388.1, 387.2, 387.7, 389.1, 389.7
See application file for complete search history.

(56) References Cited

U.S. PATENT DOCUMENTS

| 4,334,024 | A |   | 6/1982  | Johal ............................ 435/232 |
| 4,959,351 | A | * | 9/1990  | Grau ................................. 514/4 |
| 5,510,118 | A |   | 4/1996  | Bosch et al. ................. 424/489 |
| 5,780,599 | A | * | 7/1998  | Junker et al. ................ 530/399 |
| 5,849,296 | A | * | 12/1998 | Navia et al. ............... 424/178.1 |
| 5,904,935 | A |   | 5/1999  | Eckenhoff et al. ........... 424/489 |
| 6,011,001 | A |   | 1/2000  | Navia et al. ...................... 514/2 |
| 6,042,824 | A |   | 3/2000  | Khalaf ........................ 424/94.6 |
| 6,140,475 | A |   | 10/2000 | Margolin et al. ............. 530/402 |
| 6,310,038 | B1| * | 10/2001 | Havelund ........................ 514/4 |

FOREIGN PATENT DOCUMENTS

| WO | WO 91/09943    |   | 7/1991  |
| WO | WO 96/40049    |   | 12/1996 |
| WO | 97/08300 A1    |   | 3/1997  |
| WO | 97/44445 A1    |   | 11/1997 |
| WO | 98/46732 A1    |   | 10/1998 |
| WO | WO 99/55310    |   | 11/1999 |
| WO | WO 9955310 A1  | * | 11/1999 |
| WO | WO 00/52150    |   | 9/2000  |
| WO | WO 00/77281    |   | 12/2000 |

OTHER PUBLICATIONS

Harris et al. (Proteins: Struct. Funct. Genet. 1995; 23: 285-289).*
Hoedemaeker et al. (J. Biol. Chem. 1997; 272 (47): 29784-29789).*
Remicade (Remicade, Package Insert, Aug. 1998).*
McPherson (Eur. J. Biochem. 1990; 189: 1-23).*
Pollock et al. (J. Immunol. Methods 1999;231(1-2):147-57).*
Creighton, T.E. (Proteins: Structures and Molecular Properties, 2nd Ed., W.H. Freeman and Company, 1993).*
Drenth, "Principles of Protein X-Ray Crystallography", 2nd Edition, 1999 Springer-Verlag New York Inc., Chapter 1, pp. 1-21.*
Weber, Overview of Crystallization Methods. Methods in Enzymology, 1997, vol. 276, pp. 13-22.*
Jen et al. Diamonds in the Rough: Protein Crystals from a Formulation Perspective. Pharmaceutical Research. 2001. vol. 18, No. 11, pp. 1483-1488.*
Cheetham et al. "Crystal Structures of a Rat Anti-CD52 (CAMPATH-1) Therapeutic Antibody Fab Fragment and its Humanized Counterpart". Journal of Molecular Biology. 1998. vol. 284, pp. 85-99.*
Ely et al. Mobile Fc Region in the Zie IgG2 Cryoglobulin: Comparison of Crystals of the F(ab')2 Fragment and the Intact Immunoglobulin. Biochemistry. 1978. vol. 17, No. 5, pp. 820-823.*
McPherson, A. Current Approaches to Macromolecular Crystallization. European Journal of Biochemistry. 1990. vol. 189, pp. 1- 23.*
Kundrot, C.E. Which Strategy for a Protein Crystallization Project? Cellular Molecular Life Science. 2004. vol. 61, pp. 525-536.*
Cudney R. Protein Crystallization and Dumb Luck. The Rigaku Journal. 1999. vol. 16, No. 1, pp. 1-7.*
Klyushnichenko, V. Protein crystallization: From HTS to kilogram-scale. Current Opinion in Drug Discovery and Development. 2003, vol. 6, No. 6., pp. 848-854.*
Chayen (2004), "Turning protein crystallisation from an art into a science", Current Opinion in Structural Biology, 2004, 14: 577-583.*
Yang et al., Crystalline monoclonal antibodies for subcutaneous delivery, PNAS Jun. 10, 2003, vol. 100, pp. 6934-6939.*
Baselga et al., "Recombinant Humanized Anti-HER2 Antibody (Herceptin) Enhances the Antitumor Activity of Paclitaxel and Doxorubicin against HER2/neu Overexpressing Human Breast Cancer Xenografts," *Cancer Res*, vol. 58, pp. 2825-2831 (1998).
Bertolini et al., Endostatin, an antiangiogenic drug, induces tumor stabilization after chemotherapy or anti-CD20 therapy in a NOD/SCID mouse model of human high-grade non-Hodgkin lymphoma, *Neoplasia*, vol. 96, pp. 282-87 (2000).
Blanco et al., "Protein encapsulation and release from poly(lactide-co-glycolide) microspheres: effect of the protein and polymer properties and of the co-encapsulation of surfactants," *Eur. J. Pharm. Biopharm.* vol. 45, pp. 285-94 (1998).
Braden et al., "X-ray crystal structure of an anti-Buckminsterfullerene antibody Fab fragment: Biomolecular recognition of $C_{60}$," *Proc. Natl. Acad. Sci. USA*, vol. 97, pp. 12193-12197 (2000).
Brange et al., "Chemical Stability of Insulin. 1. Hydrolytic Degradation During Storage of Pharmaceutical Preparations,") *Pharm. Res.*, vol. 9, pp. 715-726 (1992).

(Continued)

*Primary Examiner*—David J Steadman
*Assistant Examiner*—Alexander D Kim
(74) *Attorney, Agent, or Firm*—Cooley, LLP

(57) ABSTRACT

This invention relates to crystals of whole antibodies and fragments thereof, and formulations and compositions comprising such crystals. More particularly, methods are provided for the crystallization of high concentrations of whole antibodies, and fragments thereof, in large batches, and for the preparation of stabilized whole antibody crystals for use alone, or in dry or slurry formulations or compositions. This invention also relates to methods for stabilization, storage and delivery of biologically active whole antibody crystals.

41 Claims, 15 Drawing Sheets

OTHER PUBLICATIONS

Covaceuszach et al., "Purification, crystallization and preliminary X-ray analysis of the Fab fragment from MNAC13, a novel antagonistic anti-tyrosine kinase A receptor monoclonal antibody" *Acta. Crystallogr. D. Biol. Crystallogr.*, vol. 57, pp. 1307-1309 (2001).

Dong et al., "Secondary Structure of the Pentraxin Female Protein in Water Determined by Infrared Spectroscopy: Effects of Calcium and Phosphorylcholine," *Biochemistry*, vol. 31, pp. 9364-9370 (1992).

Dong et al., "Infrared Spectroscopic Studies of Lyophilization- and Temperature-Induced Protein Aggregation," J Pharm. Sci., vol. 84, pp 415-424 (1995).

Harris et al., "Comparison of the conformations of two intact monoclonal antibodies with hinges," *Immunol. Rev.*, vol. 163, pp. 35-43 (1998).

Harris et al., "Crystallographic Structure of an Intact IgG1 Monoclonal Antibody," *J. Mol. Biol.*, vol. 275, pp. 861-872 (1998).

Ito, et al., "Crystallization and preliminary X-ray crystallographic studies on a Fab fragment of the mouse anti-human Fas monoclonal antibody HFE7A," *Acta. Crystallogr. D. Biol. Crystallogr.*, vol. D57,. pp. 1700-1702 (2001).

Kim et al., "Gene therapy for established murine collagen-induced arthritis by local and systemic adenovirus-mediated delivery of interleukin-4," *Arthritis Res.*, vol. 2, pp. 293-302 (2000).

Küttner et al., "A phage library-derived single-chain Fv fragment in complex with turkey egg-white lysozyme: characterization, crystallization and preliminary X-ray analysis," *Molecular Immunology*, vol. 35, pp. 189-194 (1998).

Malfait et al., "Chronic Relapsing Homologous Collagen-Induced Arthritis in DBA/1 Mice as a Model for Testing Disease-Modifying and Remission-Inducing Therapies," *Arthritis Rheum.*, vol. 44, pp. 1215-1224 (2001).

McPherson, "Preliminary Analysis: Mounting and aligning procedures," in *Preparation and Analysis of Protein Crystals*, pp. 214-227 (John Wiley & Sons Publishing) (1989).

Mylvaganam et al., "Structural Basis for the Binding of an Anti-cytochrome *c* Antibody to its Antigen: Crystal Structures of FabE8-Cytochrome *c* Complex to 1.8 Å Resolution and FabE8 to 2.26 Å Resolution," *J. Mol. Biol.*, vol. 281, pp. 301-322(1998).

Pekarek et al., "Double-walled polymer microspheres for controlled drug release," *Nature*, vol. 367, pp. 258-260 (1994).

Pichla et al. "The Crystal Structure of a Fab Fragment to the Melanoma-Associated GD2 Ganglioside," *J. Struct. Biol.*, vol. 119, pp. 6-16 (1997).

Pietras et al., "Monoclonal Antibody to HER-2/*neu* Receptor Modulates Repair of Radiation-induced DNA Damage and Enhances Radiosensitivity of Human Breast Cancer Cells Overexpressing This Oncogene," *Cancer Research*, vol. 59, pp. 1347-1355 (1999).

Pikal et al., "Quantitative Crystallinity Determinations for β-Lactam Antibiotics by Solution Calorimetry: Correlations with Stability," *J. Pharm. Sci.*, vol. 67, pp. 767-773 (1978).

Pikal et al., "The Stability of Isulin in Crystalline and Amorphous Solids: Observation of Greater Stability for the Amorphous Form," *Pharm. Res.*, vol. 14, pp 1379-1387 (1997).

Rodgers, "Practical Cryocrystallography," *Methods in Enzymology*, vol. 276, pp. 183-203 (1997).

Saul et al., "Structure of the Fab fragment from F124, a monoclonal antibody specific for hepatitis B surface antigen," *Acta. Crystallogr. D. Biol. Crystallogr.*, vol. D56, pp. 945-951 (2000).

Shenoy et al., "Stability of Crystalline Proteins," *Biotechnol. Bioeng.*, vol. 73, pp. 358-369 (2001).

Sohi et al., "Crystallaization and Preliminary X-ray Analysis of the Fab Fragment of a Human Monoclonal IgM Rheumatoid Factor (2A2)," *J. Mol. Biol.*, vol. 242, pp. 706-708 (1994).

Sullivan et al., "Sustained release of progesterone and estradiol from the SABER™ delivery system: In vitro and in vivo release rates," *Proceed. Int'l. Symp. Control. Rel. Bioact. Mater.*, vol. 25, pp. 653-654 (1998).

Yoshino, "Treatment with an Anti-IL-4 Monoclonal Antibody Blocks Suppression of Collagen-Induced Arthritis in Mice by Oral Administration of Type II Collagen," *J. Immunol.*, vol. 160, pp. 3067-3071 (1998).

Hampton Crystal Screen, 2000-2002, pp. 1-4, Hampton Research, 27632 El Lazo Road, Suite 100, Laguna Nigel, California, 92677-3913.

Adams et al., "Generating improved single-chain Fv molecules for tumor targeting," *Journal of Immunological Methods*, 231:249-260 (1999).

Boehm et al., "Crystal structure of the anti-(cacinoembryonic antiggen) single-chain Fv antibody MFE-23 and a model for antigen binding based on intermolecular contacts," *The Biochemical Journal*, 346(519-528 (2000).

Essig et al., "Crystallization of single-chain Fv proteins," *Journal of Molecular Biology*, 234(3):897-901, (1993).

Matthey, et al., "Recombinant immunotoxins for the treatment of Hodgkin's Disease (review)," *International Journal of Molecular Medicine*, 6(5):509-514 (2000).

Chayen et al., Recent Advances in Methodology for Crystallization of Biological Macromolecules, *Journal of Crystal Growth*, 198-199:649-655 (1999).

Hainsworth et al., "Monoclonal antibody therapy in lymphoid malignancies," 5(5):376-384 (2000).

McPherson et al., "Crystallization of Macromolecules: General Principles," *Methods in Enzymology* 114:112-120 (1985).

Saphire et al., "Crystallization and Preliminary Structure Determination of an Intact Human Immunoglobulin, b12: An Antibody that Broadly Neutralizes Primary Isolates of HIV-1," *Acta Cryst.*, D57:168-171 (2001).

Schwarz et al., "Anti-TNF-Alpha Therapy as Clinical Intervention for Periprosthetic Osteolysis," *Arthritis Research*, 2:165-168 (2000).

Van Assche et al., "Anti-TNF agents in Crohn's Disease," *Expert Opinion in Investigational Drugs*, 9(1):103-111 (2000).

Kuznetsov, Yu G. et al: "Chimeric human-simian anti-CD4 antibodies form crystalline high symmetry particles" Journal of Structural Biology, vol. 131, No. 2, Aug. 2000 pp. 108-115.

* cited by examiner

Figure 1: Rituximab Crystals

Figure 2: Infliximab Crystals
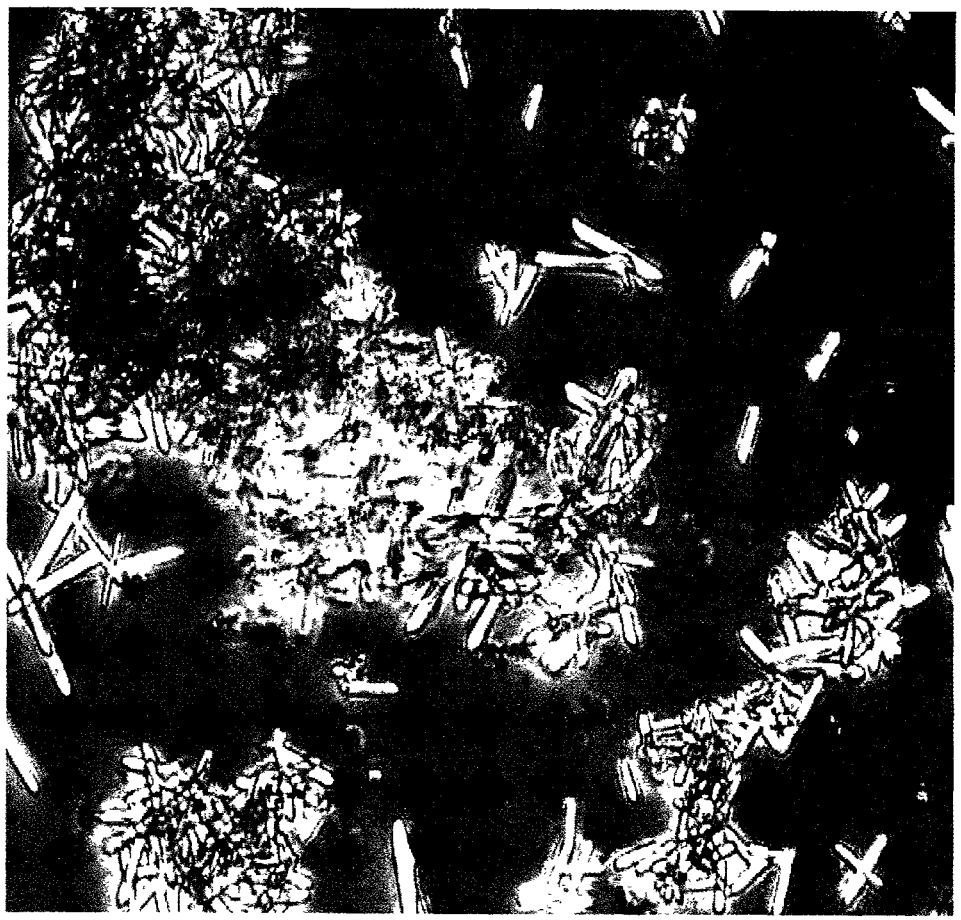

Figure 3: Rituximab Cube-shaped Crystals

Figure 4: Rituximab Small Needle-like Crystals

Figure 5: Trastuzumab Crystals

Figure 6: Trastuzumab Long Needle-like Crystals

Figure 7: Infliximab Star-shaped Crystals
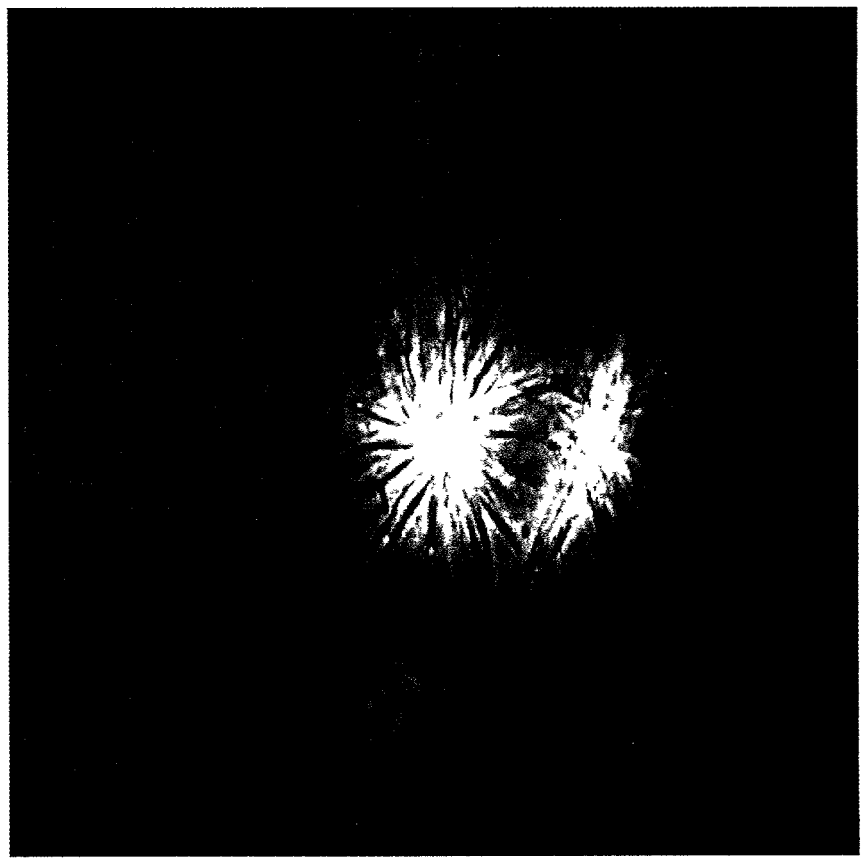

Figure 8: Crystallized Rituximab-Induced Direct Cytotoxicity
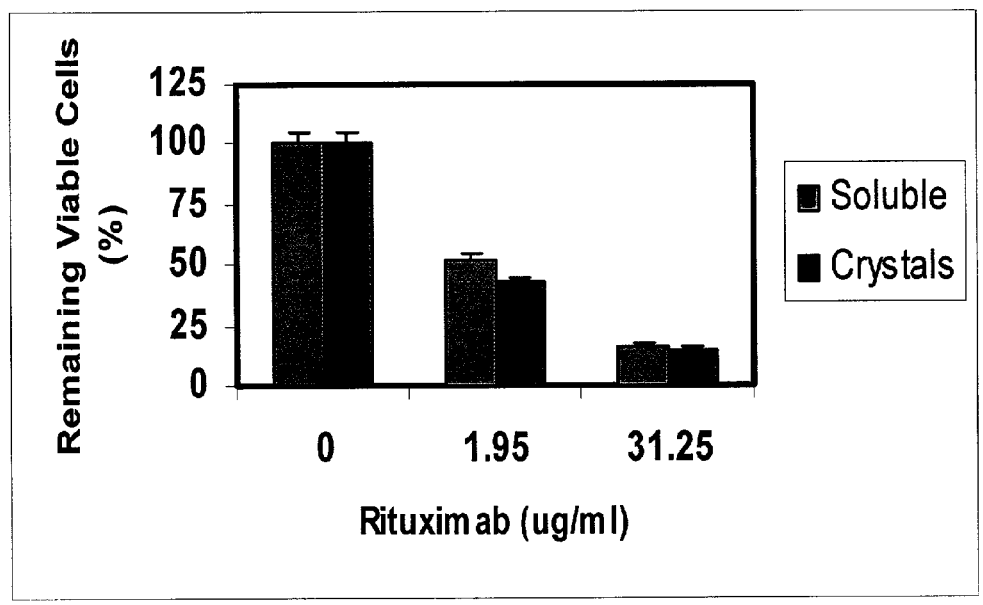

Figure 9: Crystallized Rituximab-Induced Complement-Dependent Cytotoxicity
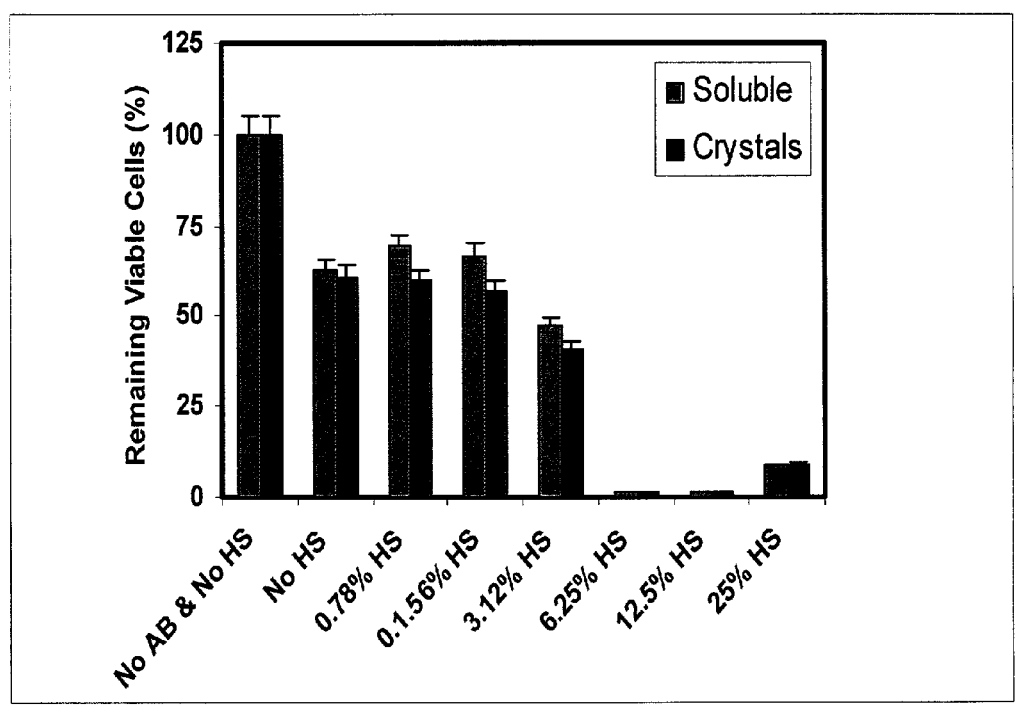

Figure 10: Analysis of Dissolved Rituximab Crystals
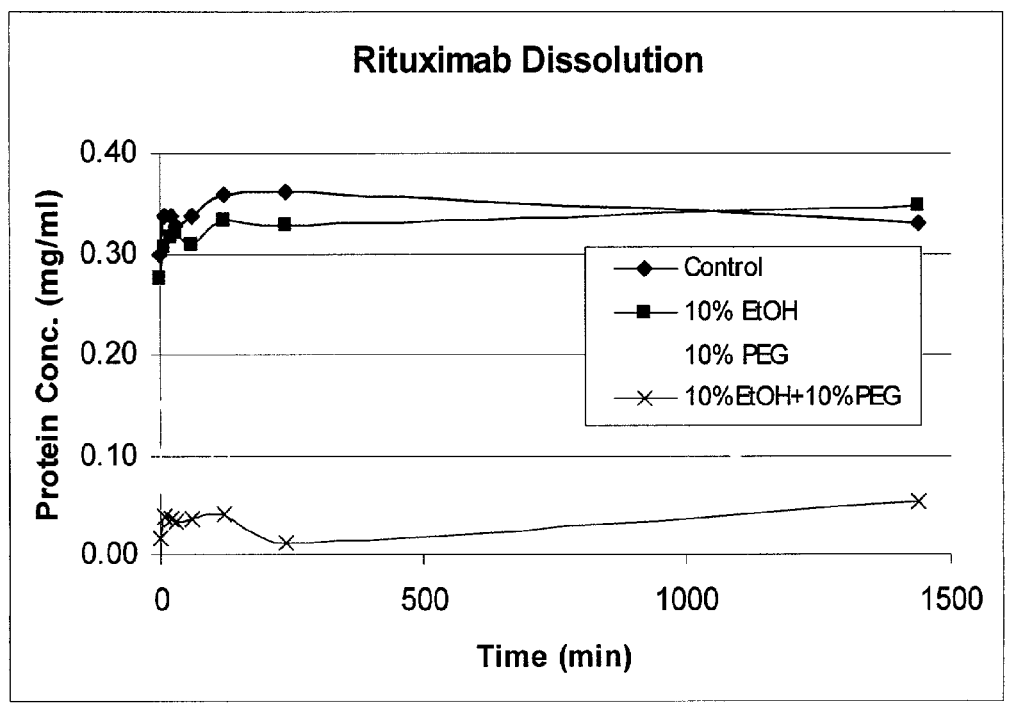

Figure 11: Analysis of Dissolved Trastuzumab Crystals
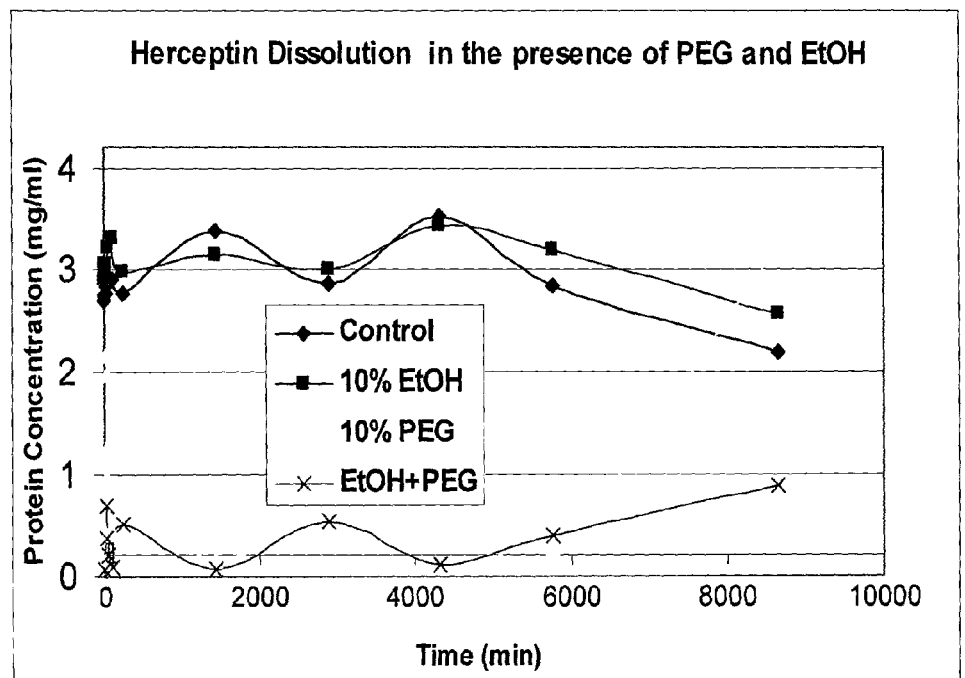

Figure 12: Stability of Rituximab in the Crystalline Form
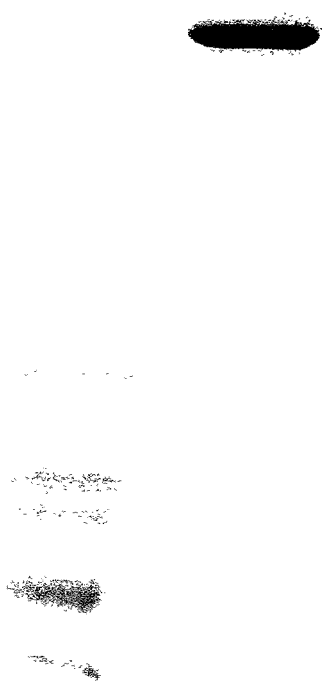

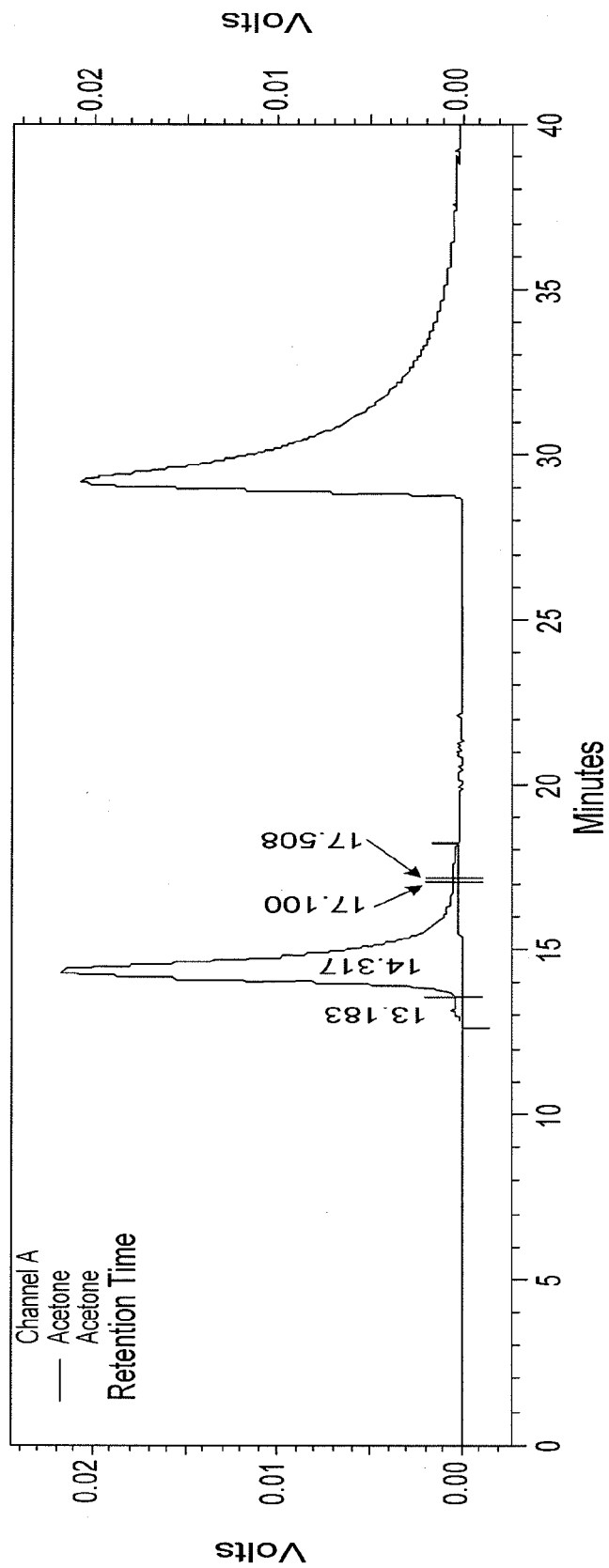
Figure 13: Crystalline Trastuzumab after treatment with Acetone

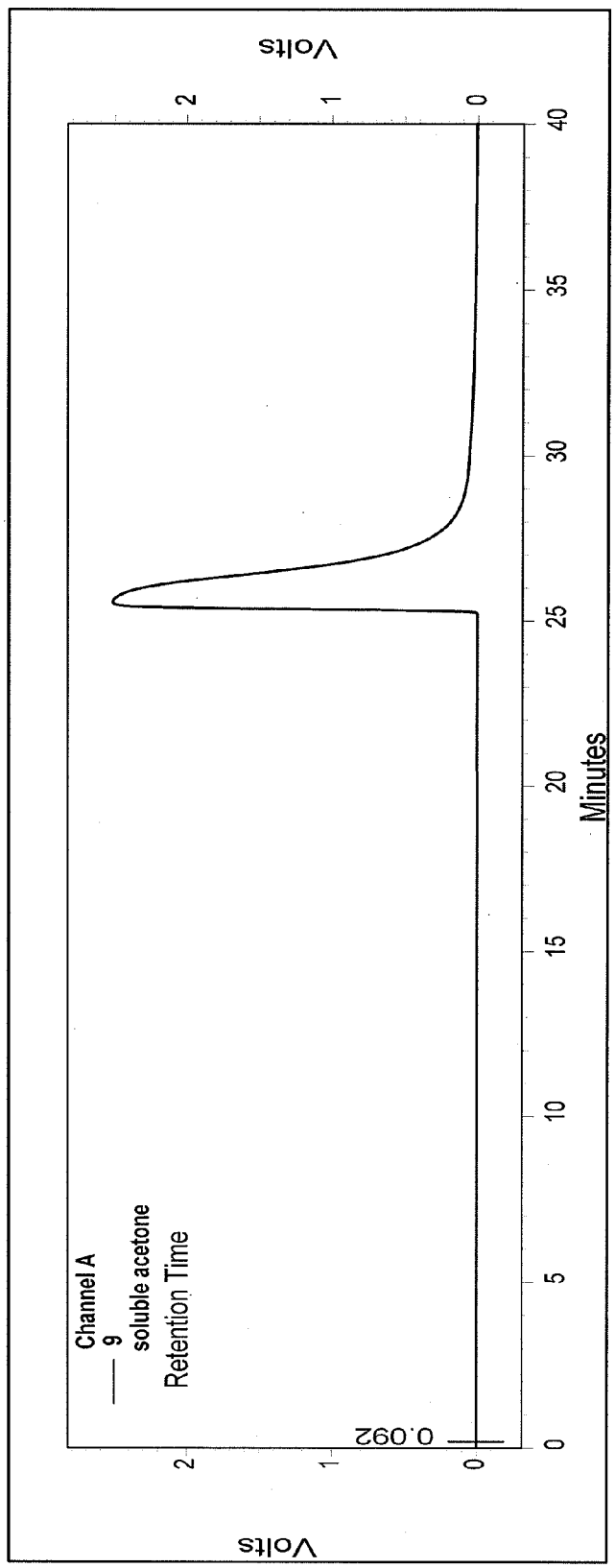
Figure 14: Soluble Trastuzumab after treatment with Acetone

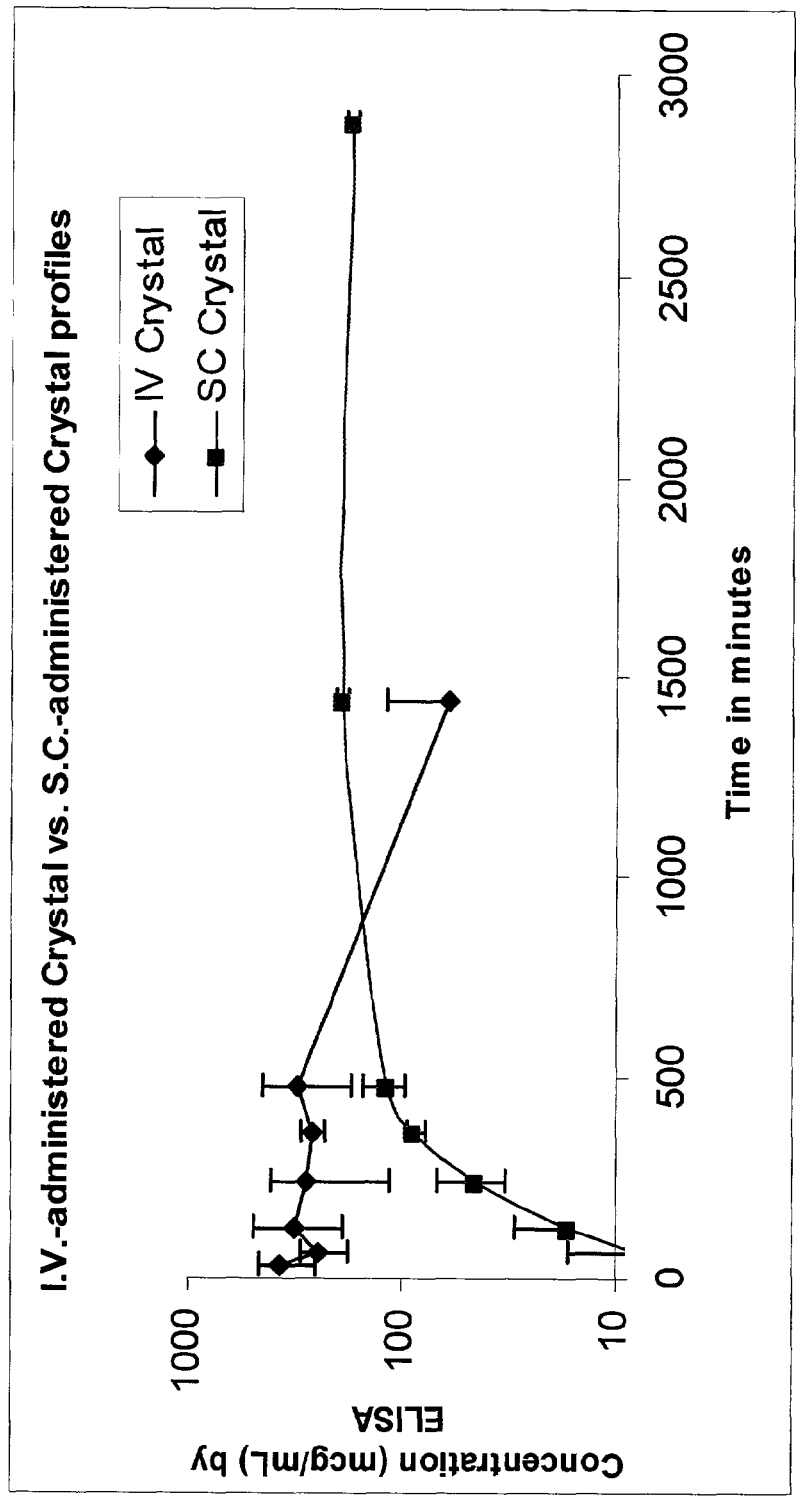
Figure 15: Bioavailability of Crystalline Trastuzumab Administered Intravenously (I.V.) or Subcutaneously (S.C.)

CRYSTALS OF WHOLE ANTIBODIES AND FRAGMENTS THEREOF AND METHODS FOR MAKING AND USING THEM

This application claims the priority benefit of U.S. Provisional Application Ser. No. 60/258,704, filed Dec. 28, 2000, the content of which is incorporated by reference in its entirety.

TECHNICAL FIELD OF THE INVENTION

This invention relates to crystals of whole antibodies and fragments thereof, and formulations and compositions comprising such crystals. More particularly, methods are provided for the crystallization of high concentrations of whole antibodies, and fragments thereof, in large batches, and for the preparation of stabilized whole antibody crystals for use alone, or in dry or slurry formulations or compositions. This invention also relates to methods for stabilization, storage and delivery of biologically active whole antibody crystals.

The present invention further relates to methods using whole antibody crystals, antibody fragment crystals, or compositions or formulations comprising such crystals for biomedical applications, including biological delivery to humans and animals. More particularly, highly concentrated whole antibody or antibody fragment crystal formulations or compositions are useful for delivery of large amounts of antibodies in a small volume to a subject, when and where they are needed. According to one embodiment of this invention, whole antibody crystals or antibody fragment crystals are used as a carrier-free delivery system which can slowly release active whole antibodies or fragments thereof, to a subject, where and when they are needed. According to an alternate embodiment of this invention, whole antibody crystals or antibody fragment crystals, or crystal formulations thereof, are encapsulated within a matrix comprising a polymeric carrier to form a composition.

Methods are also provided for preparing stabilized formulations of whole antibody crystals or antibody fragment crystals using pharmaceutical ingredients or excipients and optionally encapsulating the crystals or crystal formulations in a polymeric carrier to produce compositions and using such crystals for biomedical applications, including delivery of therapeutic proteins and vaccines.

BACKGROUND OF THE INVENTION

Antibodies, through their exquisite ability to specifically target a distinct antigen on an endogenous cell, bacteria, virus, or toxin, constitute powerful therapeutic agents characterized by limited side effects. Several antibodies introduced onto the market over the past few years have achieved astonishing success in treating a variety of diseases, including cancer and inflammatory, cardiovascular, respiratory, and infectious diseases. There are currently approximately 480 launched and developmental antibody programs worldwide, 83% of which are located in the United States. Over 20% of all biopharmaceuticals currently being evaluated in clinical trials are antibodies, according to the Pharmaceutical Research Institute of America reports. The projected United States antibody market is anticipated to increase about ten-fold over the next decade, to $10.1 billion in 2010 (*The Genesis Report: 25+Business Development & Innovation Opportunities in Monoclonal Antibodies-Emerging Opportunities in 2010*, The Genesis Group, Montclair, N.J.). In contrast to such efforts in antibody development, techniques for their purification, stabilization or subsequent delivery are often limited.

It is imperative that the higher order three-dimensional architecture or tertiary structure of an antibody be preserved until such time that the individual antibody molecules are required to perform their unique function. To date, a limiting factor for the use of antibodies, particularly in therapeutic regimens, remains the sensitivity of antibody structure to chemical and physical denaturation encountered during delivery. Various approaches have been employed to overcome these barriers. However, these approaches often incur loss of protein activity or the additional expense of protein stabilizing carriers or formulations.

The stability of small molecule crystalline drugs is such that they can withstand extreme forces during the manufacturing process (see U.S. Pat. No. 5,510,118). Such forces are associated with milling nanoparticles of crystalline material of relatively insoluble drugs and include: shear stress, turbulent flow, high impact collisions, cavitation and grinding. Small molecular crystalline compounds have been recognized as being much more stable toward chemical degradation than the corresponding amorphous solid [Pical, M. J., Lukes, A. L., Lang, J. E. and Gaines, *J. Pharm. Sci.* 67:767 (1978)].

To date, those of skill in the art recognize that the greatly enhanced stability of the crystalline state observed for small molecules does not translate to biological macromolecules, such as whole antibodies [Pical, M. J. and Rigsbee, D. R., *Pharm. Res.* 14:1379 (1997)]. For example, aqueous suspensions of crystalline insulin are only slightly more stable (to the degree of a factor of two) than corresponding suspensions of amorphous phase [Brange, J., Langkjaer, L., Havelund, S. and Volund, A., *Pharm. Res.* 9:715 (1992)]. In the solid state, lyophilized amorphous insulin is more stable than lyophilized crystalline insulin under all conditions investigated so far [Pical, M. J. and Rigsbee, D. R., Pharm. Res. 14:1379 (1997)]. However, using two model proteins, glucose oxidase and lipase, Shenoy et al. demonstrated that dry crystalline formulations can be significantly more stable than their amorphous counterparts [Shenoy, B. et al., Biotechnol Bioeng. 73(5):358-69 (2001)]. Surprisingly, the present invention provides crystals of whole antibodies and crystals of single-chain Fv (scFv) antibody fragments or Fab antibody fragments (the "ab" stands for "antigen-binding") that are more stable than their soluble antibody or antibody fragment counterparts.

Despite recent progress in protein technology generally, two problems continue to limit the use of biological macromolecules in industry and medicine. The first problem relates to molecular stability and sensitivity of higher order tertiary structures to chemical and physical denaturation during manufacturing and storage. Second, the field of biological delivery of therapeutic proteins requires that vehicles be provided which release native proteins, such as whole antibodies, at a rate that is consistent with the needs of the particular patient or disease process.

Although crystallization of whole antibodies has been a subject of significant interest for the last three decades, very few whole antibodies have ever been crystallized and, even then, solely in the context of structural studies [Harris L. J., Skaletsky, E., and McPherson, A., *J. Mol. Biol.* 275:861-72 (1998); Harris L. J., Larson, S. B., Skaletsky, E., and McPherson, A., *Immunological Reviews* 163:35-43 (1998)]. All of these crystals were obtained by vapor diffusion techniques, which yielded only a very small quantity of crystals for structural analysis. Such yields were far below those required for pharmaceutical, diagnostic or other commercial applications. Furthermore, such low yields were largely attributed to the difficulties in antibody crystallization due to their relatively large size, the presence of oligosaccharides on their surfaces, and the high degree of their segmental flexibility.

Fab antibody fragments have also been crystallized, but solely for use in X-ray crystallographic structural studies [See, e.g., Ito et al., *Acta Crystallogr. D. Biol. Crystallogr.* 57:1700-02 (2001); Covaceuszach et al., *Acta Crystallogr. D. Biol. Crystallogr.* 57:1307-09 (2001); Saul et al., Bioorg. Khim. 25:247-52 (1999); Pichla et al., *J. Struct. Biol.* 119:6-16 (1997); Maninder et al., *J. Mol. Biol.* 242:706-08 (1994)].

The following table provides a general comparison between crystallization for X-ray crystallographic structural studies and large-scale crystallization according to this invention:

| PARAMETER | X-RAY CRYSTALLO-GRAPHIC STUDIES | LARGE-SCALE CRYSTALLIZATION |
|---|---|---|
| Crystal size (longest dimension) | > 500 µm | 0.1-100 µm |
| Crystal quality | Very important | Less important |
| Growth rate | Not important | Important |
| Yield | Not important | Very important |
| Precipitate | Usually present | Rarely present |

Crystallization of whole antibodies, or fragments thereof, on a large scale, a process allowing an alternative route of delivery for therapeutic antibodies, has never before been explored.

Antibodies, and fragments thereof, are increasingly employed in the pharmaceutical, diagnostic and research industries. There is a great need for alternative stabilization procedures, which are fast, inexpensive and Moreover, stabilization procedures are needed that do not involve the excessive use of excipients, which can interfere with the functions of whole antibodies.

The present invention seeks to overcome barriers to the widespread use of antibodies for therapeutic and other biomedical purposes by providing methods for crystallizing whole antibodies, and fragments thereof, on a large scale.

SUMMARY OF THE INVENTION

The present invention overcomes the above-described obstacles by employing the most stable form of an active, whole antibody or fragment thereof, the crystalline form. In one embodiment of this invention, crystals of a whole antibody, or fragment thereof are used as is or in formulations or compositions, for various biomedical applications. According to alternate embodiments of this invention, crystals of a whole antibody, or fragment thereof, or formulations or compositions comprising them, may be: (1) stabilized by adding ingredients or excipients to the crystals, or (2) encapsulated within a polymeric carrier to produce a composition that contains each crystal for delivery to a subject and subsequent release of active, whole antibodies. Any whole antibody or fragment thereof may be crystallized and/or stabilized in this manner, according to the methods of this invention.

Various aspects of this invention are particularly advantageous.

First, crystallinity of stored materials is very important, since large scale crystallization can be introduced as a purification step and/or concentration step in clinical manufacturing processes, such as those for manufacturing therapeutics and vaccines. Moreover, large scale crystallization can replace some of the purification steps in the manufacturing process. For example, whole antibody crystallization can streamline the production of antibody formulations and compositions, making the procedure more efficient and affordable.

Second, macromolecular interactions which occur in solution are prevented or severely reduced in the crystalline state, due to considerable reduction of all reaction rates. Thus, the crystalline state is uniquely suited to the storage of mixtures of whole antibodies, or fragments thereof.

Third, solid crystalline preparations may be easily reconstituted to generate ready to use parenteral preparations having very high antibody concentrations. Typically, for subcutaneous administration, injection volumes of 1.5 ml or less are well tolerated. Thus, for proteins that are dosed at 1 mg/kg on a weekly basis, a protein concentration of at least 50 mg/ml is required and 100-200 mg/ml is preferred. Such concentrations are difficult to achieve in liquid preparations, due to problems of aggregation and viscosity of the liquid samples. In contrast, they can be achieved in the crystalline preparations, or formulations or compositions thereof, according to this invention.

Fourth, whole antibody crystals, or crystals of antibody fragments, also constitute a particularly advantageous form for pharmaceutical dosage preparation. The crystals may be used as a basis for slow release in vivo. As those of skill in the art will appreciate, particle size is important for the dissolution of crystals and release of activity. Those skilled in the art will also appreciate the rate of antibody release to be more predictable if the crystals have substantially uniform particle size and do not contain amorphous precipitate. Thus, whole antibody crystals, or crystals of antibody fragments, may be advantageously used on implantable devices, such as those described in PCT patent application WO 96/40049. Implant reservoirs are generally on the order of 25-250 µl. With this volume restriction, a preparation of high concentration (greater than 10%) and a minimum amount of suspension vehicle is preferred. Whole antibody crystals, or crystals of antibody fragments, according to this invention may also be easily formulated in non-aqueous suspensions in such high concentrations.

Fifth, the use of whole antibody crystals, or crystals of antibody fragments, and formulations and compositions comprising them, for slow release of the antibody after delivery to the intended site, advantageously permits the effective biological half-life of the whole antibody or antibody fragment in vivo to be increased.

Sixth, another advantage of whole antibody crystals, or crystals of antibody fragments, is that certain variables can be manipulated to modulate the release of macromolecules over time. For example, crystal size, shape, formulation with excipients that effect dissolution, and encapsulation into a polymer matrix can all be manipulated to produce delivery vehicles for the antibodies.

The process of crystallization of whole antibodies serves not only as a powerful protein purification or stabilization tool but also affords the most concentrated protein form possible. Such effects have significant potential for delivery to the intended delivery site of a high dose of whole antibodies, or fragments thereof. Furthermore, by employing crystals or crystal formulations or compositions of whole antibodies or antibody fragments, for delivery to subjects, it is possible to carry out the controlled release of the whole antibodies or fragments thereof at a rate that is consistent with the needs of the particular subject or disease process. As the rate of crystal dissolution depends on crystal morphology, crystal size and the presence of excipients, and the particular encapsulation technique or polymer preparation employed, crystalline whole antibodies or fragments thereof may also be used as a carrier-free slow release dosage form.

Whole antibodies or fragments thereof which are not stable when held in solution at ambient or elevated temperatures can nevertheless be successfully stored in dry crystalline form for long periods of time at such temperatures when they are crystallized according to the methods of this invention.

BRIEF DESCRIPTION OF THE DRAWINGS

FIG. 1 depicts the morphology of Rituximab (Rituxan™) crystals prepared as described in Example 6. Rituximab crystals formed in needle clusters.

FIG. 2 depicts the morphology of Infliximab (Remicade™) crystals prepared as described in Example 34. Infliximab crystals formed in rod-shaped clusters.

FIG. 3 depicts the morphology of Rituximab (Rituxan™) crystals prepared as described in Example 28. Rituximab formed cube-shaped crystals.

FIG. 4 depicts the morphology of Rituximab (Rituxan™) crystals prepared as described in Example 26. Rituximab formed small needle-like crystals.

FIG. 5 depicts the morphology of Trastuzumab (Herceptin™) crystals prepared as described in Example 31. Trastuzumab formed short needle-like crystals.

FIG. 6 depicts the morphology of Trastuzumab (Herceptin™) crystals prepared as described in Example 32. Trastuzumab formed long needle-like crystals.

FIG. 7 depicts the morphology of Infliximab (Remicade™) crystals prepared as described in Example 37. Trastuzumab formed star-shaped crystals.

FIG. 8 shows that crystallized Rituximab is capable of inducing a Direct Cytotoxicity response against the RAJI Lymphoma Cell Line. See Example 55.

FIG. 9 shows that crystallized Rituximab is capable of inducing Complement-Dependent Cytotoxicity against RAJI Lymphoma Cells. See Example 56.

FIG. 10 is a plot showing the results of an analysis of the stability of crystalline Rituximab in the presence of PEG, ethanol or a combination of PEG and ethanol. See Example 68.

FIG. 11 is a plot showing the results of an analysis of the stability of crystalline Trastuzumab (Herceptin™) in the presence of PEG, ethanol or a combination of PEG and ethanol. See Example 69.

FIG. 12 shows an SDS-PAGE gel of whole Rituximab antibody obtained by dissolving Rituximab crystals (as prepared on Example 1) that had been stored at room temperature for one month before being dissolved. See Example 64.

FIG. 13 is a chromatogram that depicts the results of treating crystalline Trastuzumab (Herceptin™) with acetone for three hours. The Trastuzumab remained whole and maintained its native structure. See Example 65.

FIG. 14 is a chromatogram that depicts the results of treating native (soluble) Trastuzumab (Herceptin™) with acetone for 20 minutes. The native/soluble Trastuzumab precipitated after the acetone treatment, demonstrating a loss of the structural integrity of the native Trastuzumab. See Example 65.

FIG. 15 is a plot that compares the rate at which crystalline Trastuzumab becomes bioavailable in the blood when administered intravenously (i.v.) with the rate of blood bioavailability when Trastuzumab is administered subcutaneously (s.c.).

DETAILED DESCRIPTION OF THE INVENTION

In order that the invention herein described may be more fully understood, the following detailed description is set forth. In the description, the following terms are employed:

Whole Antibody or Antibody Fragment—a whole antibody or antibody fragment, e.g., a single-chain Fv fragment or Fab antibody fragment, according to this invention, is a functional antibody or antibody fragment, i.e., that is able to recognize and bind to its specific antigen in vitro or in vivo, and may initiate any subsequent actions associated with antibody-binding, e.g., Direct Cytotoxicity, Complement-Dependent Cytotoxicity (CDC), Antibody-Dependent Cytotoxicity (ADCC).

Amorphous solid—a non-crystalline solid form of protein, sometimes referred to as "amorphous precipitate", which has no molecular lattice structure characteristic of the crystalline solid state.

Antibody—a glycoprotein of approximate MW 150 kD, that is produced by the humoral arm of the immune system of vertebrates in response to the presence of foreign molecules in the body. Antibodies are essential for the prevention and resolution of infection by microorganisms, e.g. parasites, bacteria and viruses. Antibodies perform this function by recognizing and binding, in a highly specific manner, protein (or, sometimes, other organic molecules including polysaccharides, glycoproteins, lipids, or nucleic acids) configurations called antigens (or epitopes), including those on invading microorganisms and their products. Antibodies bind their target antigens through highly specific interactions between hypervariable domains, called antigen-binding sites, on the antibody, and the epitope itself. Upon binding to the antigen, antibodies activate one or more of the many effector systems of the immune system that contribute to the neutralization, destruction and elimination of the infecting microorganism, or other antigen-containing entity, e.g. cancer cell.

Antibodies are also used for the treatment of cancer, inflammation, cardiovascular disease, and transplant rejection, by virtue of their specific binding and subsequent neutralization of the cellular targets, which are involved in disease states. For example, monoclonal antibody Infliximab binds to tumor necrosis factor and neutralizes its role in inflammation by blocking its interaction with cell surface receptor; while Rituximab targets malignant B lymphocytes by binding to their cell surface CD20 antigen.

A single antibody molecule has a structure composed of two identical heavy chains (each of approximate MW 50 kD) covalently bound to each other, and two identical light chains (each of approximate MW 25 kD), each covalently bound to one of the heavy chains. The four chains are arranged in a classic "Y" motif. The bottom "leg" of the "Y" is called the Fc region ("c" stands for "crystallizable" or, alternatively, "complement-binding") and is used to anchor the antibody within cell membranes, and also to bind macrophage cells and activate complement. The two "arms" at the top of the "Y" are called Fab regions (the "ab" stands for "antigen-binding"). Each Fab region contains a constant region (at the juncture of the Fab and the Fc regions) and a variable region (which extends to the tip of the "Y"). Each variable region contains identical antigen-binding sites (at regions within the variable regions called "hypervariable" regions) at each tip of the "Y". Thus, each Fab region has one antigen-binding site, and the complete antibody molecule therefore has two antigen-binding sites (i.e., is "bivalent"). The two antigen-binding sites on a naturally occurring antibody are identical to each other, and therefore the antibody is specific for one antigen (i.e., is "monovalent"). A number of molecular fragments of antibody molecules have been isolated to date. These do not occur naturally, but are engineered from one or more complete antibody molecules. These fragments include Fab fragments (a single Fab that is isolated from a complete antibody by digestion with the enzyme papain), and $F(ab')_2$ fragments (two Fabs covalently-bound to each other, produced by digesting the antibody with the enzyme pepsin). Fab fragments are monospecific, while $F(ab')_2$ fragments are bispecific. Recently, a number of engineered antibody fragments have been introduced. These include double-stranded Fv (dsFv) fragments and single-chain Fv (scFv) fragments (the "v" stands for "variable" in both cases). A dsFv fragment consists of an Fab fragment minus the constant regions, i.e., consisting only of the variable regions of a heavy and light chain covalently bound to each other. A scFv fragment is a single polypeptide chain, consisting of the variable region of a heavy chain linked via a peptide linker to the variable region of a light chain. Classically, both dsFv and scFv fragments are monovalent (and thus mono-specific). However, two dsFv fragments or two scFv fragments can themselves be linked to form a bispecific fragment (which would be analogous to an $F(ab')_2$ fragment without the constant regions). Furthermore, it is possible to link two dsFv fragments or scFv fragments with different antigen-binding sites (i.e., different specificities), to form a bi-specific fragment. Such fragments may be used as either research tools or therapeutic or diagnostic reagents.

There are five classes of antibodies (also called immunoglobulins) in humans: IgG, IgM, IgA, IgD, and IgE, each with its own unique characteristics and function. IgG, IgD, and IgE are all made up of one antibody molecule, while IgA can be made up of one, two or three such molecules and IgM consists of five. Furthermore, in humans, there are four subclasses of IgG (IgG1, IgG2, IgG3, or IgG4), and two subclasses each of IgM and IgA (1 and 2, respectively). For example, the monoclonal antibody Rituximab (Rituxan™) is an IgG1 antibody.

Though naturally occurring antibodies are derived from a single species, engineered antibodies and antibody fragments may be derived from more than one species of animal, i.e., may be chimeric. To date, mouse (murine)/human chimeric antibodies have been generated, though other species' combinations are possible. Chimeric antibodies have been further broken down into two subtypes: chimeric and humanized. Chimeric murine/human antibodies contain approximately 75% human and 25% mouse amino acid sequences, respectively. The human sequences represent the constant regions of the antibody while the mouse sequences represent the variable regions (and thus contain the antigen-binding sites) of the antibody. The rationale for using such chimeras is to retain the antigen specificity of the mouse antibody but reduce the immunogenicity of the mouse antibody (a murine antibody would cause an immune response against it in species other than the mouse) and thus be able to employ the chimera in human therapies. Chimeric antibodies also include those which comprise CDR regions from different human antibodies. CDR regions, also called hypervariable regions, are sequences within the variable regions of antibody molecules that generate the antigen-binding sites. CDR regions are so-named because the binding site is complementary in shape and charge distribution to the epitope recognized on the antigen.

Alternatively, chimeric antibodies comprise framework regions from one antibody and CDR regions from another antibody. Chimeric antibodies also include those which comprise CDR regions from at least two different human antibodies. Humanized antibodies contain approximately 90% (or more) human amino acid sequences. The only murine sequences present are those for the hypervariable region (that are the actual antigen-binding sites contained within the variable region). Humanized antibodies have minimal mouse immunogenicity as compared with chimeric antibodies.

There are generally two types of antibodies that can be distinguished by their specificities: polyclonal antibodies and monoclonal antibodies. Polyclonal antibodies are those that are found as the immunoglobulin fraction of blood, and are essentially a polyclonal mixture of many different types of antibodies specific for the different antigens the individual has been exposed to (i.e., they originate from many different clones of B lymphocytes (or B cells), the cell that produces antibodies).

Monoclonal antibodies are antibodies of a single specificity, i.e., that are derived from a single clone of B lymphocytes (B cells). These antibodies have exquisite specificity for their target antigens and also can be produced in high amounts (i.e., high titres). They are useful as markers for specific antigens (e.g., cancer antigens), as diagnostic agents (e.g., in assays to detect viruses like HIV-1), and as therapeutic agents. Whole monoclonal antibodies are those that have a classic molecular structure that includes two complete heavy chains and two complete light chains. This is distinguished from antibody fragments, such as Fab, $F(ab')_2$, Fc fragments, dsFv fragments, and scFv fragments.

Traditionally, monoclonal antibodies have been produced by fusing the antibody-producing B cell with an immortal hybridoma cell to generate B cell hybridomas, which continually produce monoclonal antibodies in cell culture. Another method that is traditionally used to generate monoclonal antibodies involves the expression of the monoclonal antibodies in bacterial cell culture using phage-display technology. Currently, however, monoclonal antibodies may be produced in vivo in large quantities in genetically-modified animals, such as cows and goats (Genzyme Transgenics), pigs and rabbits (Medarex, PPL Therapeutics), and chickens (Tranxenogen), and in plants, such as tobacco and corn (Epicyte, Integrated Protein Technologies, Meristem Croptech, and others). For example, large amounts of monoclonal antibodies can be found in the milk of genetically-modified goats (Genzyme Transgenics). Antibodies from all such sources may be crystallized according to this invention. Furthermore, as a result of transgenics, mice have been modified to contain and express the entire human B cell genome (which encodes human antibodies). Therefore, such transgenic mice (Abgenix) are a source of human antibodies for crystallization according to this invention. It should be noted that glycosylation is specific to the animal that is producing the antibodies. For example, human antibodies from sources other than humans will have subtly different glycosylation profiles. Therefore, the whole antibodies or single-chain Fv antibody fragments or Fab antibody fragments of this invention may display modified glycosylation or be deglycosylated. Antibodies which may be crystallized according to this invention also include derivatized antibodies. Such antibodies include those derivatized with polyethylene glycol or at least one carbohydrate moiety or least one methyl or ethyl group. Clinically relevant antibodies may also be classified according to the therapeutic area in which they are to be employed. Such antibodies include, for example, those for treating cancers (e.g., pancreatic cancer), inflammatory diseases (e.g., autoimmune diseases, arthritis), cardiovascular diseases (e.g., strokes), infectious disease (e.g., HIV/AIDS), respiratory diseases (e.g., asthma), tissue transplantation rejection and organ transplantation rejection. Such antibodies also include antibodies for radioimmunotherapy. Antibodies which may be crystallized according to the present invention include, for example, Abciximab, Palivizumab, Murumonab-CD3, Gemtuzumab, Trastuzumab, Basiliximab, Daclizumab, Etanercept and Ibritumomab tiuxetan.

Antibody activity release rate—the quantity of whole antibody, single-chain Fv antibody fragment or Fab antibody fragment dissolved per unit time.

Antigen—any substance or material that is specifically recognized and bound by an antibody. Antigens are typically small pieces of proteins (peptides) found on the surfaces of cells or invading microorganisms. Antibodies are thought to specifically recognize antigens as small as four amino acids in length, and the substitution of only one amino acid can abolish antibody recognition of the particular antigen for which it is specific.

Antigenicity—the ability of an antigen to be specifically recognized and bound by an antibody. An antigen is said to be in its antigenic conformation when it can be specifically recognized and bound by the antibody specific for the antigen. This is different from immunogenicity, which is the ability of an antigen to elicit the production of antibodies specific for the antigen.

Anti-idiotypic antibody—antibodies having specificity for the antigen-binding sites of other antibody molecules. Anti-idiotypic antibodies are generated in the following manner: an antigen elicits the production of antibodies (called Ab-1 or idiotypes) that are specific for that antigen. These antibodies (idiotypes) are then used as immunogens themselves to elicit a second generation of antibodies that are specific for Ab-1. These second generation antibodies (Ab-2) are called anti-idiotypic antibodies (or anti-idiotypes), and either mimic, or are closely related to, the initial antigen used to generate Ab-1. Such reactions also occur naturally in vivo, in response to antigenic stimulation, and by means of these antibody-antibody interactions, the immune system is able to, in essence, interact with itself. It has been postulated that by exploiting this capability, anti-idiotypic antibodies can be used to prevent certain infections, and treat some kinds of cancers and various immune and autoimmune diseases.

Antibody half-life—for antibodies in vivo, the time in which a given amount of whole antibody, a single-chain Fv antibody fragment or Fab antibody fragment, are reduced to 50% of its initial concentration. IgG typically has a half-life of about 21 days (though IgG3 has a half-life of only 7 days), while IgM, A, D, and E have typical half-lives of 10 days, 6 days, 3 days, and 2 days, respectively.

Antibody loading—the antibody content of formulations or compositions, as calculated as a percentage by weight of antibody, a single-chain Fv antibody fragment or Fab antibody fragment, relative to the weight of the dry preparation. A typical range of antibody loading is from 1-80%.

Antibody release—the release of active protein from a polymeric carrier, as controlled by one or more of the following factors: (1) degradation of the polymer matrix; (2) rate of crystal dissolution within the polymer matrix; (3) diffusion of dissolved protein through the polymer matrix; (4) protein loading; and (5) diffusion of biological medium into the antibody crystal/polymer matrix.

Aqueous-organic solvent mixture—a mixture comprising n % organic solvent, where n is between 1 and 99 and m % aqueous, where m is 100-n.

Bioavailability—the degree to which a substance, e.g., an active antibody or antibody fragment, administered in vivo, becomes available to the tissue to which the substance is targeted. According to this invention, bioavailability also refers to the degree to which a whole antibody, or fragment thereof, that has been administered in vivo as a crystal or a composition or formulation thereof, becomes available in the blood. According to this invention, bioavailability also refers to the ability of the substance, e.g., an active antibody or antibody fragment, to perform a function, e.g., direct cytotoxicity, at the target tissue once the substance has been delivered. Bioavailability may be measured in a number of ways, e.g., as the concentration of the substance, e.g., an active antibody or antibody fragment, measured as a function of time in the bloodstream.

Biocompatible polymers—polymers that are non-antigenic (when not used as an adjuvant), non-carcinogenic, non-toxic and which are not otherwise inherently incompatible with living organisms. Examples include: poly (acrylic acid), poly (cyanoacrylates), poly (amino acids), poly (anhydrides), poly (depsipeptide), poly (esters) such as poly (lactic acid) or PLA, poly (lactic-co-glycolic acid) or PLGA, poly (β-hydroxybutryate), poly (caprolactone) and poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

Biodegradable polymers—polymers that degrade by hydrolysis or solubilization. Degradation can be heterogenous—occurring primarily at the particle surface, or homogenous—degrading evenly throughout the polymer matrix.

Biological macromolecule—biological polymers such as proteins, deoxyribonucleic acids (DNA) and ribonucleic acids (RNA). For the purposes of this application, biological macromolecules are also referred to as macromolecules.

Composition—crystals of whole antibodies or crystals of single-chain Fv antibody fragments or Fab antibody fragments, or formulations thereof, which have been encapsulated within a polymeric carrier to form coated particles.

Controlled dissolution—dissolution of a crystal of an whole antibody or single-chain Fv antibody fragment or Fab antibody fragment, or a formulation or composition comprising such crystals, or release of the crystalline constituent of said crystal or formulation or composition that is controlled by a factor selected from the group consisting of the following: the surface area of said crystal; the size of said crystal; the shape of said crystal; the concentration of excipient component of the formulation or composition; the number and nature of excipient components of the formulation or composition; the molecular weight of the excipient components of the formulation or composition; the nature of the polymeric carriers, and combinations thereof.

Co-polymer—a polymer made with more than one monomer species.

Crystal—Crystals are one form of the solid state of matter, which is distinct from a second form—the amorphous solid state, which exists essentially as an unorganized, heterogeneous solid. Crystals are regular three-dimensional arrays of atoms, ions, molecules (e.g., proteins such as antibodies), or molecular assemblies (e.g., antigen/antibody complexes). Crystals are lattice arrays of building blocks called asymmetric units (which consist of the substance to be crystallized) that are arranged according to well-defined symmetries into unit cells that are repeated in three-dimensions. See Giegé, R. and Ducruix, A. Barrett, *Crystallization of Nucleic Acids and Proteins, a Practical Approach,* 2nd ed., pp. 1-16, Oxford University Press, New York, N.Y., (1999).

Dissolution of crystals—dissolving a crystal of a whole antibody or fragment thereof in order to recover soluble antibodies or antibody fragments.

Drying of Crystals of Whole Antibodies or Single-chain Fv Antibody Fragments or Fab Antibody Fragments—removal of water, organic solvent or liquid polymer by means including drying with N$_2$, air or inert gases, vacuum oven drying, lyophilization, washing with a volatile organic solvent followed by evaporation of the solvent, evaporation in a fume hood, tray drying, fluid bed drying, spray drying, vacuum drying, or roller drying. Typically, drying is achieved when the crystals become a free flowing powder. Drying may be carried out by passing a stream of gas over wet crystals. The gas may be selected from the group consisting of: nitrogen, argon, helium, carbon dioxide, air or combinations thereof.

Effective amount—an amount of a crystal of an whole antibody or a crystal of a single-chain Fv antibody fragment or Fab antibody fragment or crystal formulation or composition of this invention which is effective to treat, immunize, boost, protect, repair or detoxify the subject or area to which it is administered over some period of time.

Emulsifier—a surface active agent which reduces interfacial tension between polymer coated crystals and a solution.

Formulation—a combination of crystals of an whole antibody, or a combination of crystals of single-chain Fv antibody fragment or crystals of an Fab antibody fragment, and one or more ingredients or excipients, including sugars and biocompatible polymers. Examples of excipients are described in the *Handbook of Pharmaceutical Excipients*, published jointly by the American Pharmaceutical Association and the Pharmaceutical Society of Great Britain. For the purposes of this application, "formulations" include "crystal formulations." Furthermore, "formulations" include "whole antibody crystal formulations" and "single-chain Fv antibody fragment crystal formulations" and "Fab antibody crystal formulations".

Glycoprotein—a protein or peptide covalently linked to a carbohydrate. The carbohydrate may be monomeric or composed of oligosaccharides.

Homo-polymer—a polymer made with a single monomer species.

Immunotherapeutic—an antibody or single-chain Fv antibody fragment or Fab antibody fragment is immunotherapeutic when it has the activity of inducing protective immunity to a tumor cell, virus, or bacteria or stimulating the immune system to reduce or eliminate said tumor cell, virus or bacteria.

Ingredients—any excipient or excipients, including pharmaceutical ingredients or excipients. Excipients include, for example, the following:

Acidifying Agents
acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid Aerosol Propellants
butane, dichlorodifluoromethane, dichlorotetrafluoroethane, isobutane, propane, trichloromonofluoromethane Air Isplacements
carbon dioxide, nitrogen Alcohol Denaturants
denatonium benzoate, methyl isobutyl ketone, sucrose octacetate Alkalizing Agents
strong ammonia solution, ammonium carbonate, diethanolamine, diisopropanolamine, potassium hydroxide, sodium bicarbonate, sodium borate, sodium carbonate, sodium hydroxide, trolamine Anticaking Agents (see glidant)

Antifoaming Aents
dimethicone, simethicone

Antimicrobial Preservatives
benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol Antioxidants
ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient Buffering Agents
acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, histidine Capsule Lubricants (see tablet and capsule lubricant)

Chelating Agents
edetate disodium, ethylenediaminetetraacetic acid and salts, edetic acid Coating Agents
sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcystalline wax, zein Colors
caramel, red, yellow, black or blends, ferric oxide Complexing Agents
ethylenediaminetetraacetic acid and salts (EDTA), edetic acid, gentisic acid ethanolamide, oxyquinoline sulfate Desiccants
calcium chloride, calcium sulfate, silicon dioxide Emulsifying and/or Solubilizing Agents
acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax Filtering Aids
powdered cellulose, purified siliceous earth Flavors and Perfumes
anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin Glidant and/or Anticaking Agents
calcium silicate, magnesium silicate, colloidal silicon dioxide, talc Humectants
glycerin, hexylene glycol, propylene glycol, sorbitol Ointment Bases
lanolin, anhydrous lanolin, hydrophilic ointment, white ointment, yellow ointment, polyethylene glycol ointment, petrolatum, hydrophilic petrolatum, white petrolatum, rose water ointment, squalane Plasticizers
castor oil, lanolin, mineral oil, petrolatum, benzyl benyl formate, chlorobutanol, diethyl pthalate, sorbitol, diacetylated monoglycerides, diethyl phthalate, glycerin, glycerol, mono- and di-acetylated monoglycerides, polyethylene glycol, propylene glycol, triacetin, triethyl citrate, ethanol Polymer Embranes
cellulose acetate Solvents
acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water Sorbents
powdered cellulose, charcoal, purified siliceous earth Carbon Dioxide Sorbents
barium hydroxide lime, soda lime Stiffening Agents
hydrogenated castor oil, cetostearyl alcohol, cetyl alcohol, cetyl esters wax, hard fat, paraffin, polyethylene excipient, stearyl alcohol, emulsifying wax, white wax, yellow wax Suppository Bases
cocoa butter, hard fat, polyethylene glycol Suspending and/or Viscosity-increasing Agents
acacia, agar, alginic acid, aluminum monostearate, bentonite, purified bentonite, magma bentonite, carbomer 934 p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum Sweetening Agents
aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup Tablet Binders
acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup Tablet and/or Capsule Diluents
calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar Tablet Disintegrants
alginic acid, microcrystalline cellulose, croscarmellose sodium, corspovidone, polacrilin potassium, sodium starch glycolate, starch, pregelatinized starch Tablet and/or Capsule Lubricants
calcium stearate, glyceryl behenate, magnesium stearate, light mineral oil, polyethylene glycol, sodium stearyl fumarate, stearic acid, purified stearic acid, talc, hydrogenated vegetable oil, zinc stearate Tonicity Agent
dextrose, glycerin, mannitol, potassium chloride, sodium chloride Vehicle: flavored and/or sweetened
aromatic elixir, compound benzaldehyde elixir, iso-alcoholic elixir, peppermint water, sorbitol solution, syrup, tolu balsam syrup Vehicle: oleaginous
almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane
[1] [1] [1]

Vehicle: solid carrier
sugar spheres

Vehicle: sterile
Bacteriostatic water for injection, bacteriostatic sodium chloride injection Viscosity-increasing (see suspending agent)

Water Repelling Agent
cyclomethicone, dimethicone, simethicone

Wetting and/or Solubilizing Agent
benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol Preferred ingredients or excipients include: 1) salts of amino acids such as glycine, arginine, aspartic acid, glutamic acid, lysine, asparagine, glutamine, proline, histidine; 2) carbohydrates, e.g. monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-β-cyclodextrin and alike 8) inorganic salts, such as sodium chloride, potassium chloride, magnesium chloride, phosphates of sodium and potassium, boric acid ammonium carbonate and ammonium phosphate; 9) organic salts, such as acetates, citrate, ascorbate, lactate; 10) emulsifying or solubilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; and 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol and tyloxapol. A further preferred group of excipients or ingredients includes sucrose, trehalose, lactose, sorbitol, lactitol, inositol, salts of sodium and potassium such as acetate, phosphates, citrates, borate, glycine, arginine, polyethylene oxide, polyvinyl alcohol, polyethylene glycol, hexylene glycol, methoxy polyethylene glycol, gelatin, hydroxypropyl-β-cyclodextrin.

Insoluble and stable form—a form of crystal of an whole antibody or a single-chain Fv antibody fragment crystal or an Fab antibody fragment crystal which is insoluble in aqueous solvents, organic solvents or aqueous-organic solvent mixtures and which displays greater stability than the soluble form of the counterpart antibody or single-chain Fv antibody fragment or Fab antibody fragment. According to one embodiment of this invention, the phrase "insoluble and stable form" may denote a form of crystals which is insoluble in dry preparations but soluble in wet preparations. In any embodiment, the whole antibody crystals or crystals of a single-chain Fv antibody fragment or crystals of an Fab antibody fragment may be active in insoluble form. And in one embodiment, the whole antibody crystals or crystals of a single-chain Fv antibody fragment or crystals of an Fab antibody fragment may be active in insoluble form, then dissolve or are removed or digested once their function is complete. According to another embodiment of this invention, crystals of whole antibodies or fragments thereof may be crosslinked for added stability. According to another embodiment of this invention, metal ions, e.g., $Ca^{++}$, may be added to crystals of whole antibodies or fragments thereof, rendering the crystals more insoluble and more stable.

Label—incorporation of a label to a crystal of an whole antibody or of a single-chain Fv antibody fragment or of an Fab antibody fragment. Labels may be selected from the group consisting of radiolabels, enzyme labels, toxins, magnetic agents or drug conjugates.

LiQuid polymer—pure liquid phase synthetic polymers, such as poly-ethylene glycol (PEG), in the absence of aqueous or organic solvents.

Loss of shelf stability—the loss of specific activity and/or changes in secondary structure of a crystalline whole antibody or of a crystalline single-chain antibody Fv fragment or of a crystalline Fab antibody fragment as compared with the soluble (i.e., non-crystallized, native) antibody or single-chain Fv antibody fragment or Fab antibody fragment counterpart over time, when incubated under corresponding conditions.

Loss of stability—the loss of specific activity and/or changes in secondary structure of a crystalline whole antibody or of a crystalline single-chain antibody Fv fragment or of a crystalline Fab antibody fragment as compared with the soluble (i.e., non-crystallized) antibody or single-chain Fv antibody fragment or Fab antibody fragment counterpart over time, while in solution under corresponding conditions.

Macromolecules—proteins, glycoproteins, peptides, therapeutic proteins, DNA or RNA molecules, polysaccharides, lipoproteins, lipopolysaccharides.

Method of Administration—crystals of whole antibodies or single-chain Fv antibody fragment crystals or Fab antibody fragment crystals, or crystal formulations or compositions thereof, may be appropriate for a variety of modes of administration. These may include oral and parenteral administration. Examples of parenteral administration according to this invention include, but are not limited to, subcutaneous, intravenous, transdermal, intramuscular, pulmonary inhalation, intralesional, topical administration, needle injection, dry powder inhalation, skin electroporation, aerosol delivery, and needle-free injection technologies, including needle-free sub-cutaneous administration.

Microspheres—encapsulated crystalline material which is spherical or roughly or nearly spherical, and has a diameter between about 1 nm and about 1 mm.

Microparticulates—encapsulated crystalline material which has a diameter between about 1 nm and about 1 mm, but has no defined shape.

Mother Liquor—the buffer used for crystallization of macromolecules, e.g., proteins, nucleic acids.

Needle-free drug delivery devices and jet injections—delivery of a substance into the body of a mammal, or other suitable recipient, which does not involve using a sharp needle for injection. This may be a needle-free device which delivers the substance in a pressure-mediated manner. Examples of commercially-available needle-free injection devices or systems that can be used to administer crystals or crystal formulations or compositions of whole antibodies or antibody fragments according to this invention include, inter alia, Intraject™ (Weston Medical, Ltd.), Biojector2000® (Bioject, Inc.), Madajet™ (MADA Medical Products, Inc.), and J-Tip® (National Medical Products, Inc.), LectraJet™ (DCI, Inc.), Mesoflash® (also called Isojet™) (Prolitec), VACCI JET Electrique™ (ENDOS Pharma), and a two-stage fluid medicament jet injector (Avant Drug Delivery Systems, Inc.).

Organic solvents—any solvent of non-aqueous origin, including liquid polymers and mixtures thereof. Organic solvents suitable for the present invention include: acetone, methyl alcohol, methyl isobutyl ketone, chloroform, 1-propanol, isopropanol, 2-propanol, acetonitrile, 1-butanol, 2-butanol, ethyl alcohol, cyclohexane, N-methylpyrrolidinone (NMP), dioxane, ethyl acetate, dimethylformamide, dichloroethane, hexane, isooctane, methylene chloride, tert-butyl alcohol, toluene, carbon tetrachloride, or combinations thereof.

Pharmaceutically effective amount—an amount of a crystal of an whole antibody or of a single-chain Fv antibody fragment or of an Fab antibody fragment, or crystal formulation or composition thereof, which is effective to treat a condition in an living organism to whom it is administered over some period of time.

Plasticizing—use of a plasticizer, e.g., lanolin, ethanol, to make a formulation comprising a whole antibody crystal or antibody fragment crystal in a solution that becomes viscous after it is injected subcutaneously, forming a matrix. The resulting high viscosity matrix is adhesive, biodegradable and biocompatible. The antibody or antibody fragment is then released in a controlled manner from the matrix.

Polyethylene glycol (PEG) size—The size of the PEG moieties used according to this invention (e.g., inter alia, PEG 200, PEG 400, PEG 10,000, PEG 80,000) refers to the chain length, i.e., number of ethylene glycol residues in the PEG chain. For example, PEG 200 has 200 ethylene glycol residues in the PEG polymer, PEG 80,000 has 80,000 ethylene glycol residues in the PEG polymer, etc.

Polymer—a large molecule built up by the repetition of small, simple chemical units. The repeating units may be linear or branched to form interconnected networks. The repeat unit is usually equivalent or nearly equivalent to the monomer.

Polymeric carriers—polymers used for encapsulation of whole antibody crystals or crystals of single-chain Fv antibody fragments or crystals of Fab antibody fragments for delivery of such whole antibodies or antibody fragments, including biological delivery. Such polymers include biocompatible and biodegradable polymers. The polymeric carrier may be a single polymer type or it may be composed of a mixture of polymer types. Polymers useful as the polymeric carrier, include for example, poly (acrylic acid), poly (cyanoacrylates), poly (amino acids), poly (anhydrides), poly (depsipeptide), poly (esters) such as poly (lactic acid) or PLA, poly (lactic-co-glycolic acid) or PLGA, poly (β-hydroxybutyrate), poly (caprolactone) and poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, natural and synthetic polypeptides, alginate, cellulose and cellulose derivatives, collagen, fibrin, gelatin, hyaluronic acid, oligosaccharides, glycaminoglycans, sulfated polysaccharides, modified starches such as amylose starch, amylopectin starch, hydroxyethyl starch, methacrylate starch, and other starches, and any conventional material that will encapsulate protein crystals.

Prophylactically effective amount—an amount of a crystal of a whole antibody or single-chain Fv antibody fragment crystal or Fab antibody fragment crystal, or crystal formulation or composition thereof, which is effective to prevent a condition in an living organism to whom it is administered over some period of time.

Protein—a complex polymer containing carbon, hydrogen, oxygen, nitrogen and usually sulfur and composed of chains of amino acids connected by peptide linkages. The molecular weight range for proteins includes peptides of 1000 Daltons to glycoproteins of 600 to 1000 kilodaltons.

Protein delivery system—method or means for administering one or more of a protein, such as an antibody crystal, single-chain Fv antibody fragment crystal, Fab antibody fragment crystal, or formulation or composition comprising such crystals, to a biological entity.

Radiolabel—incorporation of a radiolabel to a protein, such as a crystal of an whole antibody or of a single-chain Fv antibody fragment or of an Fab antibody fragment. In situations where the radiolabel has a short half-life, as with $^{131}I$ or $^{90}Y$, the radiolabel can also be therapeutic, e.g., used in radioimmunotherapies against cancers. Various methods of labeling polypeptides and glycoproteins are known in the art and may be used. Examples of labels include, but are not limited to, the following radioisotopes or radionucleotides: $^{3}H$, $^{14}C$, $^{15}N$ $^{35}S$, $^{90}Y$, $^{99}Tc$, $^{111}In$, $^{125}I$, and $^{131}I$.

Reconstitution—dissolution of whole antibody crystals or crystals of a single-chain Fv antibody fragment or of an Fab antibody fragment, or formulations or compositions comprising such crystals, in an appropriate buffer or pharmaceutical preparation.

Room Temperature—for purposes of this invention, it will be understood by those of skill in the art that room temperature can be any temperature from about 20° C. to about 26° C.

Stabilization—the process of preventing the loss of specific activity and/or changes in secondary structure of a crystalline whole antibody or of a crystalline single-chain antibody Fv fragment or of a crystalline Fab antibody fragment as compared with the soluble antibody or single-chain Fv antibody fragment counterpart, or Fab antibody fragment counterpart, by preparing formulations or compositions of antibody or single-chain Fv antibody fragment or Fab antibody fragment crystals, with excipients or ingredients, including polymeric carriers.

Therapeutic antibody or single-chain Fv antibody fragment or Fab antibody fragments—a crystal of a whole antibody or single-chain Fv antibody fragment or Fab antibody fragment, or crystal composition or formulation thereof, according to this invention, which is administered to a living organism to treat a given illness or symptom thereof.

Vaccine antibody or single-chain Fv antibody fragment or Fab antibody fragments—an antibody or single-chain Fv antibody fragment or Fab antibody fragment that is elicited by (1) a native antigen, e.g., an antigen found on a pathogenic agent such as a virus, parasite, bacteria or tumor cell, or found on a tumor, or (2) an allergen. The protein activity of such vaccine antibodies or single-chain Fv antibody fragments or Fab antibody fragments is the induction of protective immune responses specific for a pathogenic agent, tumor, or allergen, or other antigen.

Crystallinity of Whole Antibodies and Fragments Thereof the Advantages Thereof

Crystallinity of macromolecules, such as whole antibodies, or fragments thereof, is of great value for their storage and delivery in vivo. However, few techniques exist for the preparation of large quantities of such crystalline macromolecules which are stable outside of the mother liquor. Crystals of proteins, such as whole antibodies and fragments thereof, must be handled with considerable care, since they are extremely fragile and contain a high proportion of solvent. It is well known in x-ray crystallography that the diffraction patterns from macromolecular crystals quickly degenerate upon dehydration in air. Normally, a crystal is carefully separated from its mother liquor and inserted into a capillary tube. The tube is sealed from the air using dental wax or silicone grease, along with a small amount of mother liquor inside to maintain hydration [McPherson, A., *Preparation and Analysis of Protein Crystals*, Robert E. Krieger Publishing, Malabar, p. 214 (1989)]. Another technique is to collect data from macromolecular crystals at cryogenic temperatures. The crystals are prepared and then rapidly cooled to prevent ice lattice formation in the aqueous medium. Instead of ice, a rigid glass forms, encasing the crystal with little damage. Crystals are then maintained at 100° K. to prevent crystal disintegrations [Rodgers, D. W., in *Methods in Enzymology* (Eds., Carter, C. W. and Sweet, R. M.) Academic Press, v.276, p. 183 (1997)]. While this technique allows one to maintain crystals outside of their mother liquor, it cannot be used at temperatures higher than 100° K.

In principle, dried crystals can be prepared by lyophilization. However, this technique involves rapid cooling of the material and can be applied only to freeze stable products. The aqueous solution containing a crystalline whole antibody or a crystalline single-chain antibody Fv fragment or a crystalline Fab antibody fragment is first frozen to between −40 and −50° C. Then, the ice is removed under vacuum. Ice formation is usually destructive to the protein crystal lattice, yielding a mixture of crystals and amorphous precipitate.

It is desirable to produce whole antibodies, in the crystalline state, that are pure and stable under storage conditions at ambient temperatures. Such crystals constitute a particularly advantageous form for dosage preparations of therapeutics and vaccines. The present invention advantageously provides formulations and compositions of crystals of whole antibodies. The present invention also provides formulations and compositions for storage of crystals of whole antibodies as either solid particles or dispersed in a non-aqueous solvent. Furthermore, the invention may be applied to the storage of a single type of biologically active whole antibody or a mixture of different types of whole antibodies that do not interact with each other.

In another embodiment, this invention provides a method for crystallizing single-chain Fv (scFv) fragments of antibodies, and using such crystals in various biomedical applications. Such scfv fragments are constructed by linking the variable region of an antibody heavy chain to a variable region of an antibody light chain through the use of a linker peptide. Due to their small size, scFv fragments allow tissue penetration more readily than do whole antibodies, and therefore may have valuable therapeutic applications for particular indications. It should be understood that crystals, crystal formulations or crystal compositions containing scFv fragments can be generated and utilized in the same manner applicable to crystals of whole antibodies, in the various embodiments of this invention.

In another embodiment, this invention provides a method for crystallizing Fab fragments of antibodies, and using such crystals in various biomedical applications. Such Fab fragments are generated by digesting a complete antibody with the enzyme papain, to yield antibody fragment molecules with one antigen binding site, as described above. Alternatively, Fab fragments may be generated by using genetic engineering technology. Due to their smaller size, Fab fragments allow tissue penetration more readily than do whole antibodies, and therefore may have particularly valuable therapeutic applications for particular indications. It should be understood that crystals, crystal formulations or crystal compositions containing Fab fragments can be generated and utilized in the same manner applicable to crystals of whole antibodies, in the various embodiments of this invention.

This invention allows crystallization of, and use of crystals of, all of the immunoglobulin classes IgG, IgM, IgA, IgD, IgE, and serum IgA (sIgA) as well as the subclasses IgG1, IgG2, IgG3 and IgG4, IgM1 and IgM2, and IgA1 and IgA2, as well as scFv fragments and Fab antibody fragments, from all the immunoglobulin classes and subclasses.

In another embodiment, this invention provides a method for rendering biologically active crystals of whole antibodies suitable for storage in suspensions comprising replacing the mother liquor with a non-aqueous solvent. In yet another embodiment, the crystalline slurry can be rendered solid by spinning out the first solvent and washing the remaining crystalline solid using a second organic solvent to remove water, followed by evaporation of the non-aqueous solvent.

Non-aqueous slurries of crystalline whole antibodies or scFv fragments or Fab fragments are especially useful for subcutaneous delivery, and intramuscular delivery, while solid preparations are ideally suited for pulmonary administration. As will be appreciated by those of skill in the art, pulmonary delivery is particularly useful for biological macromolecules which are difficult to deliver by other routes of administration.

Crystals of whole antibodies and crystals of single-chain Fv antibody fragments and crystals of Fab antibody fragments according to this invention are useful in diagnostic methods and kits. For example, such crystals may be used in a kit for diagnosing the presence a target antigen in a sample from a patient or another specimen. Such a kit may comprise a container and, optionally instructions for use. The crystals in the kit may be labelled with a detectable label. Methods for detecting a target antigen in a sample, such as a blood, tumor, cell, or tissue sample, may be carried out by mixing the sample with crystals of whole antibodies or crystals of single-chain Fv antibody fragments or Fab antibody fragments according to this invention and determining whether the sample binds to the antibody or fragment. The crystals used in such methods may be labelled with a detectable label.

Alternatively, crystals of whole antibodies or crystals of single-chain Fv antibody fragments and crystals of Fab antibody fragments according to this invention are useful in chromatography and purification methods, such as affinity chromatography. For example, affinity matrix purification of a protein may be carried out by:

(a) mixing with a binding buffer crystals of a whole antibody or crystals of a single-chain Fv antibody fragment or crystals of an Fab antibody fragment, wherein such antibody or antibody fragment has affinity for the protein to be purified;

(b) adding a protein solution containing the protein to be purified to the crystal/buffer mixture;

(c) incubating the entire mixture for a time and at a temperature sufficient to permit binding of the protein to the antibody or antibody fragment;

(d) washing the mixture with a wash buffer; and (e) eluting the protein with an elution buffer.

Stability of Encapsulated Crystals of Whole Antibodies

Those of skill in the art will appreciate that protein stability is one of the most important obstacles to the successful preparation of polymer microparticulate delivery systems that control the release of proteins. The stability of crystalline proteins, such as crystals of a whole antibody, or crystals of antibody fragments, encapsulated in polymeric carriers may be challenged at three separate stages: 1) manufacture of the antibody crystal composition, 2) antibody release from the resulting composition and 3) in vivo stability after the antibody release. During preparation of microparticles or microspheres containing soluble or amorphous proteins, the use of organic solvents and lyophilization are especially detrimental to protein stability. Subsequently, released proteins are susceptible to moisture-induced aggregation, thus resulting in permanent inactivation.

In order to achieve high protein stability during preparation of whole antibody crystals, crystals of antibody fragments, or formulations and compositions according to the present invention, it is necessary to restrict the mobility of individual whole antibody molecules—a result best achieved in the crystalline solid state. For the purpose of this application, solid state may be divided into two categories: amorphous and crystalline. The three-dimensional long-range order that normally exists in a crystalline material does not exist in the amorphous state. Furthermore, the position of molecules relative to one another is more random in the amorphous or liquid states, relative to the highly ordered crystalline state. Thus, amorphous proteins, including antibodies, may be less stable than their crystalline counterparts.

Maintaining Crystallinity

In order to use antibody crystals or antibody fragment crystals as the antibody source for preparing antibody formulations and compositions according to the present invention, the problem of protein crystal dissolution outside the crystallization solution ("mother liquor") had to be overcome. In order to maintain protein crystallinity, and hence stability, in the production of the crystals of whole antibodies, or crystals of antibody fragments, and formulations and compositions of this invention, several approaches may be used:

1. Crystals remain in the mother liquor in the course of producing antibody crystals encapsulated with polymeric carriers. Many compounds used in protein crystallization, such as salts, PEG and organic solvents, are compatible with polymer processing conditions.
2. Kinetics of dissolution. The rate of crystal dissolution outside the mother liquor depends on conditions, such as pH, temperature, presence of metal ions, such as Zn, Cu and Ca and concentration of precipitants. By varying these conditions, one can slow down the dissolution of crystals for several hours. At the same time, the process of microparticulate formation is very fast and normally takes seconds to minutes to complete.
3. Dried antibody crystals. The mother liquor can be removed by filtration and the remaining crystalline paste can be dried by air, under vacuum, by washing with water miscible organic solvents and/or by lyophilization or spray drying.
4. The crystal size and shape can be manipulated and controlled in the course of crystallization. Thus, a range of crystal morphologies, each having different dissolution kinetics and subsequently different sustained release profiles compared to amorphous proteins, is available.
5. Method of making a crystal formulation by exchanging the mother liquor to a pharmaceutically-acceptable solvent or solution to form a Subcutaneous Vehicle for controlled delivery in vivo: The mother liquor can be removed by centrifugation and the remaining crystalline material can be suspended in a pharmaceutically acceptable solvent (e.g., ethanol) for subcutaneous injections. The crystalline material may also be suspended in sucrose acetate isobutyrate (SAIB) or poly (lactic-co-glycolic acid) (PLGA) in N-methylpyrrolidinone (NMP), where it forms a gel under the skin once it comes into contact with aqueous body fluids. The gel then facilitates the controlled release of the antibody or fragment thereof.

Administration and Biological Delivery

To date, therapeutic proteins, such as antibodies, have generally been administered by frequent injection or infusion, due to their characteristic negligible oral bioavailability and short plasma life. Crystals of whole antibodies, or crystals of antibody fragments, as well as crystal formulations and compositions containing them, according to the present invention, (which include microparticulate-based sustained release systems for whole antibodies), advantageously permit improved patient compliance and convenience. Furthermore, because of increased bioavailability and increased stability of proteins in the crystalline state, more stable blood levels of the administered antibodies or antibody fragments can be achieved, potentially with lower dosages. Also, the slow and constant release capabilities afforded by the present invention advantageously permit reduced dosages, due to more efficient delivery of active antibody. Significant cost savings may be achieved by using the crystallized antibodies and antibody formulations and compositions described herein.

The antibody crystals, crystal formulations and compositions of the present invention enhance preservation of the native biologically active tertiary structure of the whole antibodies and create a reservoir which can slowly release active whole antibodies, or fragments thereof, to a subject where and when they are needed. The biologically active whole antibody, or fragment thereof, is subsequently released in a controlled manner over a period of time, as determined by the particular encapsulation technique, polymer constitution, crystal morphology, crystal size, crystal solubility, and the presence and nature of any excipients used. The crystals, crystal formulations and compositions of this invention may be reconstituted with a diluent for the parenteral administration of biologically active whole antibodies or antibody fragments.

Formulations and compositions comprising crystals of a whole antibody, or fragments thereof, in polymeric delivery carriers according to this invention may also comprise any conventional carrier or adjuvant used in vaccines, pharmaceuticals, personal care formulations and compositions, veterinary preparations, or oral enzyme supplementation. These carriers and adjuvants include, for example, Freund's adjuvant, ion exchangers, alumina, aluminum stearate, lecithin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, sodium chloride, zinc salts, colloidal silica, magnesium, trisilicate, cellulose-based substances and polyethylene glycol. Adjuvants for topical or gel base forms may include, for example, sodium carboxymethylcellulose, polyacrylates, polyoxyethylene-polyoxypropylene-block polymers, polyethylene glycol and wood wax alcohols.

According to one embodiment of this invention, crystals of an whole antibody or crystals of a single-chain Fv antibody fragment or crystals of an Fab antibody fragment may be combined with any conventional materials used for controlled release administration, including pharmaceutical controlled release administration. Such materials include, for example, coatings, shells and films, such as enteric coatings and polymer coatings and films.

Formulations or compositions comprising crystals of an whole antibody or crystals of a single-chain Fv antibody fragment or crystals of an Fab antibody fragment may be delivered to humans, animals, or plants at the desired site of delivery according to this invention. Such delivery may include the use of devices, such as implant-capable devices, or may involve other microparticulate protein delivery systems.

In one embodiment of this invention, crystals of an whole antibody or of a single-chain Fv antibody fragment or of an Fab antibody fragment have a longest dimension between about 0.01 µm and about 500 µm, alternatively between about 0.1 µm and about 200 µm. The most preferred embodiment is that the whole antibody crystals, or crystals of an antibody fragment, are between about 1 µm and about 100 µm in their longest dimension. Such crystals may have a shape selected from the group consisting of: needles, needle clusters, disks, cubes, rods, quasi-crystals, spheres, plates, such as hexagons and squares, rhomboids, bipyramids and prisms, and others.

In one embodiment of this invention, formulations or compositions have a whole antibody concentration greater than about 0.1 mg/ml or a single-chain Fv antibody fragment concentration greater than about 0.1 mg/ml, or an Fab antibody fragment concentration greater than about 0.1 mg/ml. Alternatively, formulations or compositions have a whole antibody concentration greater than about 1 mg/ml or a single-chain Fv antibody fragment concentration greater than about 1 mg/ml, or an Fab antibody fragment concentration greater than about 1 mg/ml. Alternatively, formulations or compositions of the present invention have a whole antibody concentration greater than about 10 mg/ml or a single-chain Fv antibody fragment concentration greater than about 10 mg/ml, or an Fab antibody fragment concentration greater than about 10 mg/ml. Alternatively, formulations or compositions of the present invention have a whole antibody concentration greater than about 20 mg/ml or a single-chain Fv antibody fragment concentration greater than about 20 mg/ml, or an Fab antibody fragment concentration greater than about 20 mg/ml. Alternatively, formulations or compositions of the present invention have a whole antibody concentration greater than about 50 mg/ml or a single-chain Fv antibody fragment concentration greater than about 50 mg/ml, or an Fab antibody fragment concentration greater than about 50 mg/ml. Alternatively, formulations or compositions of the present invention have a whole antibody concentration greater than about 100 mg/ml or a single-chain Fv antibody fragment concentration greater than about 100 mg/ml, or an Fab antibody fragment concentration greater than about 100 mg/ml. Alternatively, formulations or compositions of the present invention have a whole antibody concentration greater than about 120 mg/ml or a single-chain Fv antibody fragment concentration greater than about 120 mg/ml, or an Fab antibody fragment concentration greater than about 120 mg/ml. Alternatively, formulations or compositions of the present invention have a whole antibody concentration greater than about 200 mg/ml or a single-chain Fv antibody fragment concentration greater than about 200 mg/ml, or an Fab antibody fragment concentration greater than about 200 mg/ml.

According to this invention, any individual, including humans, animals and plants, may be treated in a pharmaceutically acceptable manner with a pharmaceutically effective amount of crystals of a whole antibody or crystals of a single-chain Fv antibody fragment or crystals of an Fab antibody fragment, or formulations or compositions comprising such crystals, for a period of time sufficient to treat a condition in the individual to whom they are administered over some period of time. Alternatively, individuals may receive a prophylactically effective amount of whole antibody crystals or crystals of a single-chain Fv antibody fragment or crystals of an Fab antibody fragment, or formulations or compositions comprising such crystals, of this invention which is effective to prevent a condition in the individual to whom they are administered over some period of time.

Crystals of a whole antibody or crystals of a single-chain Fv antibody fragment or crystals of an Fab antibody fragment, or formulations or compositions comprising such crystals, may be administered alone, as part of a pharmaceutical, personal care or veterinary preparation, or as part of a prophylactic preparation, with or without adjuvant. They may be administered by parenteral or oral routes. For example, they may be administered by oral, pulmonary, nasal, aural, anal, dermal, ocular, intravenous, intramuscular, intraarterial, intraperitoneal, mucosal, sublingual, subcutaneous, transdermal, topical or intracranial routes, or into the buccal cavity. In either pharmaceutical, personal care or veterinary applications, crystals of whole antibodies or fragments thereof, or crystal formulations or compositions thereof may be topically administered to any epithelial surface. Such epithelial surfaces include oral, ocular, aural, anal and nasal surfaces, which may be treated, protected, repaired or detoxified by application of crystals of a whole antibody, crystals of a single-chain Fv antibody fragment, or crystals of an Fab antibody fragment, or crystal formulations or compositions thereof.

Pharmaceutical, veterinary or prophylactic preparations comprising crystals of a whole antibody or crystals of a single-chain Fv antibody fragment, or crystals of an Fab antibody fragment, or formulations or compositions comprising such crystals, according to this invention may also be selected from the group consisting of tablets, liposomes, granules, spheres, microparticles, microspheres and capsules.

For such uses, as well as other uses according to this invention, crystals of a whole antibody or crystals of a single-chain Fv antibody fragment or crystals of an Fab antibody fragment, or formulations or compositions comprising such crystals, may be prepared in tablet form. Such tablets constitute a liquid-free, dust-free form for storage of whole antibody crystals, crystals of antibody fragments, or crystal formulations or compositions which are easily handled and retain acceptable levels of activity or potency.

Alternatively, crystals of a whole antibody or crystals of a single-chain Fv antibody fragment or crystals of an Fab antibody fragment, or formulations or compositions comprising such crystals, may be in a variety of conventional forms employed for administration to provide reactive whole antibodies or single-chain Fv antibody fragments or Fab antibody fragments at the site where needed. These include, for example, solid, semi-solid and liquid dosage forms, such as liquid solutions or suspensions, slurries, gels, creams, balms, emulsions, lotions, powders, sprays, foams, pastes, ointments, salves, balms and drops.

Crystals of a whole antibody or crystals of a single-chain Fv antibody fragment or crystals of an Fab antibody fragment, or formulations or compositions comprising such crystals, according to this invention may also comprise any conventional carrier or adjuvant used in pharmaceuticals, personal care preparations or veterinary preparations. These carriers and adjuvants include, for example, Freund's adjuvant, ion exchangers, alumina, aluminum stearate, lecithin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, sodium chloride, zinc salts, colloidal silica, magnesium, trisilicate, cellulose-based substances and polyethylene glycol. Adjuvants for topical or gel base forms may include, for example, sodium carboxymethylcellulose, polyacrylates, polyoxyethylene-polyoxypropylene-block polymers, polyethylene glycol and wood wax alcohols.

The most effective mode of administration and dosage regimen of crystals of a whole antibody or crystals of a single-chain Fv antibody fragment or crystals of an Fab antibody fragment, or formulations or compositions comprising such crystals, of this invention will depend on the effect desired, previous therapy, if any, the individual's health status, the status of the condition itself, the response to the whole antibody crystals or single-chain Fv antibody fragment crystals or Fab antibody fragment crystals, or crystal formulations or compositions thereof, and the judgment of the treating physician or clinician. The whole antibody crystals, single-chain Fv antibody fragment crystals, Fab antibody fragment crystals, or crystal formulations or compositions thereof, may be administered in any dosage form acceptable for pharmaceuticals, immunotherapy, or veterinary preparations, at one time or over a series of treatments.

The amount of crystals of a whole antibody or crystals of a single-chain Fv antibody fragment or crystals of an Fab antibody fragment, or formulations or compositions comprising such crystals, which provides a single dosage will vary depending upon the particular mode of administration, the specific crystal preparation, formulation or composition, dose level and dose frequency. A typical preparation will contain between about 0.01% and about 99%, preferably between about 1% and about 50%, of whole antibody crystals or crystals of a single-chain Fv antibody fragment or crystals of an Fab antibody fragment, or formulations or compositions thereof (w/w). Alternatively, a preparation will contain between about 0.01% and about 80% whole antibody crystals or crystals of a single-chain Fv antibody fragment or crystals of an Fab antibody fragment, or formulations or compositions thereof (w/w), preferably between about 1% and about 50%, antibody crystals or crystals of a single-chain Fv antibody fragment or crystals of an Fab antibody fragment, or formulations or compositions thereof (w/w).

Upon improvement of the individual's condition, a maintenance dose of crystals of a whole antibody or crystals of a single-chain Fv antibody fragment or crystals of an Fab antibody fragment, or formulations or compositions comprising such crystals, may be administered, if necessary. Subsequently, the dosage or frequency of administration, or both, may be reduced as a function of the symptoms, to a level at which the improved condition is retained. When the condition has been alleviated to the desired level, treatment should cease. Individuals may, however, require intermittent treatment on a long-term basis upon any recurrence of the condition or symptoms thereof.

The crystallized whole antibodies, single-chain Fv antibody fragments and Fab antibody fragments, and compositions and formulations thereof, according to this invention, may be used to treat a wide variety of human and other diseases, infections and disorders including, inter alia, any human diseases which can be treated with antibodies, alone or in combination with other drugs, or in complex or conjugated with other chemical substances, e.g., toxins or radionucleotides. Diseases, infections and disorders which may be treated or diagnosed using the crystallized whole antibodies, scfv antibody fragments and Fab antibody fragments, and compositions and formulations thereof, according to this invention, include, inter alia: AIDS/HIV infection or related conditions; autoimmune disorders like rheumatoid arthritis, systemic lupus erythematosus, idiopathic thrombocytopenic purpura; blood disorders like platelet aggregation; cancer, including, inter alia, colorectal, lung and prostate cancers; digestive disorders, such as colitis, Crohn's disease and inflammatory bowel disease; eye conditions, e.g., uveitis, cataracts; heart disease, e.g., acute myocardial, cardiovascular thrombosis; infectious diseases, e.g., sepsis, osteomyelitis; neurologic disorders, e.g., multiple sclerosis, stroke; respiratory diseases, e.g., allergic asthma, allergic rhinitis; skin disorders, e.g., psoriasis; transplantation problems, e.g., graft-versus-host disease, organ transplant rejection; reduction in sensitivity allergens, e.g., peanuts, and injuries resulting trauma etc.

In another embodiment, the crystallized whole antibodies, scFv antibody fragments and Fab antibody fragments, and compositions and formulations thereof, according to this invention, may be used alone or in test kits to diagnose diseases or infections including, inter alia, osteomyelitis, salmonellosis, shigellosis, and the location and extent of disease staging in cancers such as non-Hodgkin's lymphoma and leukemia.

In yet another embodiment, the crystallized whole antibodies, scFv antibody fragments and Fab antibody fragments, and compositions and formulations thereof, according to this invention, may be used as in vivo imaging agents for the detection of diseases such as cardiovascular thrombosis.

The antibodies that may be crystallized and used according to this invention include, but are not limited to: anti-cytokine antibodies, anti-CD antigen antibodies (anti-CD3,-CD20 (e.g., Rituximab), anti-CD25, anti-CD52, anti-CD33, anti-CD11a), anti-TNF-$\alpha$(e.g., Infliximab), anti-rattlesnake venom, anti-ICAM (e.g., anti-ICAM-1, anti-ICAM-3), anti-growth factor antibodies (e.g., anti-VEGF), anti-growth factor receptor antibodies (e.g., anti-HER2/neu (e.g., Trastuzumab), anti-EGFR), anti-immunoglobulin antibodies (e.g., anti-IgE), anti-polyclonal Ab antibodies, anti-viral antibodies (e.g., anti-CMV, anti-HIV (e.g., anti-gp120), anti-HBV, anti-RSV (e.g., anti-F glycoprotein)), etc.), anti-complement antibodies (e.g., anti-C5), anti-clotting factor antibodies (e.g., anti-gpIIb/IIIa, anti-Factor VII), anti-interleukin antibodies (e.g., anti-IL-5, anti-IL-4, anti-IL-8), antibodies targeted to the Major Histocompatability Complex (e.g., anti-HLA), anti-idiotypic antibodies, anti-integrin antibodies (e.g., anti-$\beta$-2-integrin), anti-17-IA cell surface antigen, anti-$\alpha 4\beta 7$, anti-VLA-4, and anti-CBL.

Those of skill in the art will appreciate that antibody fragments including, inter alia, Fv and Fab antibody fragments of the above-mentioned whole antibodies may also be crystallized and used according to this invention.

Production of Crystals of a Whole Antibody or Crystals of a Single-Chain Fv Antibody Fragment, or Crystals of an Fab Antibody Fragment, or Formulations or Compositions Comprising Such Crystals According to the one embodiment of this invention, crystals of a whole antibody, crystals of a single-chain Fv antibody fragment, crystals of an Fab antibody fragment, or formulations or compositions comprising such crystals are prepared by the following process.

First, the whole antibody or single-chain Fv antibody fragment or Fab antibody fragment is crystallized. Next, excipients or ingredients selected from sugars, sugar alcohols, viscosity increasing agents, wetting or solubilizing agents, buffer salts, emulsifying agents, antimicrobial agents, antioxidants, and coating agents are added directly to the mother liquor. Alternatively, the mother liquor is removed, after which the crystals are suspended in an excipient solution for a minimum of 1 hour to a maximum of 24 hours. The excipient concentration is typically between about 0.01 and about 10% (w/w). The ingredient concentration is between about 0.01 and about 90% (w/w). The crystal concentration is between about 0.01 and about 99% (w/w).

The mother liquor is then removed from the crystal slurry either by filtration or by centrifugation. Subsequently, the crystals are washed optionally with solutions of about 50 to 100% (w/w) of one or more organic solvents such as, for example, ethanol, methanol, isopropanol or ethyl acetate, either at room temperature or at temperatures between $-20°$ C. to $25°$ C.

The crystals are then dried either by passing a stream of nitrogen, air, or inert gas over them. Alternatively, the crystals are dried by air drying, spray drying, lyophilization or vacuum drying. The drying is carried out for a minimum of about 1 hour to a maximum of about 72 hours after washing, until the moisture content of the final product is below about 10% by weight, most preferably below about 5% by weight. Finally, micromizing (reducing the size) of the crystals can be performed if necessary.

According to one embodiment of this invention, when preparing crystals of a whole antibody, or crystals of a single-chain Fv antibody fragment, or crystals of an Fab antibody fragment, or formulations or compositions comprising such crystals, enhancers, such as surfactants, are not added during crystallization. Excipients or ingredients are added to the mother liquor after crystallization, at a concentration of between about 1 and about 10% (w/w), alternatively at a concentration of between about 0.1 and about 25% (w/w), alternatively at a concentration of between about 0.1 and about 50% (w/w). The excipient or ingredient is incubated with the crystals in the mother liquor for about 0.1 to about 3 hrs, alternatively the incubation is carried out for about 0.1 to about 12 hrs, alternatively the incubation is carried out for about 0.1 to about 24 hrs.

In another embodiment of this invention, the ingredient or excipient is dissolved in a solution other than the mother liquor, and the crystals are removed from the mother liquor and suspended in the excipient or ingredient solution. The ingredient or excipient concentrations and the incubation times are the same as those described above.

The present invention may also utilize other slow release methodologies, such as silicon based rings or rods which have been preloaded with encapsulated crystals of a whole antibody or crystals of a single-chain Fv antibody fragment, or crystals of an Fab antibody fragment, or formulations or compositions comprising them, and can therefore act as implants for delivery. Such methodologies provide a constant level of antibodies or antibody fragments to the bloodstream over a period of weeks or months. Such implants can be inserted intradermally and can be safely replaced and removed when needed.

Other formulations and compositions according to this invention include vaccine formulations and compositions comprising crystals of a whole antibody, or crystals of a single-chain Fv antibody fragment or crystals of an Fab antibody fragment, and adjuvant and/or encapsulating polymer(s). In one embodiment of this invention, a whole anti-idiotypic antibody is itself the immunogen. In this embodiment, the whole antibody crystals and crystal formulations or compositions would elicit a response to the antigen that the anti-idiotype mimics or is closely related to. Therefore, the anti-idiotypic antibody can act as a type of vaccine or therapy against cancers and autoimmune diseases, e.g., allergies, as well as viruses, for example, hepatitis B virus.

One embodiment of such vaccine formulations or compositions involves a single vaccine injection containing microspheres comprising crystalline whole antibodies, or scFv fragments or Fab fragments thereof. Those microspheres would, for example, be characterized by three or more different release profiles. In this way, crystals of a whole antibody, or fragment thereof, that act like antigens may be released over a sustained period sufficient to generate lasting immunity. By virtue of such a formulation or composition, multiple antigen boosts may be made available in single unit form. One advantage of such a system is that by using whole antibody crystals, crystals of single-chain Fv antibody fragments, or crystals of Fab antibody fragments, or formulations or compositions comprising such crystals, the native three-dimensional structures of the antibodies or antibody fragments are maintained and presented to the immune system in their native form, thus eliciting the immune response seen with native antibodies.

Once the immune system is primed, there may be less need for an adjuvant effect. Therefore, in the slower degrading inoculations, a less immunogenic adjuvant may be included and possibly no adjuvant may be required in the slowest degrading microspheres of the formulations and compositions. In this way, patient populations in remote areas would not have to be treated multiple times in order to provide protection against infectious diseases.

Another advantage of the present invention is that crystals of a whole antibody or crystals of a single-chain Fv antibody fragment, or crystals of an Fab antibody fragment, or formulations thereof, that are encapsulated within polymeric carriers to form compositions comprising microspheres can be dried by lyophilization. Lyophilization, or freeze-drying allows water to be separated from the composition. The antibody crystal composition is first frozen and then placed in a high vacuum. In a vacuum, the crystalline $H_2O$ sublimes, leaving the whole antibody crystal or antibody fragment crystal composition behind, containing only the tightly bound water. Such processing further stabilizes the composition and allows for easier storage and transportation at typically encountered ambient temperatures.

Spray drying allows water to be separated from the crystal preparation. It is highly suited for the continuous production of dry solids in either powder, granulate or agglomerate form from liquid feedstocks as solutions, emulsions, and pumpable suspensions. Spray drying involves the atomization of a liquid feedstock into a spray of droplets and contacting the droplets with hot air in a drying chamber. The sprays are produced by either rotary (wheel) or nozzle atomizers. Evaporation of moisture from the droplets and formation of dry particles proceed under controlled temperature and airflow conditions. Relatively high temperatures are needed for spray drying operations. However, heat damage to products is generally only slight, because of an evaporative cooling effect during the critical drying period and because the subsequent time of exposure to high temperatures of the dry material may be very short. Powder is discharged continuously from the drying chamber. Operating conditions and dryer design are selected according to the drying characteristics of the product and the powder specification. Spray drying is an ideal process where the end product must comply with precise quality standards regarding particle size distribution, residual moisture content, bulk density and particle shape.

This feature is especially desirable for therapeutic antibodies and anti-idiotypic vaccines, which can be dispensed into single dose sterile containers ("ampules") or, alternatively, any desired increment of a single dose as a slurry, in a formulation or a composition. The ampules containing the dispensed slurries, formulations or compositions can then be capped, batch frozen and lyophilized under sterile conditions. Such sterile containers can be transported throughout the world and stored at ambient temperatures. Such a system is useful for providing sterile vaccines and therapeutic antibodies to remote and undeveloped parts of the world. At the point of use, the ampule is rehydrated with the sterile solvent or buffer of choice and dispensed. For such preparations, minimal or no refrigeration is required.

In another embodiment of this invention, crystals of a whole antibody, or crystals of a single-chain Fv antibody fragment, or crystals of an Fab antibody fragment, according to this invention may be crosslinked for additional stability. This is advantageous for the use of such crystals, crystal formulations and compositions in areas of pH extremes, such as the gastrointestinal tract of humans and animals. For example, antibody crystals, such as, monoclonal antibody crystals, may be crosslinked using one of a variety of crosslinkers, including, but not limited to, Dimethyl 3,3'-dithiobispropionimidate.HCl (DTBP), Dithiobis (succinimidylpropionate) (DSP), Bis maleimido-hexane (BMH), Bis [Sulfosuccinimidyl]suberate (BS), 1,5-Difluoro-2,4-dinitrobenzene (DFDNB), Dimethylsuberimidate.2HCl (DMS), Disuccinimidyl glutarate (DSG), Disulfosuccinimidyl tartarate (Sulfo-DST), 1-Ethyl-3-[3-Dimethylaminopropyl]carbodiimide hydrochloride (EDC), Ethylene glycolbis[sulfosuccinimidylsuccinate] (Sulfo-EGS), N-[g-maleimidobutyryloxy]succinimide ester (GMBS), N-hydroxysulfosuccinimidyl-4-azidobenzoate (Sulfo-HSAB), Sulfosuccinimidyl-6-[a-methyl-a-(2-pyridyldithio) toluamido] hexanoate (Sulfo-LC—SMPT), Bis-[b-(4-azidosalicylamido) ethyl]disulfide (BASED) and glutaraldehyde (GA).

In a further embodiment of this invention, crystals of a whole antibody or scFv fragment of an antibody or Fab fragment of an antibody may be radiolabelled to be used in antibody radiation therapies. In such a therapy, for example, a radiolabelled anti-cancer antibody crystal or scFv fragment crystal or Fab antibody fragment crystal, or formulation or composition comprising such crystals, can be delivered according to this invention, to the site of the cancer. After delivery, the released antibody or scFv fragment or Fab antibody fragment binds to its targeted cancer antigen and delivers the radioisotope directly to the cancerous cells or tumor. The release of the antibody may be timed according to this invention. Alternatively, when using crosslinked crystals in radiation therapy, the crosslinkers themselves may be radiolabeled. In this embodiment, the whole antibody, Fv antibody fragment or Fab antibody fragment that is in the crosslinked crystal serves to target and deliver the radioisotope to the cancerous cell or tumor. The radioisotope itself is carried and released by the crosslinker. Theoretically, useful radiolabels include, but are not limited to, the following radioisotopes or radionucleotides: $^3H$, $^{14}C$, $^{15}N$, $^{35}N$, $^{90}Y$, $^{99}Tc$, $^{111}In$, $^{125}I$, $^{131}I$. Practically, however, in vivo use in radiotherapies would limit the radiolabel to $^{131}I$, $^{90}Y$, or any other radiolabels defined by a short half-life. For example, the monoclonal antibody Rituximab (see Example 1) has been labeled with $^{90}Yttrium$ ($^{90}Y$), in order to be used for radioimmunotherapy in patients with non-Hodgkin's lymphomas. This compound is commercially available as Ibritumomab tiuxetan (Zevalin™) (IDEC Pharmaceuticals, (San Diego, Calif.).

Batch Crystallization of Crystals of a Whole Antibody or Crystals of a Single-Chain Fv Antibody Fragment or Crystals of an Fab Antibody Fragment Protein crystals are grown by controlled crystallization of protein from aqueous solutions or aqueous solutions containing organic solvents. Solution conditions that may be controlled include, for example, the rate of evaporation of solvent, organic solvents, the presence of appropriate co-solutes and buffers, pH and temperature. A comprehensive review of the various factors affecting the crystallization of proteins has been published by McPherson, A., *Methods Enzymol.* 114: 112-20 (1985).

Large-batch (industrial-scale) crystallization typically involves a much greater range of conditions than does crystallization by the classical "hanging drop" method. The initial protein concentration ranges between about 1 and about 200 mg/ml (or possibly even more), more preferably from about 0.01 mg/ml to about 500 mg/ml, for large batch crystallization, while the protein concentration for the hanging drop method is limited to about 4 to about 10 mg/ml (in rare cases, up to about 25 mg/ml). A further embodiment of this invention is a crystal of a whole antibody, or an Fab or scFv antibody fragment thereof, wherein said crystal is crystallized using a protein concentration that is within a range from about 0.01 mg/ml up to and including about 3.9 mg/ml. A further embodiment of this invention is a crystal of a whole antibody, or an Fab or scFv antibody fragment thereof, wherein said crystal is crystallized using a protein concentration that is within a range from about 4 mg/ml up to and including about 10 mg/ml. A further embodiment of this invention is a crystal of a whole antibody, or an Fab or scFv antibody fragment thereof, wherein said crystal is crystallized using a protein concentration that is within a range from about 10.1 mg/ml up to and including about 25 mg/ml. A further embodiment of this invention is a crystal of a whole antibody, or an Fab or scFv antibody fragment thereof, wherein said crystal is crystallized using a protein concentration that is within a range from about 25.1 mg/ml up to and including about 200 mg/ml. A further embodiment of this invention is a crystal of a whole antibody, or an Fab or scFv antibody fragment thereof, wherein said crystal is crystallized using a protein concentration that is within a range from about 200.1 mg/ml up to about 500 mg/ml.

The crystallization buffers used for large-batch crystallization can have a pH range of about 3 to about 10, more preferably a pH range from about pH 1.9 to about pH 11.1, while the hanging drop method is carried out at a pH range of about 5.0 to about 9.0 (though usually this is accomplished at a pH at or around about 7.0). A further embodiment of this invention is a crystal of a whole antibody, or an Fab or scFv antibody fragment thereof, wherein said crystal is crystallized within a pH range that is from greater than about pH 1.9 up to and including about pH 2.9. A further embodiment of this invention is a crystal of a whole antibody, or an Fab or scFv antibody fragment thereof, wherein said crystal is crystallized within a pH range from greater than about pH 2.9 up to and including about pH 3.9. A further embodiment of this invention is a crystal of a whole antibody, or an Fab or scFv antibody fragment thereof, wherein said crystal is crystallized within a pH range from greater than about pH 3.9 up to and including about pH 4.9. A further embodiment of this invention is a crystal of a whole antibody, or an Fab or scFv antibody fragment thereof, wherein said crystal is crystallized within a pH range from greater than about pH 4.9 up to and including about pH 5.9. A further embodiment of this invention is a crystal of a whole antibody, or an Fab or scFv antibody fragment thereof, wherein said crystal is crystallized within a pH range from greater than about pH 5.9 up to and including about pH 7.9. A further embodiment of this invention is a crystal of a whole antibody, or an Fab or scFv antibody fragment thereof, wherein said crystal is crystallized within a pH range from greater than about pH 7.9 up to and including about pH 8.9. A further embodiment of this invention is a crystal of a whole antibody, or an Fab or scFv antibody fragment thereof, wherein said crystal is crystallized within a pH range from greater than about pH 8.9 up to and including about pH 9.9. A further embodiment of this invention is a crystal of a whole antibody, or an Fab or scFv antibody fragment thereof, wherein said crystal is crystallized within a pH range from greater than about pH 9.9 up to and including about pH 11.1.

Large-batch crystallization can be accomplished at temperatures that range from about 4° C. to about 37° C., more preferably temperatures that range from about −21° C. up to about +61° C., while most hanging drop crystallization is carried out at temperatures from about 4° C. up to room temperature (about 22° C.). A further embodiment of this invention is a crystal of a whole antibody, or an Fab or scFv antibody fragment thereof, wherein said crystal is crystallized within a temperature range from about −210° C. up to below about 4° C. A further embodiment of this invention is a crystal of a whole antibody, or an Fab or scFv antibody fragment thereof, wherein said crystal is crystallized within a temperature range from about 4° C. up to and including room temperature (about 22° C.). A further embodiment of this invention is a crystal of a whole antibody, or an Fab or scFv antibody fragment thereof, wherein said crystal is crystallized within a temperature range from above room temperature (about 22° C.) up to and including about 37° C. A further embodiment of this invention is a crystal of a whole antibody, or an Fab or scFv antibody fragment thereof, wherein said crystal is crystallized within a temperature range from above about 37° C. up to about 61° C.

A range of about 5% to about 40% polyethylene glycol (PEG), more preferably a PEG concentration from about 2% to about 80%, with a PEG size (chain length, i.e., number of ethylene glycol residues in the PEG chain) of about 200 to about 20,000, more preferably a PEG size (chain length) of about 200 to about 40,000, more preferably a PEG size (chain length) of about 200 to about 80,000, can be used in the crystallization buffers for large-batch crystallization. Theoretically, hanging drop methods can also use these sizes and concentrations of PEG, but normally conditions will not go outside a range of about 5% to about 20% PEG 400 (size (chain length)) to PEG 10000 (size (chain length)). A further embodiment of this invention is a crystal of a whole antibody, or an Fab or scFv antibody fragment thereof, wherein said crystal is crystallized using a PEG concentration that is within a range from about 2% up to about 4.9%. A further embodiment of this invention is a crystal of a whole antibody, or an Fab or scFv antibody fragment thereof, wherein said crystal is crystallized using a PEG concentration that is within a range from about 5% up to and including about 20%. A further embodiment of this invention is a crystal of a whole antibody, or an Fab or scFv antibody fragment thereof, wherein said crystal is crystallized using a PEG concentration that is within a range from about 20.1% up to and including about 80%. A further embodiment of this invention is a crystal of a whole antibody, or an Fab or scFv antibody fragment thereof, wherein said crystal is crystallized using a PEG size (chain length) that is within a range from about 200 up to about 400. A further embodiment of this invention is a crystal of a whole antibody, or an Fab or scFv antibody fragment thereof, wherein said crystal is crystallized using a PEG size (chain length) that is within a range from about 400 up to and including about 10,000. A further embodiment of this invention is a crystal of a whole antibody, or an Fab or scFv antibody fragment thereof, wherein said crystal is crystallized using a PEG size (chain length) that is within a range from greater than about 10,000 up to and including about 80,000.

Large-batch crystallization can be accomplished at buffer concentrations that range from 0 mM (no buffer) to about 4 M, while most hanging drop crystallization is carried out at buffer concentrations from about 2 mM to about 1 M.

Large-batch crystallization can be accomplished at metal or non-metal ion concentrations that range from about 0 mM (no buffer) to about 4 M. Examples of metal and non-metal ions include, inter alia, calcium, magnesium, manganese, copper, zinc, lithium, ammonium, iron, cobalt, cesium, cadmium, nickel, sodium and potassium.

Large-batch crystallization can be accomplished at salt concentrations that range from about 0 mM (no buffer) to about 4 M. Examples of suitable salts include, inter alia, chloride, acetate, sulfate, phosphate, nitrate, citrate, Tris, HEPES, cacodylate, imidazole, CHES, CAPS, MES, MOPS, tartarate, borate, carbonate/bicarbonate, fluoride, iodide, thiocyanate, formate, malonate, succinic acid, bicine and EDTA.

It will be understood by those of skill in the art that the crystallization methods according to this invention can be accomplished using a wide variety of reagents, under a wide variety of crystallization conditions, including but not limited to: crystallization in the presence of various divalent or monovalent ions; crystallization in the presence of concentrations of divalent metal ions ranging from about 5 mM to about 500 mM; crystallization using various buffer salts including, but not limited to acetate, borate, carbonate, succinate, imidazole, Tris, HEPES, MOPs, Phosphate, CHES, and other biological buffers mentioned in the Sigma catalogue; crystallization using reagents including, inter alia, PEG monomethyl ether, MPD, ethoxyethanol, propanediol, organic solvents, sodium or potassium salts like sulfite (including other sodium salts), ammonium salts, lithium salts, PEG derivatives, or any other organic compounds; crystallization methods that are stationary or involve tumbling or mixing; crystallization in the presence or absence of detergents or chelators.

Crystals are obtained in large-batch crystallization in about 3 hours to about 72 hours maximum, more preferably in about 5 minutes to about 48 hours, while hanging drop methods can take days, weeks, or even months to yield crystals. Furthermore, large-batch crystallization uses an agitation step, unlike hanging drop protocols.

Large-batch crystallization is performed as follows: a suitable volume of the antibody or scFv fragment or Fab antibody fragment to be crystallized (in its storage buffer) is mixed with an equal volume of a crystallization solution or crystallization buffer (at a prescribed pH). The mixture can either be seeded with crushed crystals that were previously obtained (through other experiments) or used without seeding. The mixture is then tumbled, for example, in a hematology/chemistry mixer for about 3 to about 48 hours at the desired temperature (typically about room temperature).

Large-batch crystallization may or may not involve the use of "seed" crystals, i.e., crystals obtained during small-scale crystallization screens for the determination of crystallization conditions. Typically, seed crystals can be obtained from hanging-drop methods using commercially-available crystallization screening kits (e.g., Wizard I and Wizard II, and Cryo I and Cryo II kits (Emerald BioStructures, Inc. (Bainbridge Island, Wash.)), or Crystal Screen and Crystal Screen II kits (Hampton Research (Laguna Niguel, Calif.). Alternatively, crystals of a whole antibody or scFv fragment or Fab antibody fragment may be prepared using a screening method, called microbatch screening, which is, in practice, a scaled down version of the large-batch crystallization method described above. [1]

Although crystallization of whole antibodies has been a subject of significant interest for approximately the last twenty-five years, very few have been crystallized [Harris L. J., Skaletsky, E., and McPherson, A., *J. Mol. Biol.* 275:861-72 (1998); Harris L. J., Larson, S. B., Skaletsky, E., and McPherson, A. *Immunological Reviews* 163:35-43 (1998)]. Such prior efforts utilized solely hanging drop or seeding drop protocols. Both methods were characterized by extremely low yields of crystals and, therefore, were unsuitable for large-scale production of antibody crystals. Such was the case because of difficulties in antibody crystallization due to their large size, the presence of surface oligosaccharides, and their high degree of segmental flexibility. Crystallization of whole antibodies on a large scale, a process offering an alternative route of delivery for the therapeutic antibodies, has never been explored before.

Encapsulation of Crystals of A Whole Antibody or a Single-Chain Fv Antibody Fragment or a Fab Antibody Fragment in Polymeric Carriers According to one embodiment of this invention, compositions are produced when whole antibody crystals or crystals of a single-chain Fv antibody fragment, or crystals of an Fab antibody fragment, or formulations comprising such crystals, are encapsulated in at least one polymeric carrier to form microspheres by virtue of encapsulation within the matrix of the polymeric carrier to preserve their native and biologically active tertiary structure. The crystals can be encapsulated using various biocompatible and/or biodegradable polymers having unique properties which are suitable for delivery to different biological environments or for effecting specific functions. The rate of dissolution and, therefore, delivery of active antibodies or fragments thereof is determined by the particular encapsulation technique, polymer preparation, polymer crosslinking, polymer thickness, polymer solubility, and antibody crystal geometry.

Crystals of a whole antibody or crystals of a single-chain Fv antibody fragment or crystals of an Fab antibody fragment, or formulations of such crystals, to be encapsulated are suspended in a polymeric carrier which is dissolved in an organic solvent. The polymer solution must be concentrated enough to completely coat the antibody crystals or formulations after they are added to the solution. Such an amount is one which provides a weight ratio of antibody crystals to polymer between about 0.02 and about 20, preferably between about 0.1 and about 2. The antibody crystals are contacted with polymer in solution for a period of time between about 0.5 minutes and about 30 minutes, preferably between about 1 minute and about 3 minutes. The crystals should be kept suspended and not allowed to aggregate as they are coated by contact with the polymer.

Following that contact, the crystals become coated and are referred to as nascent microspheres. The nascent microspheres increase in size during the coating process. In a preferred embodiment of the invention, the suspended coated crystals or nascent microspheres along with the polymeric carrier and organic solvent are transferred to a larger volume of an aqueous solution containing a surface active agent, known as an emulsifier. In the aqueous solution, the suspended nascent microspheres are immersed in the aqueous phase, where the organic solvent evaporates or diffuses away from the polymer. Eventually, a point is reached where the polymer is no longer soluble and forms a precipitated phase encapsulating the antibody crystals, antibody fragment crystals, or formulations to form a composition. This aspect of the process is referred to as hardening of the polymeric carrier or polymer. The emulsifier helps to reduce the interfacial surface tension between the various phases of matter in the system during the hardening phase of the process. Alternatively, if the coating polymer has some inherent surface activity, there may be no need for addition of a separate surface active agent.

Emulsifiers useful to prepare encapsulated crystals of a whole antibody or crystals of a single-chain Fv antibody fragment or crystals of an Fab antibody fragment according to this invention include poly(vinyl alcohol) as exemplified herein, surfactants and other surface active agents which can reduce the surface tension between the polymer coated whole antibody crystals or polymer coated crystal formulations and the solution.

In a preferred embodiment of this invention, crystallinity of the whole antibody crystals or crystals of a single-chain Fv antibody fragment or crystals of an Fab antibody fragment is maintained during the encapsulation process. The crystallinity is maintained during the coating process by using an organic solvent in which the crystals are not soluble. Subsequently, once the coated crystals are transferred to the aqueous solvent, rapid hardening of the polymeric carrier and sufficient coating of the crystals in the previous step shields the crystalline material from dissolution.

The polymers used as polymeric carriers to coat the whole antibody crystals or crystals of a single-chain Fv antibody fragment or crystals of an Fab antibody fragment can be either homo-polymers or co-polymers. The rate of hydrolysis of the microspheres is largely determined by the hydrolysis rate of the individual polymer species. In general, the rate of hydrolysis decreases as follows: polycarbonates>polyesters>polyurethanes>polyorthoesters>polyamides. For a review of biodegradable and biocompatible polymers, see W. R. Gombotz and D. K. Pettit, "Biodegradable polymers for protein and peptide drug delivery", Bioconjugate Chemistry, vol. 6, pp. 332-351 (1995).

In a preferred embodiment of this invention, the polymeric carrier comprises a single polymer type, such as PLGA. In a next preferred embodiment, the polymeric carrier can be a mixture of polymers, such as 50% PLGA and 50% albumin.

Other polymers useful as polymeric carriers to prepare encapsulated crystals of a whole antibody or crystals of a single-chain Fv antibody fragment or crystals of an Fab antibody fragment according to this invention include biocompatible/biodegradable polymers selected from the group consisting of poly (acrylic acid), poly (cyanoacrylates), poly (amino acids), poly (anhydrides), poly (depsipeptide), poly (esters), such as poly (lactic acid) or PLA, poly (b-hydroxybutryate), poly (caprolactone) and poly (dioxanone); poly (ethylene glycol), poly (hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, starch and its derivatives, collagen, fibrin, gelatin, hyaluronic acid, oligosaccharides, glycaminoglycans, sulfated polysaccharides, blends and copolymers thereof. Other useful polymers are described in J. Heller and R. W. Balar, "Theory and Practice of Controlled Drug Delivery from Biodegradable Polymers," Academic Press, New York, NY, (1980); K. O. R. Lehman and D. K. Dreher, Pharmaceutical Technology, vol. 3 (1979); E. M. Ramadan, A. El-Helw and Y. El-Said, Journal of Microencapsulation, vol. 4, pp. 125-132 (1987); 0. Phillai and R. Panchagnula, Current Opinion in Chemical Biology, vol. 5, pp. 447-451 (2001). The preferred polymer will depend upon the particular antibody crystals or antibody fragment crystals used and the intended use of the encapsulated crystals or crystal formulations. Alternatively, the solvent evaporation technique may be used for encapsulating whole antibody crystals or antibody fragment crystals (see D. Babay, A. Hoffmann and S. Benita, Biomaterials vol. 9, pp. 482-488 (1988)).

In a preferred embodiment of this invention, crystals of a whole antibody or crystals of a single-chain Fv antibody fragment or crystals of an Fab antibody fragment are encapsulated in at least one polymeric carrier using a double emulsion method, as illustrated herein, using a polymer, such as polylactic-co-glycolyic acid. In a most preferred embodiment of this invention, the polymer is Polylactic-co-glycolyic acid ("PLGA"). PLGA is a co-polymer prepared by polycondensation reactions with lactic acid ("L") and glycolic acid ("G"). Various ratios of L and G can be used to modulate the crystallinity and hydrophobicity of the PLGA polymer. Higher crystallinity of the polymer results in slower dissolution. PLGA polymers with 20-70% G content tend to be amorphous solids, while high level of either G or L result in good polymer crystallinity. See D. K. Gilding and A. M. Reed, "Biodegradable polymers for use in surgery-poly(glycolic)/poly(lactic acid) homo and copolymers: 1., Polymer vol. 20, pp. 1459-1464 (1981). PLGA degrades after exposure to water by hydrolysis of the ester bond linkage to yield non-toxic monomers of lactic acid and glycolic acid.

Another embodiment of this invention includes double-walled polymer coated microspheres. Double-walled polymer coated microspheres may be produced by preparing two separate polymer solutions in methylene chloride or other solvent which can dissolve the polymers. The whole antibody crystals or crystals of a single-chain Fv antibody fragment or crystals of an Fab antibody fragment are added to one of the solutions and dispersed. Here, the crystals become coated with the first polymer. Then, the solution containing the first polymer coated crystals is combined with the second polymer solution. [See Pekarek, K. J.; Jacob, J. S. and Mathiowitz, E. Double-walled polymer microspheres for controlled drug release, Nature, 367, 258-260]. As a result, the second polymer encapsulates the first polymer which is encapsulating the crystal. Ideally, this solution is then dripped into a larger volume of an aqueous solution containing a surface active agent or emulsifier. In the aqueous solution, the solvent evaporates from the two polymer solutions and the polymers are precipitated.

Whole antibodies and single-chain Fv antibody fragments and Fab antibody fragments recovered by dissolving crystals, formulations or compositions according to this invention may be characterized for secondary structure. Such whole antibody crystals or crystals of a single-chain Fv antibody fragment or crystals of an Fab antibody fragment may also be characterized by β-sheet structural content, as indicated by a correlation spectra as compared to the spectra of the soluble antibody or antibody fragment counterpart determined by Fourier transform infrared (FTIR) spectra that is between about 0.8 and about 1.0. A correlation coefficient of less than about 0.8 indicates an protein sample that has become denatured to such en extent that its intermolecular β-sheet secondary structure content has increased, resulting in protein aggregation and precipitation.

In order that this invention may be better understood, the following examples are set forth. These examples are for the purpose of illustration only and are not to be construed as limiting the scope of the invention in any manner.

EXAMPLES

In the following examples, the crystal screening kits used (when seeding from hanging drops) were one or more of the following: Wizard I and Wizard II, and Cryo I and Cryo II kits (Emerald BioStructures, Inc. (Bainbridge Island, Wash.), or Crystal Screen and Crystal Screen II kits (Hampton Research (Laguna Niguel, Calif.). Batch crystallization or microbatch screening of whole antibodies was carried out by mixing the antibody with the appropriate crystallization buffer, followed by tumbling or incubation (with or without shaking as noted). Antibody crystals, which were obtained from vapor diffusion hanging drops in preliminary screening or from microbatch screening, were used in most cases, to facilitate the crystallization process. Antibody crystals were confirmed by determining their birefringence.

Example 1

Rituximab

Rituximab is a chimeric murine/human monoclonal antibody commercially available as Rituxan™ (Genentech, Inc., South San Francisco, Calif.). This monoclonal antibody has been widely used to treat non-Hodgkins lymphoma. Rituximab is a chimeric IgG1 kappa immunoglobulin that binds to the CD20 antigen on the surface of normal and malignant B-lymphocytes. It is composed of murine light- and heavy-chain variable region sequences and a human constant region sequence. The Rituximab antibody has an approximate molecular weight (MW) of 145 kD.

Rituximab Crystallization, Batch 1:
Materials:
A—Rituximab antibody (stored until use at 4° C., at 10 mg/ml in 9.0 mg/ml sodium chloride, 7.35 mg/ml sodium citrate anhydrate, 0.7 mg/ml Polysorbate 80 and sterile water, pH 6.5)
B—Wizard I crystal screening kit (Emerald BioStructures, Bainbridge Island, Wash.)
C—Polyethylene glycol-1000 (PEG-1000)
D—Imidazole
E—Calcium acetate buffer pH 8.0
Procedure:
Rituximab seed crystals were obtained from vapor diffusion drops in a preliminary screening using the Wizard I screening kit. Microbatch crystallization was carried out using 500 µl of a crystallization buffer containing 20% (w/v) PEG-1000, 100 mM imidazole, and 200 mM calcium acetate, pH 8.0. After seeding with Rituximab seed crystals from the hanging drops, the mixture was tumbled in a hematology/chemistry mixer (Model 346, Fisher Scientific, Pittsburgh, Pa.) at 50 rpm at room temperature overnight. The antibody crystals obtained from this step were used as seeds for large-batch crystallization, which is, in essence, a scaled-up microbatch procedure. Large-batch crystallization was initiated by mixing 8 ml of the Rituximab solution with 8 ml of a crystallization buffer containing 20% (w/v) PEG-1000, 100 mM imidazole, and 200 mM calcium acetate, pH 8.0. The final concentration of the Rituximab in solution was 5 mg/ml. After seeding with Rituximab seed crystals from the microbatch, the mixture was tumbled in a hematology/chemistry mixer (Model 346, Fisher Scientific) at room temperature at 50 rpm. After overnight tumbling, Rituximab crystals in the form of needle clusters were formed. 85% of the input Rituximab was crystallized in this example.

Example 2

Rituximab Crystallization, Batch 2:
Rituximab crystals were obtained as in Example 1, except that crystallization was initiated by mixing 500 µl of Rituximab (10 mg/ml) with an equal volume of crystallization buffer containing 20% (w/v) PEG-1000, 100 mM imidazole, and 200 mM calcium acetate, pH 7.0. After seeding with Rituximab seed crystals from a microbatch, the mixture was tumbled in a hematology/chemistry mixer (Model 346, Fisher Scientific) at room temperature at 50 rpm. After overnight tumbling, Rituximab crystals in the form of needle clusters were formed. This protocol has been repeated, at pH 4.0, 5.0, 6.0 and 8.0, with similar results.

Example 3

Microbatch Crystallization Screening of Rituximab:
Rituximab crystals were obtained as in Example 1, except that crystallization was initiated by mixing 60 µl of Rituximab (10 mg/ml) with an equal volume of crystallization buffer containing 20% (w/v) PEG-600, 100 mM calcium acetate, and 50 mM 2-[N-cyclohexylamino] ethanesulfonic acid (CHES), pH 9.5. The final concentration of the Rituximab in solution was 5 mg/ml. After seeding with Rituximab seed crystals from a previously obtained microbatch, the mixture was incubated in a benchtop shaker/incubator (New Brunswick Scientific, Model C25), at 25° C. at 650 rpm. After overnight incubation, Rituximab crystals in the form of needle clusters (FIG. 1) were formed. 80% of the input Rituximab was crystallized in this example.

Example 4

Microbatch Crystallization Screening of Rituximab:
Rituximab crystals were obtained as in Example 1, except that crystallization was initiated by mixing 50 μl of Rituximab (10 mg/ml) with an equal volume of crystallization solution containing 20% (w/v) PEG-1000 and 100 mM calcium acetate. The mixture was allowed to sit at room temperature for 12 hours. After seeding with Rituximab seed crystals from a previously obtained microbatch, the mixture was allowed to continue incubating at room temperature in Eppendorf centrifuge tubes. After overnight incubation, Rituximab crystals in the form of needle clusters were formed. This screen was repeated, with the calcium acetate concentration being adjusted to 10, 20, 40, 60, 80, 200 or 400 mM, with crystals being obtained under all conditions tested.

Example 5

Microbatch Crystallization Screening of Rituximab:
Rituximab crystals were obtained as in Example 1, except that crystallization was initiated by mixing 50 μl of Rituximab (10 mg/ml) with an equal volume of crystallization solution containing 25% (w/v) PEG-1000 and 100 mM calcium acetate. The mixture was allowed to sit at room temperature for 12 hours. After seeding with Rituximab seed crystals from a previously obtained microbatch, the mixture was allowed to continue incubating at room temperature in centrifuge tubes. After overnight incubation, Rituximab crystals in the form of needle clusters were formed. This screen was repeated, with the PEG-1000 concentration being adjusted to 5, 10, 15, 20 or 40% (w/v), with crystals being obtained under all conditions being tested.

Example 6

Microbatch Crystallization Screening of Rituximab:
Rituximab crystals were obtained as in Example 1, except that crystallization was initiated by mixing 50 μl of Rituximab (10 mg/ml) with an equal volume of crystallization buffer containing 20% (w/v) PEG-6000, 100 mM calcium acetate and 100 mM Tris, pH 8.0. After seeding with Rituximab seed crystals from a previously obtained microbatch, the mixture was incubated in a benchtop shaker/incubator (New Brunswick Scientific, Model C25), at 25° C. at 225 rpm. After overnight incubation, Rituximab crystals in the form of needle clusters were formed. This example was repeated, by substituting PEG-2000, PEG-4000 or PEG-8000 for the PEG-6000 (maintaining the PEG concentration at 20%), with crystals being obtained under all conditions being tested. See FIG. 1.

Example 7

Microbatch Crystallization Screening of Rituximab:
Rituximab crystals were obtained as in Example 1, except that crystallization was initiated by mixing 60 μl of Rituximab (10 mg/ml) with an equal volume of crystallization buffer containing 20% (w/v) PEG-6000, 100 mM calcium acetate and 100 mM Tris, pH 7.0. After seeding with Rituximab seed crystals from a previously obtained microbatch, the mixture was incubated in a benchtop shaker/incubator (New Brunswick Scientific, Model C25), at 25° C. at 650 rpm. After overnight incubation, Rituximab crystals in the form of needle clusters were formed. This screen was repeated, by substituting PEG-200, PEG-300 or PEG-20000 for PEG-6000 (maintaining the PEG concentration at 20%). 140 mM (instead of 100 mM) Tris was used for the screens using PEG-200. Crystals being obtained under all conditions tested.

Example 8

Microbatch Crystallization Screening of Rituximab:
Rituximab crystals were obtained as in Example 1, except that crystallization was initiated by mixing 50 μl of Rituximab (10 mg/ml) with an equal volume of crystallization buffer containing 20% (w/v) PEG-1000 and 200 mM $CuSO_4$, and 100 mM imidazole, pH 8.0. After sitting at room temperature for 14 hours, the mixture was seeded with Rituximab seed crystals from a previously obtained microbatch and incubated at room temperature. After overnight incubation, Rituximab crystals in the form of rods were formed. Subsequently, this screen was repeated, by substituting other divalent cations, e.g., 200 mM $CaCl_2$, $MnCl_2$, or $ZnCl_2$ for the 200 mM $CuSO_4$, with crystals in the form of needle clusters, disks and quasi crystals being obtained.

Example 9

Rituximab Crystallization Using Dialyzed Rituximab
An aliquot of 4 ml of Rituximab (10 mg/ml) was dialyzed against 2 liters of deionized water overnight at 4° C., with two changes of deionized water before being concentrated to 1 ml with a centrifugal filter device (Millipore, 30 kD cut-off). Crystallization was carried out in hanging drops by mixing 6 μl of concentrated Rituximab with 2 μl of crystallization buffer containing 20% (w/v) PEG-1000 and 100 mM imidazole, 200 mM calcium acetate, pH 8.0, on a glass cover slide. The cover slide was flipped over and placed onto a well, which contained 450 μl of the same buffer, in a 24-well plate. After incubation of the plate at room temperature for approximately one week, Rituximab crystals in the form of cubes were formed.

Example 10

Rituximab Crystallization Using Dialyzed Rituximab
An aliquot of 5 ml of Rituximab (10 mg/ml) was dialyzed against 2 liters of 10 mM Hepes buffer, pH 7.0, overnight at 4° C., before being concentrated to 54 mg/ml with a centrifugal filter device (Millipore, 10 kD cut-off). Batch crystallization was carried out by mixing 20 μl of concentrated Rituximab with buffer and additives, so that the final mixture contained 36 mg/ml antibody, 133 mM Hepes, pH 7.50, 66 mM $CaCl_2$ and 13% 2-methyl-2,4,-pentanediol. The mixture was tumbled in a hematology/chemistry mixer (Model 346, Fisher Scientific) at room temperature at 50 rpm. After a 48 hour incubation at room temperature, Rituximab crystals in the form of needle clusters were formed. In this example, 84% of the input Rituximab was crystallized.

Example 11

Rituximab Crystallization Using Dialyzed Rituximab
An aliquot of 5 ml of Rituximab (10 mg/ml) was dialyzed against 2 liters of 10 mM Hepes buffer, pH 7.0, overnight at 4° C., before being concentrated to 54 mg/ml with a centrifugal filter device (Millipore, 10kD cut-off). Batch crystallization was carried out by mixing 20 μl of concentrated Rituximab with buffer and additives, so that the final mixture contained 18 mg/ml antibody, 200 mM Hepes, pH 7.50, 200 mM CaCl$_2$ and 33% PEG-400. The mixture was tumbled in a hematology/chemistry mixer (Model 346, Fisher Scientific) at room temperature at 50 rpm. After a 48 hour incubation, Rituximab crystals in the form of needle clusters were formed.

Example 12

Rituximab Crystallization:

Rituximab (10 mg/ml) was crystallized by mixing 80 μl of antibody with 20 μl of 0.02 M CaCl$_2$, 0.1 M sodium acetate, pH 4.6, 30% 2-methyl-2,4-pentanediol and tumbling the mixture in a hematology/chemistry mixer (Model 346, Fisher Scientific) at room temperature at 50 rpm. After a 48 hour incubation at room temperature, Rituximab crystals in the form of needle clusters were formed.

Example 13

Rituximab Crystallization in the Presence of a Detergent:

Rituximab was crystallized by mixing 450 μl of Rituximab with an equal volume of a crystallization buffer containing 20% (w/v) PEG-1000, 100 mM imidazole, 200 mM calcium acetate, pH 8.0, and 0.1% Tween®80 (a detergent) (Sigma-Aldrich). After seeding with Rituximab seed crystals from a previously obtained microbatch, the mixture was tumbled in a hematology/chemistry mixer (Model 346, Fisher Scientific) at 50 rpm at room temperature. Crystals, in the form of needle clusters, were formed after overnight tumbling. Rituximab was also crystallized using starting volumes ranging between 50 μl and 1.0 ml. The same type of crystals formed.

Example 14

Rituximab Crystallization:

Rituximab (10 mg/ml) was crystallized by mixing 50 μl of antibody with 50 μl of 0.2 M calcium acetate, 0.1 M sodium acetate, pH 4.6, 30% PEG 400. After seeding with Rituximab seed crystals from a previously obtained microbatch, the mixture was tumbled in a hematology/chemistry mixer (Model 346, Fisher Scientific) at room temperature at 225 rpm. After a 24 hour incubation at room temperature, Rituximab crystals in the form of needle clusters were formed.

Example 15

Rituximab Crystallization:

Rituximab (10 mg/ml) was crystallized by mixing 50 μl of antibody with 50 μl of 0.2 M calcium acetate, 0.1 M imidazole, pH 8.0, 10% PEG 8000. After seeding with Rituximab seed crystals from a previously obtained microbatch, the mixture was tumbled in a hematology/chemistry mixer (Model 346, Fisher Scientific) at room temperature at 225 rpm. After a 24 hour incubation at room temperature, Rituximab crystals in the form of needle clusters were formed.

Example 16

Rituximab Crystallization:

Rituximab (10 mg/ml) was crystallized by mixing 50 μl of antibody with 50 μl of 0.2 M calcium acetate, 0.1 M Tris, pH 7.0, 20% PEG 3000. After seeding with Rituximab seed crystals from a previously obtained microbatch, the mixture was tumbled in a hematology/chemistry mixer (Model 346, Fisher Scientific) at room temperature at 225 rpm. After a 24 hour incubation at room temperature, Rituximab crystals in the form of needle clusters were formed.

Example 17

Rituximab Crystallization:

Rituximab (10 mg/ml) was crystallized by mixing 50 μl of antibody with 50 μl of 0.2 M calcium acetate, 0.1 M MES, pH 6.0, 20% PEG 8000. After seeding with Rituximab seed crystals from a previously obtained microbatch, the mixture was tumbled in a hematology/chemistry mixer (Model 346, Fisher Scientific) at room temperature at 225 rpm. After a 24 hour incubation at room temperature, Rituximab crystals in the form of needle clusters were formed.

Example 18

Rituximab Crystallization:

Rituximab (10 mg/ml) was crystallized by mixing 50 μl of antibody with 50 μl of 0.05 M calcium acetate, 0.1 M imidazole, pH 8.0, 35% 2-ethoxyethanol. After seeding with Rituximab seed crystals from a previously obtained microbatch, the mixture was tumbled in a hematology/chemistry mixer (Model 346, Fisher Scientific) at room temperature at 225 rpm. After a 24 hour incubation at room temperature, Rituximab crystals in the form of needle clusters were formed.

Example 19

Rituximab Crystallization:

Rituximab (10 mg/ml) was crystallized by mixing 50 μl of antibody with 50 μl of 0.05 M calcium acetate, 0.1 M acetate, pH 4.5, 40% 1,2-propanediol. After seeding with Rituximab seed crystals from a previously obtained microbatch, the mixture was tumbled in a hematology/chemistry mixer (Model 346, Fisher Scientific) at room temperature at 225 rpm. After a 24 hour incubation at room temperature, Rituximab crystals in the form of needle clusters were formed.

Example 20

Rituximab Crystallization:

Rituximab (10 mg/ml) was crystallized by mixing 50 μl of antibody with 50 μl of 0.2 M calcium acetate, 0.1 M HEPES, pH 7.5, 40% PEG 400. After seeding with Rituximab seed crystals from a previously obtained microbatch, the mixture was tumbled in a hematology/chemistry mixer (Model 346, Fisher Scientific) at room temperature at 225 rpm. After a 24 hour incubation at room temperature, Rituximab crystals in the form of needle clusters were formed.

Example 21

Rituximab Crystallization:

Rituximab (10 mg/ml) was crystallized by mixing 4 ml antibody with 4 ml reagent containing 0.2 M calcium acetate, 0.1 M TRIS, pH 7.0, 20% PEG 6000 and 0.1% Tween®80 (Sigma-Aldrich). After seeding with Rituximab seed crystals from a previously obtained microbatch, the mixture was tumbled in a hematology/chemistry mixer (Model 346, Fisher Scientific) at room temperature at 50 rpm. After a 24 hour incubation at room temperature, Rituximab crystals in the form of needle clusters were formed. The yield was 93% by this method.

Example 22

Rituximab Crystallization:

Rituximab (10 mg/ml) was crystallized by mixing 1 ml antibody with 1 ml reagent containing 0.2 M calcium acetate, 0.1 M MES, pH 6.0, 20% PEG 6000 and 0.1% Tween®80 (Sigma-Aldrich). After seeding with Rituximab seed crystals from a previously obtained microbatch, the mixture was tumbled in a hematology/chemistry mixer (Model 346, Fisher Scientific) at room temperature at 50 rpm. After a 24 hour incubation at room temperature, Rituximab crystals in the form of needle clusters were formed. The yield was 80% by this method.

Example 23

Rituximab Crystallization:

Dialyzed Rituximab (10 mg/ml) was crystallized by mixing 10 μl of antibody with 10 μl of 0.2 M calcium acetate, 0.1 M sodium acetate, pH 4.6, 30% 2-propanol. After seeding with Rituximab seed crystals from a previously obtained microbatch, the mixture was tumbled in a hematology/chemistry mixer (Model 346, Fisher Scientific) at room temperature at 225 rpm. After a 24 hour incubation at room temperature, Rituximab crystals in the form of needle clusters were formed.

Example 24

Rituximab Crystallization:

Dialyzed Rituximab (10 mg/ml) was crystallized by mixing 10 μl of antibody with 20 μl of 0.02 M $CaCl_{21}$ 0.1 M sodium acetate, pH 4.6, 30% 2-methyl-2,4-pentanediol. After seeding with Rituximab seed crystals from a previously obtained microbatch, the mixture was tumbled in a hematology/chemistry mixer (Model 346, Fisher Scientific) at room temperature at 225 rpm. After a 24 hour incubation at room temperature, Rituximab crystals in the form of needle clusters were formed.

Example 25

Rituximab Crystallization:

Dialyzed Rituximab (10 mg/ml) was crystallized by mixing 10 μl of antibody with 20 μl of 0.2 M $CaCl_{21}$ 0.1 M HEPES, pH 7.5, 28% PEG 400. After seeding with Rituximab seed crystals from a previously obtained microbatch, the mixture was tumbled in a hematology/chemistry mixer (Model 346, Fisher Scientific) at room temperature at 225 rpm. After a 24 hour incubation at room temperature, Rituximab crystals in the form of needle clusters were formed.

Example 26

Rituximab Crystallization—Different Crystal Form:

Rituximab (20 mg/ml) was crystallized by mixing 10 μl of antibody with 10 μl of solution containing 15% PEG 400, 0.51 M sodium sulfate, 0.1 M EDTA. The final concentration of the Rituximab in solution was 10.0 mg/ml. After seeding with Rituximab seed crystals from a previously obtained hanging drop, the mixture was tumbled in a hematology/chemistry mixer (Model 346, Fisher Scientific) at room temperature at 225 rpm. After a 24 hour incubation at room temperature, Rituximab crystals in the form of small needles were formed. In this example, 87% of the input Rituximab was crystallized. See FIG. 4.

Example 27

Rituximab Crystallization—Different Crystal Form:

Rituximab (20 mg/ml) was crystallized by mixing 10 μl of antibody with 10 μl of solution containing 12% PEG 400 and 1.36 M sodium sulfate and 0.1 M Tris, pH 7.5. After seeding with Rituximab seed crystals from a previously obtained microbatch, the mixture was tumbled in a hematology/chemistry mixer (Model 346, Fisher Scientific) at room temperature at 225 rpm. After a 24 hour incubation at room temperature, Rituximab crystals in the form of small needles were formed.

Example 28

Rituximab Crystallization—Different Crystal Form:

Dialyzed Rituximab (66 mg/ml) was crystallized by mixing 10 μl of antibody with 20 μl of solution containing of 0.2 M $CaCl_{21}$ 0.1 M HEPES, pH 7.5, 28% PEG 400. After 20 days, additional amounts of PEG 400 (30 μl 100% PEG 400) and 10 μl of 1M lithium sulfate were added. After a 24 hour incubation at room temperature, Rituximab crystals in the form of cubes were formed. (FIG. 3).

Example 29

Morphology of the Crystals #1

Different forms of Rituximab were obtained by using different crystallization conditions.

For example, see Rituximab crystals from FIGS. 1 and 3.

Example 30

Morphology of the Crystals #2

Crystallization:

Buffer: 100 mM Hepes, pH 7.7, 12% PEG 400, 1.17 M sodium sulfate.

Method: 1 volume Rituximab was mixed with 2 volumes crystallization buffer. The mixture was maintained at room temperature without agitation until crystals formed.

Result: Small (length $\leq 10$ μm) needle-like crystals formed. (FIG. 4).

Example 31

Trastuzumab

Trastuzumab is a recombinant DNA-derived humanized monoclonal antibody commercially available as Herceptin™ (Genentech, Inc., South San Francisco, Calif.). This monoclonal antibody has been widely used to treat breast cancer which over-expresses the extracellular domain of the epidermal growth factor receptor 2 protein, HER2. Trastuzumab is an IgG1 kappa that contains human framework regions with the complementarity-determining regions of a murine antibody (4D5) that binds to HER2.

Trastuzumab Microbatch Crystallization, Batch 1:

Trastuzumab antibody was stored in its original 440 mg vial as a sterile lyophilized powder and was subsequently dissolved in 20 ml of sterile water. The dissolved Trastuzumab solution, containing 22 mg/ml Trastuzumab, 9.9 mg L-histidine HCl, 6.4 mg L-histidine, 400 mg α,α-trehalose dihydrate, and 1.8 mg polysorbate 20, USP.

A 210 μl aliquot of Trastuzumab (22 mg/ml), in a buffer containing 0.495 mg/ml L-histidine HCl, 0.32 mg/ml L-histidine, 20 mg/ml α,α-trehalose dihydrate, and 0.09 mg/ml polysorbate 20, USP, was mixed with 210 μl of crystallization buffer containing 25% PEG 400, 5% PEG 8000, 100 mM Tris, pH 8.5, 10% propylene glycol, and 0.1% Tween®80 (Sigma-Aldrich) and incubated at room temperature overnight. The final concentration of the Trastuzumab in solution was 11 mg/ml. This mixture was then seeded with Trastuzumab crystals obtained from hanging drop and tumbled at 50 rpm in a Hematology/Chemistry mixer (Model 346, Fisher Scientific) after being supplemented with 20 µl of propylene glycol. Trastuzumab crystals were obtained on the following day. (FIG. 5). 85% of the input Trastuzumab was crystallized by this method.

Example 32

Trastuzumab Microbatch Crystallization, Batch 2:

50 µl of Trastuzumab (22 mg/ml) in a buffering solution containing 0.495 mg/ml L-histidine HCl, 0.32 mg/ml L-histidine, 20 mg/ml α,α-trehalose dihydrate, and 0.09 mg/ml polysorbate 20, USP, was mixed with 50 µl of crystallization buffer containing 20% PEG 300, 10% glyercol, 0.1 M Tris, pH 7, 10% PEG 8000 and incubated at room temperature overnight after being seeded with Trastuzumab crystals obtained from microbatch. Trastuzumab crystals with a size ranging from 50-120 µm were obtained on the following day. (FIG. 6).

Example 33

Trastuzumab Microbatch Crystallization, Batch 3:

50 µl of Trastuzumab (22 mg/ml), in a buffer containing 0.495 mg/ml L-histidine HCl, 0.32 mg/ml L-histidine, 20 mg/ml α,α-trehalose dihydrate, and 0.09 mg/ml polysorbate 20, USP, was mixed with 50 µl of crystallization buffer containing 20% PEG 300, 10% glyercol, 0.1 M Tris, pH 7, 10% PEG 8000 and incubated at room temperature overnight after being seeded with Trastuzumab crystals obtained from microbatch. Trastuzumab crystals with a size of about 20 µm were obtained on the following day.

Example 34

Infliximab

Infliximab is a chimeric murine/human monoclonal antibody commercially available as Remicade™ (Centocor, Leiden, the Netherlands). This monoclonal antibody has been widely used to treat rheumatoid arthritis and Crohn's disease. Infliximab is a chimeric IgG1 kappa immunoglobulin that binds to the TNF-A antigen. It is composed of murine light- and heavy-chain variable region sequences and a human constant region sequence. The Infliximab antibody has an approximate molecular weight (MW) of 149 kD.

Infliximab Microbatch Crystallization, Batch 1:

Infliximab antibody was stored in its original 100 mg vial as a sterile lyophilized powder and was subsequently dissolved in 2 ml of sterile water. The dissolved solution, containing 100 mg Infliximab, 500 mg sucrose, 0.5 mg polysorbate 80, 2.2 mg monobasic sodium phosphate, and 6.1 mg dibasic sodium phosphate, was used for crystallization.

Infliximab was crystallized by mixing 50 µl of antibody (50 mg/ml) with 100 µl of 35% ethoxyethanol, 0.2 M lithium sulfate, 0.1 M Tris, pH 8.6. The mixture was tumbled in a hematology/chemistry mixer (Model 346, Fisher Scientific) at room temperature at 50 rpm. After overnight incubation, Infliximab crystals in the form of rod shaped clusters were formed (FIG. 2).

Example 35

Infliximab Microbatch Crystallization, Batch 2:

Rod shaped crystals similar to those of Example 34 were also obtained when Infliximab was incubated (without agitation) with 40% (w/v) PEG-400, 0.1 M Tris buffer, 200 mM lithium sulfate, pH 8.5, under the same conditions.

Example 36

Infliximab Microbatch Crystallization, batch 3:

A 25 µl aliquot of Infliximab (50 mg/ml in 0.1M Tris HCl buffer, pH7.0) was mixed with 3 µl of 1M calcium chloride and 5 µl of 100% polyethylene glycol monomethyl ether 550 (PEG MME 550) and incubated (without agitation) overnight at room temperature. Cube shaped crystals of Infliximab formed overnight.

Example 37

Infliximab Microbatch Crystallization

A 25 µl aliquot of Infliximab (20 mg/ml in water) was mixed with 50 µl of crystallization buffer containing 20% PEG 300, 0.1 M TRIS, pH 8.5 5% PEG 8000 and 10% glycerol. The final concentration of the Infliximab in solution was 6.7 mg/ml. This mixture was then incubated (without agitation) overnight at room temperature. Star shaped crystals of Infliximab formed after a week. (FIG. 7).

Example 38

The crystallization conditions exemplified above are useful for the crystallization of any desirable clinically relevant antibody. Clinically relevant antibodies may be classified according to the therapeutic area in which they are to be employed. Such antibodies include, but are not limited to, commercially available antibodies, including, but not limited to:

(1) Abciximab (ReoPro™) (anti-GPIIB/IIIa receptor; for the treatment of cardiovascular disease) (Centocor, Leiden, The Netherlands);
(2) Palivizumab (Synagis™) (anti-F protein on RSV; respiratory disease) (manufactured by MedImmune (Gaithersburg, Md.);
(3) Murumonab-CD3 (Orthoclone™) (anti-CD3 antibody; for tissue transplant rejection) (OrthoBiotech, Raritan, N.J.);
(4) Gemtuzumab ozogamicin (Mylotarg™) (cancer (anti-CD33 antibody)) (Wyeth Labs, Philadelphia, Pa.);
(5) Trastuzumab (Herceptin™) (cancer (anti-HER2 antibody)) (Genentech, South San Francisco, Calif.);
(6) Basiliximab (Simulect™) (anti-CD25 antibody; for tissue transplant rejection) (Novartis, Basel, Switzerland);
(7) Daclizumab (Zenapax™) (anti-CD25 antibody; for tissue transplant rejection) (Protein Design Labs, Fremont, Calif.);
(8) Etanercept (ENBREL™) (inflammatory disease) (Immunex, Seattle, Wash.);
(9) Ibritumomab tiuxetan (Zevalin™) (radioimmunotherapy for cancer) (IDEC Pharmaceuticals, San Diego, Calif.).

Example 39

The crystallization conditions exemplified above are useful for the crystallization of single-chain Fv (scFv) fragments of antibodies, or for crystallization of Fab fragments of antibodies.

Example 40

Other Classes of Immunoglobulin

All embodiments of this invention are useful for crystallization of, and use of crystals of, all of the immunoglobulin classes IgG, IgM, IgA, IgD, IgE, and serum IgA (sIgA) as well as the subclasses IgG1, IgG2, IgG3 and IgG4, IgM1 and IgM2, and IgA1 and IgA2.

Example 41

Crystallization as a Tool for Monoclonal Antibody Purification

Monoclonal antibodies including, inter alia, Rituximab, Infliximab and Trastuzumab may be obtained from mammalian cell culture. Crystallization of these monoclonal antibodies may be carried out either directly from the culture media or cell extract or after partial or complete purification. Crystallization may be used as a purification method during these steps.

In a similar fashion, monoclonal antibodies can be purified using crystallization from other sources including, inter alia, the following: insect cell culture; bacterial cell culture; plant parts including, inter alia, seeds, flowers, leaves and roots/tubers from transgenic plants, including, inter alia, transgenic maize, tobacco, potatoes and corn; and milk, serum, plasma, eggs, and other areas of transgenic animals, including, inter alia, transgenic cows, horses, pigs, chickens, goats and sheep.

Crystallization of antibodies may be carried out either directly from the cell extract before purification or after partial or complete purification, e.g., directly from milk or after clarification or partial purification of the protein of interest at any stage of the process.

Method:

One liter of, e.g., Trastuzumab (at 22 mg/ml) is mixed in a beaker with one liter of a crystallization buffer containing 25% PEG400, 5% PEG8000, 100 mM Tris, pH 8.5, 10% propylene glycol, and 0.1% Tween®80 (Sigma-Aldrich). The mixture is then incubated at room temperature overnight with stirring, using a overhead stirrer. The solution is then seeded with Trastuzumab crystals obtained from hanging drop or microbatches. 100 ml of propylene glycol is added and the mixture is stirred, until crystals are formed (for approximately 24 hours).

Example 42

Purification of Antibodies by Crystallization from Milk

Milk (purchased from a local farm and stored frozen at 70° C.) is thawed at 37° C. and de-fatted by centrifugation at 7000× g for 15 minutes at 4° C. The cream layer is then punctured using a sharp pipette tip and the skim milk is decanted into a clean tube through the opening. Skim milk is then diluted with an equal volume of 250 mM EDTA. The milky appearance clears, indicating the destruction of micellar structures and aggregates. EDTA-clarified skim milk is dialyzed against PBS to remove EDTA. The clarified milk may then be spiked with monoclonal antibody solutions to a final concentration of approximately 5-10 mg/ml. The monoclonal antibody from the spiked milk is then crystallized using polyethylene glycol alone or in combination with salts, e.g., ammonium sulfate, or any of the crystallization conditions described earlier using a variety of salts, buffer, organic solvents etc. This method may be used to purify antibodies from transgenic milk.

Example 43

Crystallization of Monoclonal Antibodies from Transgenic Animals, Transgenic Animal Products, and Transgenic Plants It will be understood by those of skill in the art that the method shown in Examples 41 and 42 may be use to purify monoclonal antibodies by crystallization, from transgenic animals (from cells, tissue extracts, etc.) transgenic animal products (e.g., eggs etc.) and from transgenic plants (plant cells and tissue extracts, etc.).

In Examples 44 and 45, the purity and conformation of crystallized Rituximab was assessed by analyzing dissolved Rituximab on HPLC and SDS-PAGE, under reducing and non-reducing conditions.

Example 44

Dissolved Rituximab from crystals obtained in Example 1 were analyzed on a 4-20% gradient SDS-PAGE gel, without the presence of β-mercaptoethanol. The omission of β-mercaptoethanol from the gel electrophoresis was to prevent the dissociation of the heavy and light chains, which are held together by a disulfide bond. Native Rituximab was analyzed under the same conditions as a control.

Results:

Both the native and dissolved Rituximab showed a single protein band under non-reducing conditions, with a molecular weight approximately equal to 150 kD, the correct size for the whole Rituximab monoclonal antibody.

The protocol was repeated, using reducing conditions (using β-mercaptoethanol). Native Rituximab was analyzed under the same conditions as a control.

Results:

For both native and dissolved Rituximab under reducing conditions, the gel revealed two bands at about 50 kD and about 25 kD, the correct size for the monoclonal antibody heavy and light chains, respectively.

Example 45

Purity and Size Analysis of Rituximab Crystals by HPLC

The purity and size of native Rituximab and dissolved Rituximab from crystals obtained in Example 1 were analyzed with a size exclusion column (BIOSEP-SEC S3000, Phenomenex, Torrence, Calif.) on an HPLC (Shimadzu, LC-10AD) system with 100 mM potassium phosphate, pH 7.5 as running buffer and a constant flow rate of 0.5 ml/min. Both the native and dissolved Rituximab were eluted from the column as a single protein peak, indicating that the crystallization process did not alter the structural integrity of the Rituximab antibody.

Example 46

Dynamic Light Scattering Characterization of Native (Soluble) and Dissolved Rituximab Soluble Rituximab and dissolved Rituximab from Rituximab crystals, prepared as in Example 21, were dissolved in 25 mM Tris, pH 7.0, 150 mM sodium chloride and 0.1% Tween®80 (Sigma-Aldrich) (final protein concentration equal to approximately 1 mg/ml), and analyzed on a PD2000 Dynamic Light Scattering detector with Precision/Acquire and Precision/Analyze (Precision Detectors, Franklin, Mass.). Native (soluble) Rituximab (10 mg/ml) was diluted 20-fold with deionized water for comparison.

Results:

The hydrodynamic radius for the soluble and dissolved Rituximab are identical, indicating that the crystallization process did not alter this characteristic of the Rituximab antibody. In addition, this example showed that no protein aggregation occurred during crystallization, as judged from measuring the hydrodynamic radius.

Example 47

Dynamic Light Scattering Characterization of Native (Soluble) and Dissolved Trastuzumab Trastuzumab crystals, prepared as in Example 31, were dissolved in 25 mM Tris, pH 7.0, 150 mM Sodium chloride and 0.1% Tween®80 (Sigma-Aldrich). The final protein concentration was adjusted to approximately 1 mg/ml. The dissolved Trastuzumab crystal was then analyzed on a PD2000 Dynamic Light Scattering detector with Precision/Acquire and Precision/Analyze (Precision Detectors, Franklin, Mass.). Native (soluble) Trastuzumab (22 mg/ml) was diluted 20-fold with deionized water for comparison.

Results:

The hydrodynamic radius and the molecular weight for the soluble and dissolved Trastuzumab were identical, indicating that the crystallization process did not alter this characteristic of the Trastuzumab antibody. In addition, this example showed that no protein aggregation occurred during crystallization, as judged from measuring the hydrodynamic radius.

Example 48

The needle cluster Rituximab crystals, which were crystallized in Example 1 with 20% (w/v) PEG-1000, 100 mM imidazole, and 200 mM calcium acetate, pH 7.0, were determined to have a median of 72 μm and a size range between 50-150 μm, as characterized with a Coulter LS Particle Size Analyzer.

Example 49

Peptide Mapping Comparison of Native (Soluble) and Dissolved Rituximab

A 500 ml aliquot of 10 mg/ml of Rituximab (soluble or crystals from Example 1) in 25 mM Tris, pH 7.0 and 0.1% Tween®80 (Sigma-Aldrich) was mixed with 167 μg of trypsin and incubated at 37° C. for 24 hr. Each digested sample was filtered through a 0.22 μm filter and a 200 ml aliquot was loaded onto a C-8 reverse phase (Vydac, Hesperia, Calif.) HPLC column, which was equilibrated with water supplemented with 0.1% trifluoracetic acid, on a Shimazu LC10AD system. The bound peptide was eluted with a 0-70% acetonitrile gradient over 70 min at 0.9 ml/min.

Results:

Similar profiles were obtained for soluble and redissolved Rituximab, indicating no change in conformation, structure or size of the Rituximab molecule due to the crystallization process.

Example 50

N-Terminal Sequencing of Native (Soluble) and Dissolved Rituximab and Trastuzumab:

In order to demonstrate that antibodies, e.g., Rituximab and Trastuzumab, do not suffer terminal degradation in the crystalline state, the following was performed on Rituximab and Trastuzumab crystals prepared according to Examples 21 and 31, respectively, and their soluble counterparts:

N-terminal sequencing was carried out using an Applied Biosystems, Inc. (ABI) 447A automatic protein sequencer. Each sample was loaded onto a glass fiber disc, which had been placed in the sequencer and pre-cycled once. Following the pre-cycling step, a number of cycles of Edman degradation were performed using a standard protein sequencing program from ABI. The results are reported as the major phenylthiohydantonin (PTH)-amino acid detected for each cycle. (Standard one-letter designations for the 20 commonly occurring amino acids are used to report the resulting sequences. They are: A=alanine; C=cysteine; D=aspartic acid; E=glutamic; F=phenylalanine; G=glycine; H=histidine; I=isoleucine; K=lysine; L=leucine; M=methionine; N=asparagine; P=proline; Q=glutamine; R=arginine; S=serine; T=threonine; V=valine; W=tryptophan; Y=tyrosine.)

| Results: Trastuzumab: | | |
|---|---|---|
| Trastuzumab Form | Antibody Chain | N-terminal sequence |
| Crystalline | Heavy | E-V-Q-L-V-G-S (SEQ ID NO: 1) |
| Crystalline | Light | D-I-Q-M-T-Q-S (SEQ ID NO: 2) |
| Soluble | Heavy | E-V-Q-L-V-G-S (SEQ ID NO: 1) |
| Soluble | Light | D-I-Q-M-T-Q-S (SEQ ID NO: 2) |

| Rituximab: | | |
|---|---|---|
| Rituximab Form | Anitbody Chain | N-terminal sequence |
| Crystalline | Heavy | blocked |
| Crystalline | Light | Q-I-V-L-S-Q-S (SEQ ID NO: 3) |
| Soluble | Heavy | blocked |
| Soluble | Light | Q-I-V-L-S-Q-S (SEQ ID NO: 3) |

The results show that the crystallization process does result in N-terminal amino acid degradation of the Trastuzumab or Rituximab antibodies.

Example 51

PAS (Periodic acid-Schiff Reagent) Total Carbohydrate Staining of Native (Soluble) and Dissolved Trastuzumab Method:

2 μg of a dialyzed sample of crystallized Trastuzumab, prepared according to Example 31, as well as its soluble counterpart (as supplied by the manufacturer), both reduced with 10% β-mercaptoethanol and unreduced, were run on SDS-PAGE gels. The gels were transferred via Western blot to nitrocellulose membranes. Using the BioRad Immun-Blot staining kit, the carbohydrate moieties attached to the antibodies (and the heavy chains of the antibodies in the case of the reduced samples) were stained and visualized. Specifically, the gels were fixed with 40% methanol, 7% acetic acid for 30 minutes, and washed 4 times in this solution, then left in overnight in fresh solution. The next day, gels were oxidized in 1% periodic acid, 3% acetic acid, and subsequently washed 10 times in double-distilled (dd) H₂O, 10 minutes each, to remove periodic acid. Gels were incubated in the dark with Schiff's reagent for about one hour to develop stain and then scanned.

Results:

Both soluble and crystalline Trastuzumab appeared to be nearly identical on the gel, except for the light high-molecular weight band in the non-reduced sample of crystalline antibody. In the reduced sample, the carbohydrate was associated with the heavy chain of the antibody, as expected.

Example 52

PAS (Periodic Acid-Schiff Reagent) Total Carbohydrate Staining of Native (Soluble) and Dissolved Rituximab Method:

This method was performed as in Example 51.

Results:

Soluble and crystallized samples of Rituximab appeared identical on the gel slab, with the carbohydrate associated with the heavy chain of the antibody in the reduced sample.

Example 53

N-Linked Oligosaccharide Profiling of Native (Soluble) and Dissolved Trastuzumab and Rituximab N-linked Oligosaccharide Profiling was achieved using a BioRad N-linked Oligosaccharide Profiling Kit (catalog # 170-6501). Crystallized samples of Trastuzumab and Rituximab (from Examples 31 and 21, respectively) were washed, dissolved, and dialyzed against ddH₂O, and samples of soluble Trastuzumab and Rituximab (as supplied by manufacturer) were dialyzed against ddH₂O. A 200 μg aliquot of each sample was mixed with equal volumes of releasing buffer and denatured using 1 μl 5% sodium dodecyl sulfate (SDS), 1.5 μl 10% β-ME, and 4 μl NP-40 (Tergitol at room temperature. Subsequently, 2 μl of PNGase (an enzyme that cleaves asparagine-linked oligosaccharides) was added to each sample, and samples were incubated overnight at 37° C. Protein was then precipitated with 3 volumes of cold ethanol, samples were spun, and supernatants (containing oligosaccharides) were recovered and lyophilized. Samples were reconstituted and fluorescently labeled with 8-aminonaphthalene-1,3,6-trisulfonic acid (ANTS) at 37° C. overnight. Samples were again lyophilized and reconstituted in H₂O and 2× sample buffer. oligosaccharides were run in gel electrophesis using N-linked oligosaccharide profiling gels and buffers from BioRad, and gels were visualized using a long-wave UV transilluminator.

N-Linked Oligosaccharides

N-linked oligosaccharides were cleaved from the antibodies and fluorescently stained using the BioRad N-linked Oligosaccharide Profiling Kit. The glucose ladder standard run to the left of the samples showed the relative positions of the oligosaccharides.

Results:

The bands for crystal and soluble Rituximab and Trastuzumab appeared to be identical, suggesting that crystallization causes no changes in the oligosaccharide groups associated with the starting material.

Example 54

Monosaccharide Constitution of Native (Soluble) and Dissolved Rituximab and Trastuzumab The monosaccharide constituents of native (soluble) Rituximab and Trastuzumab were compared with those of reconstituted Rituximab and Trastuzumab crystals, as prepared in Examples 1 and 31, respectively, using a Bio-Rad Monosaccharide Composition Analysis kit (catalog # 170-6811). Trastuzumab and Rituximab crystals were washed three times in mother liquor and dialyzed overnight versus ddH₂. Reconstituted native (soluble) Trastuzumab and Rituximab were dialyzed versus ddH₂O and used for comparison.

The samples of native and dissolved antibodies were then analyzed for their sugar content. Each native and dissolved antibody was divided into three 50 μl aliquots containing 40 micrograms of antibody, one aliquot each for three hydrolysis reactions. For the neutral sugar analysis, the reaction took place in 2 N trifluoracetic acid (TFA) at 100° C. over 5 hours. For amine sugars, the hydrolysis took place in 4N HCl at 100° C. over 3 hours, and sialic acid hydrolysis was performed using 0.1 N TFA at 80° C. for 1 hour. After hydrolysis, all samples were lyophilized, and the amine sugars were re-acetylated with acetic anhydride and a buffer, and lyophilized again. Samples were then reconstituted and fluorescently labeled with 2-aminoacridine (AMAC), then incubated at 45° C. for 3.5 hours. Samples were lyophilized again, diluted, and mixed with 2× sample buffer for electrophoresis. Electrophoresis of samples was accomplished using Bio-Rad Monosaccharide Composition Gels and buffers, and the results were visualized using a long-wave UV transilluminator.

Results:

Rituximab:

Native (soluble) and dissolved Rituximab had identical monosaccharide constituents. The neutral monosaccharides appearing on the gel were mannose, a small band of fucose, a small band of glucose (which could just be contamination, as it shows up in the blank) and a small band of galactose. N-glucosamine was the only band that appears after amine hydrolysis. The sialic acid hydrolysis yielded no bands.

Trastuzumab:

Native (soluble) and dissolved Trastuzumab had identical monosaccharide constituents. The neutral monosaccharides appearing on the gel were mannose, a small band of fucose, and a small band of glucose (which could just be contamination, as it shows up in the blank). N-glucosamine was the only band that appeared after amine hydrolysis. The sialic acid hydrolysis yielded no bands.

The results for both Rituximab and Trastuzumab demonstrate that the crystallization process did not alter the monosaccharide content of the antibody.

Examples 55 and 56

Antibody Bioassays

Various monoclonal antibodies which recognize tumor-associated antigens, including, inter alia, those referred to herein, are widely used for cancer treatment. The cytotoxicity of an antibody on its antigen-bearing target cells can be characterized by any one of three assays, e.g. direct cytotoxicity, complement dependent cytotoxicity (CDC), and Antibody-dependent cytotoxicity (ADCC). The target cells for Rituximab are the cells that overexpress CD-20 antigen on their surface, which include Raji, Daudi, JOK1 and WT100. The specific antigen for Trastuzumab is HER2 (human epidermal growth factor receptor 2 protein), which is overexpressed in human breast adenocarcinoma cell lines including SK-BR-3, BT474, and MCF/HER2.

1. Direct Cytotoxicity:

Direct cytotoxicity, as the name implies, measures the intrinsic toxic effect of an antibody on the target cell by co-incubating the target cells with different concentrations of antibody. Cell viability is counted after co-incubation with antibody.

2. Complement Dependent Cytotoxicity (CDC):

When an antibody binds to its cell surface antigen, it induces target cell destruction by activating the complement system (a series of interacting proteins that lyse cells and trigger local inflammatory reactions). This assay is carried out by co-incubating the fixed number of target cells with diluted human serum (as a source of compliment system) and antibody. The cell viability is determined at the end of the incubation. Compared with the control plates (target cells plus antibody only), the cell death in the plates containing complement (human serum) is significantly elevated.

3. Antibody-Dependent Cytotoxicity (ADCC):

Similar to CDC, ADCC is one of the major mechanisms responsible for cytotoxicity of monoclonal antibodies. In contrast to CDC, the target cell destruction caused by ADCC is initiated by recruiting immune cells, which specifically attack tumor cells, after an antibody binds to its specific antigen on the target cell. The ADCC assay is carried out by first seeding the wells/plates with fixed amount of target cells before co-incubated with antibody and effector immune cells (usually use the isolated peripheral blood mononuclear cells). The cell viability is determined at the end of co-incubation. Cell death is significantly increased with the presence of the effector immune cells, as compared with the control (target cell plus antibody only).

Example 55

Rituximab Crystals Induce Direct Cytotoxicity Against the RAJI Lymphoma Cell Line RAJI lymphoma cells (ATCC, Manassas, Va., ATCC # CCL 86) were cultured in growth media and diluted to 0.5× $10^5$ cells/ml. A 100 ml aliquot of that culture was transferred to one well of a 96-well plate and cultured in the presence of various concentrations of native (soluble) and dissolved Rituximab (from crystals prepared according to Example 21) for 3 days. The number of viable cells remaining after the three-day incubation was determined using CellTiter 96⁰ Aqueous One Solution Cell Proliferation Assay (Promega Corp., Madison, Wis.). (FIG. 8).

Results:

Dissolved Rituximab induced Direct Cytotoxicity as capably as native Rituximab under identical conditions.

Example 56

Rituximab Crystals Induce Complement-Dependent Cytotoxicity against RAJI Lymphoma Cells RAJI lymphoma cells (ATCC, Manassas, Va.) were cultured in growth media and diluted to 0.5× $10^5$ cells/ml. A 100 ml aliquot of above culture was transferred to one well of a 96-well plate and cultured in the presence of 25 mg/ml of native or dissolved Rituximab (from crystals prepared according to Example 21) and various concentrations of human serum for 3 days. The number of viable cells remaining after the three-day incubation was determined using CellTiter 96⁰ Aqueous One Solution Cell Proliferation Assay (Promega Corp., Madison, Wis.). (FIG. 9).

Results:

Dissolved Rituximab induced Complement-Dependent Cytotoxicity as capably as native Rituximab under identical conditions.

Example 57

Cumulative Analysis Comparing Native (Soluble) and Crystalline Rituximab

The following table summarizes Examples 44-46, 49, 50, 54, 53, 55 and 56, respectively, comparing the properties of native (soluble) and crystalline Rituximab:

| Analytical Methods | Soluable | Crystalline | Result |
|---|---|---|---|
| SDS-PAGE non-reducing conditions | Whole Ab MW = ~150 kD | Whole Ab MW = ~150 kD | Soluble and crystalline forms of Rituximab were identical. |
| reducing conditions | H chain MW = ~50 kD L chain MW = ~25 kD | H chain MW = ~50 kD L chain MW = ~25 kD | Crystallization did not alter the structural integrity of Rituximab. |
| HPLC gel filtration | Single peak | Single peak | Crystallization did not alter the structural integrity of Rituximab. |
| Dynamic Light Scattering | MW = ~150 kD | MW = ~150 kd | Crystallization did not alter the structural integrity of Rituximab or change the hydrodynamic radius. |
| Peptide mapping | Trypsin digest | Trypsin digest | Similar profiles were obtained for soluble and redissolved Rituximab, indicating no change in conformation, |

-continued

| Analytical Methods | Soluable | Crystalline | Result |
|---|---|---|---|
| | | | structure or size of the Rituximab molecule. |
| N-terminal Sequencing of Antibody Light Chains | Gln-Ile-Val-Leu-Ser-Gln-Ser (SEQ ID NO: 3) | Gln-Ile-Val-Leu-Ser-Gln-Ser (SEQ ID NO: 3) | Native (soluble) and dissolved Rituximab had identical N-terminal sequences, indicating no hydrolysis of amino acids from the N-terminal side. |
| Monosaccharide Constitution | Fucose, mannose, N-acetyl glucosamine, galactose | Fucose, mannose, N-acetyl glucosamine, galactose | Native (soluble) and dissolved crystalline Rituximab had identical monosaccharide constituents, indicating that no monosaccharides were cleaved from the monoclonal antibody during crystallization. |
| Oligosaccharide Profiling | Three bands Corresponding to G8, G9 and G10, corresponding to 8-, 9-, and 10-residue sugars. | Three bands Corresponding to G8, G9 and G10, corresponding to 8-, 9-, and 10-residue sugars. | Native (soluble) and dissolved crystalline Rituximab had identical oligosaccharide profiles, indicating that crystallization does not alter the oligosaccharide make-up of the antibody. |
| Bioassays | | | Native and dissolved |
| Direct Cytotoxicity | Yes | Yes | Rituximab both induced each function. Thus, |
| Induced Complement Dependent Cytotoxicity | Yes | Yes | crystallization did not result in changes to immune functions. |

Example 58

Secondary Structure Characterization by FTIR

The Fourier transform infrared (FTIR) spectra are collected on a Nicolet model 550 Magna series spectrometer as described by Dong et al. [Dong, A., Caughey, B., Caughey, W. S., Bhat, K. S. and Coe, J. E. Biochemistry, 1992; 31:9364-9370; Dong, A. Prestrelski, S. J., Allison, S. D. and Carpenter, J. F. *J.Pharm. Sci.*, 1995; 84: 415-424.]

For the solid samples, 1 to 2 mg of the antibody or antibody fragment are lightly ground with 350 mg of KBr powder and filled into small cups used for diffuse reflectance accessory. The spectra are collected and then processed using Grams 32 (from Galactic Software) for the determination of relative areas of the individual components of secondary structure using second derivative and curve-fitting program under amide I region (1600-1700 $cm^{-1}$).

The correlation coefficient is calculated using protein analysis software from Nicolet which easily allows the determination of the correlation coefficient between the previously saved reference spectrum and that of the current protein spectrum (Garland, B, FT-IR Studies of Protein Secondary Structure in Aqueous and Dried States. Nicolet application note # AN 9479). The second derivative spectrum of the native aqueous protein is used as a reference spectrum and the dried crystals and lyophilized solid protein can be used as samples. The proteins will have an increasingly similar secondary conformational structure as the correlation coefficient approaches unity.

Results:

The correlation coefficient for a given crystalline monoclonal antibody in slurry form, or in dried crystalline form, when compared to soluble form (reference spectrum equals to one) is greater than 0.8 but less-than-or-equal-to 1.

Example 59

Soluble Whole Antibody Sample Preparation

For comparison to the Rituximab antibody crystals produced in Example 1, a sample of soluble whole antibody was prepared by dissolving (resuspending) whole antibody crystals to 20 mg/ml in 0.1% Tween®80 (Sigma-Aldrich), 150 mM sodium chloride and 25 mM Tris-HCl, pH 7.0 at 37° C. This method was used to dissolve Rituximab crystals for Examples 44, 45, 46, 49, 50, 52, 53, 54, 55 and 56. This method was also used to dissolve Trastuzumab crystals for Examples 47, 50, 51, 53 and 54. This method was also used to dissolve Infliximab crystals for Example 63.

Example 60

Crystallinity

The crystal integrity of the crystals and formulations and compositions thereof of this invention may be measured by quantitative microscopic observations. In order to visualize whether the crystals maintained their shape after drying, dried crystals may be examined under an Olympus BX60 microscope equipped with DXC-970MD 3CCD Color Video Camera with Camera Adapter (CMA D2) with Image ProPlus software. Samples of dried crystals can be covered with a glass coverslip, mounted and examined under 10× magnification, using an Olympus microscope with an Olympus UPLAN F1 objective lens 10×/0.30 PH1 (phase contrast).

Example 61

Trastuzumab Animal Models

Trastuzumab may be used in the treatment of breast cancer [Pietras R. J., Poen J. C., Gallardo, D., Wongvipat P. N., Lee H. J. and Slamon D. J., Cancer Res, vol. 59, pp. 1347-55 (1999); Baselga, J., Norton L., Albanell J., Kim Y. M., Mendelsohn J., Cancer Research, vol. 58, pp. 2825-31 (1998).

Procedure of Tumor Formation in Nude Mice:

Human breast cancer SK-BR3 or BT-474 cells (American Type Culture Collection (ATCC) (Manassas, Va., USA)) were cultured in BRMI 1640 medium supplemented with 10% fetal bovine serum (FBS), 2 mM glutamine and 1% penicillin G/streptomycin/fungizone solution. After a few cell passages, the human breast cancer cells were inoculated subcutaneously (s.c.) ($5 \times 10^7$ cells/animal) in the hind thighs of 3-month-old female athymic mice.

Prior to inoculation, mice were primed for 10-14 days with 17β-estradiol applied s.c. in a biodegradable carrier-binder (1.7 mg of estradiol per pellet) to promote growth of the estrogen-dependent breast cancer cells. Tumor nodules were monitored by measuring their dimensions (in mm). Five to six animals were included in each treatment group. The animals were randomly chosen with respect to body weight and tumor nodule size at the start of each treatment. Antibody treatment was initiated when tumors grew to more than 50 mm³ in size in one set of animals or to more than 350 mm³ in size in a second set. Monoclonal antibodies and control solutions were administered by intra-peritoneal (i.p.) injection. Recombinant human (rhu) Mab HER-2 antibody (Trastuzumab) was given at a dose of 5 or 10 mg/kg animal body weight in three doses at 4-day intervals (over 12 days). Control injections were of human IgG1 (5 or 10 mg/kg), also given i.p., using the same administration protocol. Mice were then sacrificed for pathological examination.

The crystalline and soluble Trastuzumab eradicated most or all of the tumors formed by injecting BT 474 cells into mice, when compared to controls consisting of saline (which was used as the cell delivery vehicle) or non-specific IgG, clearly indicating that the crystalline Trastuzumab is efficacious in mice animal models for breast cancer.

Trastuzumab Pharmacokinetics (PK) Studies in Mice:

For PK studies of Trastuzumab, Trastuzumab was inoculated s.c. or i.v. into Balb/C Mice. 25 to 30 Balb/C mice of the same sex, weighing between 20 and 25 grams each, were used for the study. On day 1, mice were weighed and then given a single subcutaneous or intravenous injection of Trastuzumab (30 mg Trastuzumab per kg mouse body weight). The concentration of the Trastuzumab solution/suspension was adjusted so that the prescribed dose was administered in a volume of 5 ml per Kg mouse body weight. At 0.5, 1, 2, 4, 6, 8, 24 and 48 hours after dosing, blood samples were obtained from 3 of the mice. Three mice at each time point were anesthetized and as much blood as possible was drawn from the heart (terminal bleed) and transferred to Microtainer serum-separator tubes. About 300 µl of blood were collected from each mouse. The collected blood was allowed to clot and the tubes were centrifuged. The blood cells were removed, and the supernatant (serum) was decanted into cryo-vials and frozen at −70° C. Subsequently, Trastuzumab levels were determined by ELISA (see protocol below), and the results were plotted as the number of µg Trastuzumab per ml serum over time post-inoculation.

Trastuzumab ELISA Protocol:

Wells of 96-well high binding polystyrene plates from Sigma (Costar brand) were coated with 10 µg/ml anti-human antibody from Pierce (50 µl per well) at 4° C. overnight. The anti-human antibody was removed and the plates were washed three times with a buffer containing 50 mM Tris, pH 8.0, 0.138 M sodium chloride, 0.0027 M potassium chloride and 0.05% Tween®20 (Sigma-Aldrich) (TBST). Each well was then blocked with 200 µl of 3% non-fat dry milk (Sigma) in TBST for 2 hours at room temperature. The plates were emptied and washed 3 times with TBST. Serum samples containing Trastuzumab were diluted in non-fat dry milk in TBST. A 100 µl aliquot was added to each appropriate well. A 100 µl aliquot of control sample (either saline or IgG) was added to the appropriate wells and the plates were incubated for 2 hours at room temperature. The plates were emptied and washed 3 times with TBST. A 100 µl aliquot of Horseradish peroxidase (Sigma) (a 1/25,000 dilution) conjugated anti-human antibody (in non-fat dry milk in TBST) was then added to each well and the plates were incubated for 1 hour at room temperature. The plates were then emptied and washed 3 times with TBST. 100 µl of 3,3', 5,5'-Tetra methyl-benzidin (TMB) substrate (Sigma) was added to each well and the plates were incubated in the dark for 30 minute at room temperature in order to allow for the color reaction to proceed. The color reaction was stopped by adding 100 µl 1 N sulfuric acid to each well. The absorbance was read at a wavelength of 450 nm ($OD_{450}$) on an automatic Microplate reader. The $OD_{450}$ values, which corresponded to the amount of Trastuzumab in the blood sample tested, were then plotted. The resulting plot is shown in FIG. 15.

Results:

The crystalline Trastuzumab injected i.v. entered the bloodstreanm immediately (it had reached its approximate maximum serum level at the first time point=30 minutes) and maintained its serum concentration for approximately 480 minutes before the serum levels started to drop. See FIG. 15. The crystalline Trastuzumab that was injected s.c. took longer to enter the bloodstream (it reached its approximate maximum serum level in approximately 480 minutes) than the Trastuzumab administered i.v. However, the approximate maximum serum levels of the Trastuzumab administered s.c.

were maintained until at least the last time point=48 hours, indicating that Trastuzumab crystals administered s.c. may advantageously maintain and control high serum levels of the antibody over extended periods of time. See FIG. 15.

Example 62

Rituximab Animal Models

Rituximab may be used for the treatment of non-Hodgkins lymphoma [Bertolini, F., Fusetti, L., Mancuso, P., Gobbi, A., Corsini, C., Ferrucci, P. F., Blood, volume 96, pp. 282-87 (2000)].

Procedure of Tumor Formation in Nude Mice:

A model of high-grade human grade non-Hodgkins lymphoma was generated by injecting 6- to 8-week-old NOD/SCID mice intraperitoneal (i.p.) with $10 \times 10^6$ Raji cells (ATCC). The mice were evaluated for tumor growth every other day. Tumor volume was measured with calipers, and the formula, width×length ×0.52, was applied to approximate the volume of the spheroid tumors. The chimeric anti-CD20 monoclonal antibody Rituximab, in its crystalline form, as prepared in Example 21, at concentrations ranging from 25-75 mg/ml, was given intraperitoneal (i.p.) to mice on days 3, 5, and 7. Control mice received i.p. or subcutaneous (s.c.) injections of phosphate-buffered saline (PBS). Tumor-bearing mice were killed by carbon dioxide asphyxiation, and tumor engraftment was confirmed by histologic, immunohistochemistry (1HC), and flow cytometry (FC) studies.

Example 63

Infliximab Animal Models

Infliximab has been used in the treatment of arthritis [Kim, S. H., Evans, C. H., Kim, S., Oligino, T., Ghivizzani, S. C. and Robbins, P. D., Arthritis Res., vol. 2, pp. 293-302 (2000); Yoshino, S., The Journal of Immunology, vol. 160, pp. 3067-71 (1998); Malfait, A. M., Williams, R. O., Malik, A. S., Maini, R. N. and Feldmann, M., Arthritis Rheum., vol. 44, pp. 1215-24 (2001)].

Procedure of Tumor Formation in Nude Mice:

Male DBA/1 lacJ (H-2q) mice, aged 7-8 weeks, were purchased from The Jackson Laboratory (Bar Harbor, Me., USA). The mice were immunized intradermally (i.d.) at the base of tail with 100 μg of bovine type II collagen. On day 21 after immunization, the mice received a booster injection (i.d.) of 100 μg type II collagen in Freund's incomplete adjuvant. For the synchronous onset of arthritis, 40 μg of lipopolysaccharide (Sigma, St Louis, Mo., USA) was injected i.p. on day 28.

At the onset of clinical arthritis, mice were treated for 4 weeks with anti-tumor necrosis factor (anti-TNF; Infliximab). Two milligrams of Infliximab crystals, as prepared in Example 37, were dissolved in 0.5 ml of PBS and injected i.p. daily. For treatment controls, 0.5 ml of PBS only and 0.5 ml of PBS containing 2 mg of nonspecific IgG were given to mice. After 4 weeks of treatment, mice were killed and hind paws were assessed histologically for joint damage.

Example 64

Stability of Rituximab in the Crystalline Form

Assay 1:

A 0.35 ml aliquot of Rituximab (at 10 mg/ml) crystal slurry, as prepared in Example 21, was stored in mother liquor at room temperature. 5 ml aliquots were removed at different time points over a one-month period. The integrity of the antibody was then analyzed on a non-reducing 4-20% Tris-glycine gradient gel. A single protein band was observed on the gel after Coomassie blue stain.

Assay 2:

A 100 mg/ml aliquot of Rituximab crystal slurry, as prepared in Example 21, was prepared by centrifuging 1.1 ml of crystal slurry and pellet was resuspended in 50 ml buffer containing 150 mM Sodium chloride, 25 mM sodium citrate, 0.09% Tween®80 (Sigma-Aldrich), pH 6.5. The suspended slurry was then stored at room temperature for a month before being analyzed on a non-reducing 4-20% Tris-glycine gradient gel. A single protein band was observed on the gel. (FIG. 12).

Example 65

Stability of Crystalline and Native (Soluble) Trastuzumab in the Presence of Organic Solvents Crystalline Trastuzumab:

Trastuzumab was crystallized as described in Example 31. A 50 μl aliquot of a slurry of Trastuzumab crystals (with a protein concentration of 22 mg/ml) was centrifuged in order to remove the mother liquor. The supernatant (mother liquor) was discarded. The Trastuzumab crystals were resuspended in 200 μl of acetone. The crystal/acetone mixture was incubated for 3 hours at 4° C. The acetone was removed by centrifugation and the Trastuzumab crystals were dissolved in 100 al of a solution containing 50 mM Tris, pH 7.0, 100 mM sodium chloride. The dissolved (soluble) Trastuzumab was then analyzed by Size-exclusion chromatography on HPLC (SEC-HPLC), using a Phenomenex 2000 SEC column, a buffer consisting of 50 mM Tris, pH 7.0 and 100 mM Sodium chloride, and a flow rate of 0.5 ml/minute.

Native Trastuzumab:

A 50 μl aliquot of soluble Trastuzumab (as supplied by manufacturer) at 22 mg/ml was added to 200 μl acetone. The crystal/acetone mixture was incubated for 20 minutes at 4° C. The acetone was removed by centrifugation and the soluble Trastuzumab was analyzed by SEC-HPLC, using a Phenomenex 2000 SEC column, a buffer consisting of 50 mM Tris, pH 7.0 and 100 mM Sodium chloride, and a flow rate of 0.5 ml/minute.

Results:

The dissolved Trastuzumab remained whole and maintained its native structure (FIG. 13), while the native/soluble Trastuzumab precipitated after the acetone treatment (FIG. 14), demonstrating a loss of the structural integrity of the native Trastuzumab.

This example demonstrates the increased stability of Trastuzumab in the crystalline state according to this invention, as compared with the stability of the native Trastuzumab antibody.

As demonstrated herein, crystallization of monoclonal antibodies including, inter alia, Trastuzumab, results in increased stability and the preservation of the structural integrity of the antibodies. Stability in organic solvents is very useful when performing controlled dissolutions using various polymers, e.g., polylactic-co-glycolyic acid ("PLGA"), for generating PLGA-encapsulated microspheres. Such processes cannot be performed if the antibodies or antibody fragments to be encapsulated become denatured in organic solvents.

Similar results have been obtained when Trastuzumab was exposed to other organic solvents, such as acetonitrile, ethanol, isopropyl alcohol (IPA) and 2-methyl-2,4-pentanediol ("MPD").

Example 66

Stability of Formulated Crystalline and Native (Soluble) Trastuzumab Crystalline Trastuzumab:

Trastuzumab crystals were prepared as in Example 31.

50 µl of a slurry containing crystals of Trastuzumab (at 22 mg/ml) were centrifuged, and the supernatant was discarded. The Trastuzumab crystals were resuspended in either buffer no. 1 (5% PEG 3350, 25% ethanol, 0.1% Tween®80 (Sigma-Aldrich), 50 mM trehalose, 50 mM sodium phosphate, pH 7.6) or buffer no. 2 (25% PEG 3350, 5% alcohol (either ethanol or isopropanol), 0.1% Tween®80 (Sigma-Aldrich), 50 mM trehalose, 100 mM Tris, pH 8.0). The crystal/buffer mixture was incubated at 4° C. for 16 days, after which the buffer supernatant was removed by centrifugation, and the crystals were dissolved in 100 µl of 50 mM Tris, pH 7.0, 100 mM sodium chloride. The Trastuzumab was subsequently analyzed by SEC-HPLC (using a Phenomenex 2000 SEC column, a buffer consisting of 50 mM Tris, pH 7.0, 100 mM sodium chloride, and a flow rate of 0.5 ml/minute).

Native Trastuzumab:

50 µl of soluble Trastuzumab (as supplied by manufacturer) (at 22 mg/ml) was added to either buffer no. 1 or no. 2. The crystal/buffer mixture was incubated at 4° C. for 2 hours, after which the buffer supernatant was separated from the precipitate, and the precipitate was analyzed for the presence of native Trastuzumab by SEC-HPLC (using the same conditions as above).

Results:

The dissolved crystalline Trastuzumab remained whole and maintained its native structure after being incubated with buffer 1 or 2, while the native/soluble Trastuzumab precipitated after being incubated with buffer 1 or 2, demonstrating a loss of the structural integrity of the native (soluble) Trastuzumab.

Example 67

Formulations Using Sucrose Acetate Isobutyrate (SAIB)

Formulations that use sucrose acetate isobutyrate (SAIB) relate to a parenteral liquid non-polymeric drug delivery system. This system comprises an antibody crystal or antibody fragment crystal suspended in sucrose acetate isobutyrate (SAIB) and a "plasticizing" solvent, e.g., lanolin, mineral oil, ethanol, that is injected as a liquid [S. A. Sullivan, R. M. Gilley, J. W. Gibson and A. J. Tipton, Pharmaceutical Research, vol. 14, p. 291 (1997)]. Following injection, the viscosity of the solution increases. The resulting high viscosity matrix is adhesive, biodegradable and biocompatible. The antibody is released in a controlled manner from the matrix.

Trastuzumab Formulation Using Sucrose Acetate Isobutyrate (SAIB)

The SAIB formulation system outlined above was performed using the antibody Trastuzumab.

Method:

The mother liquor was removed from a 100 µl aliquot of a crystal slurry containing Trastuzumab crystals. Then, the crystals were washed with a solution of 90% SAIB in ethanol (ethanol acts as a plasticizer in this example). At various time increments, 10 µl aliquot were removed from the SAIB/ethanol solution and suspended in 100 µl of 50 mM Tris, pH 7.0, 100 mM Sodium chloride. After a 10 minute incubation at room temperature, the crystals were dissolved and the resulting material was analyzed on SEC-HPLC to determine the structural integrity of the Trastuzumab.

Results:

The monoclonal antibody remained stable under the above conditions. Therefore, the SAIB formulation was shown to be suitable for use as a vehicle to deliver the Trastuzumab antibody subcutaneously.

It will be appreciated by those of skill in the art that the SAIB formulation according to this invention may be used as a controlled-delivery system for any crystal or crystal formulations or compositions of antibodies or fragments thereof, according to this invention.

Example 68

Stability of Crystalline Rituximab

For crystallization, 100 ml of Rituximab in 9 mg/ml of sodium chloride, 7.35 mg/ml sodium citrate dihydrate, 0.7 mg/ml polysorbate 80, pH 6.5 was mixed with 200 ml of crystallization buffer containing 0.1 M Hepes, pH 7.7, 12% PEG 400, 1.17 M sodium sulfate. The tube was then seeded with Rituximab crystals obtained from a microbatch and supplemented with 10 ml of 1.5 M sodium sulfate before incubated at room temperature overnight. The stability of the crystals in ethanol or PEG or a combination of both was determined after taking 20 ml of above crystal slurry and separating the crystals by centrifugation. The crystals were then suspended in 200 ml of 25 mM Tris, pH 7.0, with or without the presence of 10% ethanol and 10% PEG 3350 at 37° C. Samples were taken at up to 24 hr for the presence of dissolved protein in the supernatant. The protein was determined by BioRad Protein Assay Kit I (BioRad Laboratories, Catalogue No. 500-0001).

Results:

The results indicate that the crystals were readily soluble in 25 mM Tris, pH 7.0, and 10% ethanol. The solution containing 10% PEG alone precipitated the protein without maintaining the crystallinity. However, a combination of both ethanol and PEG maintained crystallinity and did not dissolve the crystals over a period of 1500 min (FIG. 10). It is possible to use a combination of both ethanol and PEG formulation for the Rituximab crystals, since both of the reagents are pharmaceutically acceptable.

Example 69

Stability of Crystalline Trastuzumab

Trastuzumab was crystallized as described below. In brief, 200 ml of Trastuzumab (22 mg/ml in original formulation, as provided by the manufacturer) with equal volume of crystallization buffer containing 25% PEG 400, 5% PEG 8000, 10% propylene glycol, 100 mM Tris, pH 8.0, 0.1% Tween®80 (Sigma-Aldrich) and incubated overnight at room temperature. The tube was then seeded and supplemented with 20 ml propylene glycol. The stability of the crystals in ethanol or PEG or a combination of both was determined after taking 80 ml of above crystal slurry and separating the crystals by centrifugation. The crystals were then suspended in 400 ml of 25 mM Tris, pH 7.0 with or without the presence of 10% ethanol and 10% PEG 3350 at 37° C. Samples were taken at up to 140 hours for the presence of dissolved protein in the supernatant. The protein was determined by BioRad Protein Assay Kit I (BioRad Laboratories—Catalogue No. 500-0001).

Results:

The results indicate that the crystals were readily soluble in 25 mM Tris, pH 7.0 and 10% ethanol. The solution containing 10% PEG alone precipitated the protein without maintaining the crystallinity. However, a combination of both ethanol and PEG maintained crystallinity and did not dissolve the crystals over a period of 8400 minutes (FIG. 11). It is possible to use a combination of both ethanol and PEG formulation for the Trastuzumab crystals, since both of these reagents are pharmaceutically acceptable.

Example 70

Preparation of Whole Antibody Crystals Using Polyethylene Oxide (PEO) as Excipient In order to enhance the stability of whole antibody crystals prepared according to this invention during drying and storage, the crystals may be formulated with excipients. Whole antibody crystals according to this invention may be formulated using 0.1% polyethylene oxide in water as follows. The crystals are separated from the mother liquor by centrifugation at 1000 rpm in a Beckman GS-6R bench top centrifuge equipped with swinging bucket rotor. Next, the crystals are suspended in 0.1% polyethylene oxide for 3 hrs (Sigma Chemical Co., St. Louis, Mo.) and then separated by centrifugation.

Example 71

Preparation of Whole Antibody Crystals Using Sucrose as Excipient

Whole antibody crystals according to this invention may be formulated in the slurry form in the presence of mother liquor before drying. Sucrose (Sigma Chemical Co., St. Louis, Mo.) is added to whole antibody crystals in mother liquor as an excipient. Sufficient sucrose is added to whole antibody crystals to reach a final sucrose concentration of 10% (w/v). The resulting suspension is then tumbled at room temperature for 3 hr. After treatment with sucrose, the crystals are separated from the liquid by centrifugation, as described in Example 70.

Example 72

Formulation of Whole Antibody Crystals Using Trehalose as Excipient

Whole antibody crystals according to this invention may be formulated as in Example 71, by adding trehalose instead of sucrose, (Sigma Chemical Co., St. Louis, Mo.), to a final concentration of 10% (w/v) in mother liquor. The resulting suspension is then tumbled at room temperature for 3 hr and the crystals are separated from the liquid by centrifugation, as described in Example 70.

Example 73

Formulation of Whole Antibody Crystals Using Methoxypolyethylene Glycol (MOPEG) as Excipient Whole antibody crystals are formulated as in Example 71, by adding methoxypolyethylene glycol (Sigma Chemical Co., St. Louis, Mo.), instead of sucrose, to a final concentration of 10% (w/v) in mother liquor and separating after 3 hrs by centrifugation, as in Example 70.

Example 74

Methods of Drying Crystal Formulations

Method 1. $N_2$ Gas Drying at Room Temperature

Crystals as prepared in one of Examples 1-3 are separated from the mother liquor containing excipient by centrifugation at 1000 rpm in a Beckman GS-6R bench top centrifuge equipped with swinging bucket rotor in a 50 ml Fisher brand disposable centrifuge tube (Polypropylene). The crystals are then dried by passing a stream of nitrogen at approximately 10 psi pressure into the tube overnight.

Method 2. Vacuum Oven Drying

Crystals, as prepared in one of Examples 1-3, are first separated from the mother liquor/excipient solution using centrifugation at 1000 rpm in a Beckman GS-6R bench top centrifuge equipped with swinging bucket rotor in a 50 ml Fisher brand Disposable polypropylene centrifuge tube. The wet crystals are then placed in a vacuum oven at 25 in Hg (VWR Scientific Products) at room temperature and dried for at least 12 hours.

Method 3. Lyophilization

Crystals, as prepared in one of Examples 1-3, are first separated from the mother liquor/excipient solution using centrifugation at 1000 rpm in a Beckman GS-6R bench top centrifuge equipped with swinging bucket rotor in a 50 ml Fisher brand Disposable polypropylene centrifuge tube. The wet crystals are then freeze dried using a Virtis Lyophilizer Model 24 in semi-stoppered vials. The shelf temperature is slowly reduced to −40° C. during the freezing step. This temperature is then held for 16 hrs. Secondary drying may then be then carried out for another 8 hrs.

Method 4. Organic Solvent and Air Drying

Crystals, as prepared in one of Examples 1-3, are first separated from the mother liquor/excipient solution using centrifugation at 1000 rpm in a Beckman GS-6R bench top centrifuge equipped with swinging bucket rotor in a 50 ml Fisher brand Disposable polypropylene centrifuge tube. The crystals are then suspended in an organic solvent like ethanol or isopropanol or ethyl acetate or other suitable solvents, and centrifuged. The supernatant is then decanted and air dried at room temperature in the fume hood for two days.

Method 5. Air Drying at Room Temperature

Crystals, as prepared in one of Examples 1-3, are separated from the mother liquor containing excipient by centrifugation at 1000 rpm in a Beckman GS-6R bench top centrifuge equipped with swinging bucket rotor in a 50 ml Fisher brand Disposable centrifuge tube (Polypropylene). Subsequently, the crystals are then allowed to air dry in the fume hood for two days.

Method 6. Spray Drying

Crystals, as prepared in one of Examples 1-3, are spray dried using a Buchi Mini Spray Dryer Model B-191. The slurry of crystals at a concentration of 30 to 50 mg/ml is used for spray drying.

Example 75

Crosslinking of Antibody or Antibody Fragment Crystals and Formulations or Compositions Thereof Crosslinking of crystals of a whole antibody, or crystals of an antibody fragment is carried out by incubating the crystal at a pH, such that the crosslinker is highly active and the crystalline nature of the antibody is preserved. Crosslinking is carried out either at ambient temperature or at 4° C. with tumbling or stirring. After 24 hrs, the slurry is centrifuged at 3000 rpm and the supernatant is discarded. The excess (or un-reacted) crosslinker is inactivated with an appropriate buffer salt like Tris or glycine. The pellet is then washed with the mother liquor or appropriate pharmaceutically-acceptable buffer to remove the excess (or un-reacted) crosslinker. The crosslinking conditions may change depending on the type of crosslinker used but the ultimate goal is to maintain the crystalline state of the antibody under the conditions used.

It will be understood that antibody or antibody fragment crystals may be crosslinked using any suitable crosslinking reagent including, inter alia, Dimethyl 3,3'-dithiobispropionimidate.HCl (DTBP), Dithiobis (succinimidylpropionate) (DSP), Bis maleimido-hexane (BMH), Bis[Sulfosuccinimidyl]suberate (BS), 1,5-Difluoro-2,4-dinitrobenzene (DFDNB), Dimethylsuberimidate.2HCl (DMS), Disuccinimidyl glutarate (DSG), Disulfosuccinimidyl tartarate (Sulfo-DST), 1-Ethyl-3-[3-Dimethylaminopropyl]carbodiimide hydrochloride (EDC), Ethylene glycolbis[sulfosuccinimidylsuccinate] (Sulfo-EGS), N-[g-maleimidobutyryloxy] succinimide ester (GMBS), N-hydroxysulfosuccinimidyl-4-azidobenzoate (Sulfo-HSAB), Sulfosuccinimidyl-6-[a-methyl-a-(2-pyridyldithio)toluamido] hexanoate (Sulfo-LC—SMPT), Bis-[b-(4-azidosalicylamido) ethyl]disulfide (BASED) and glutaraldehyde (GA).

Example 76

Dissolution of Disulfide Bond-Containing Crosslinked Monoclonal Antibody Crystals A 200 mM solution of cysteine is prepared by dissolving 242 mg of cysteine in 10 ml of 10 mM Tris HCl buffer, pH 7, containing 10 mM calcium chloride and 20% MPD. A 200 ml aliquot of a slurry of crosslinked monoclonal antibody crystals prepared according to this invention is taken and centrifuged at 3000 rpm for 5 minutes and the supernatant is discarded. The pellet is suspended in 200 ml of cysteine-containing Tris buffer. Another 200 ml of monoclonal antibody crystals is taken and centrifuged at 3000 rpm for 5 minutes and the supernatant is discarded. The pellet is then suspended in 200 ml of Tris buffer without any cysteine. All samples are incubated at 37° C. for 1 hour and monitored for dissolution in 32 mM NaOH (direct visual and microscopic observation).

After incubation for 1 hour at 37° C., the DTBP sample is fully soluble in the presence of cysteine and insoluble in its absence. The DSP sample is barely soluble in the presence of cysteine and insoluble in its absence.

Example 77

Characterization of pH Solubility of Crosslinked Whole Antibody Crystals at 37° C.

The solubility of various monoclonal antibody crystals prepared and crosslinked according to this invention with Dimethyl 3,3'-dithiobispropionimidate.HCl (DTBP), Dithiobis (succinimidylpropionate) (DSP), Bis maleimido hexane (BMH), Bis[Sulfosuccinimidyl]suberate (BS), 1,5-Difluoro-2,4-dinitrobenzene (DFDNB), Dimethylsuberimidate.2HCl (DMS), Disuccinimidyl glutarate (DSG), Disulfosuccinimidyl tartarate (Sulfo-DST), 1-Ethyl-3-[3-Dimethylaminopropyl]carbodiimide hydrochloride (EDC), Ethylene glycolbis [sulfosuccinimidylsuccinate] (Sulfo-EGS), N-[g-maleimidobutyryloxy]succinimide ester (GMBS), N-hydroxysulfosuccinimidyl-4-azidobenzoate (Sulfo-HSAB), Sulfosuccinimidyl-6-[a-methyl-a-(2-pyridyldithio) toluamido] hexanoate (Sulfo-LC—SMPT), Bis-[b-(4-azidosalicylamido) ethyl]disulfide (BASED) and glutaraldehyde (GA) may be assayed.

In 1.5 ml Eppendorf tubes, samples of uncrosslinked monoclonal antibody crystals and crosslinked monoclonal antibody crystal slurry, equal to 2.8 mg enzyme, may be microfuged at 3000 rpm for 5 minutes until the supernatant liquid is removed. Two pHs are tested: a) pH 7.4 and b) pH 2.0.

For pH 7.4, a 200 ml aliquot of PBS buffer (0.01 M phosphate, 0.0027 M potassium chloride, 0.137 M sodium chloride, pH 7.4) is added to each sample, bringing the concentration of monoclonal antibody to 14 mg/ml. The samples may then incubated at 37° C. for 24 hours.

For pH 2.0, a 200 ml aliquot of glycine/HCl buffer pH 2.0 is added to each sample, bringing the concentration of monoclonal antibody to 14 mg/ml. The samples are incubated at 37° C. for 5 hours. Initially, the samples are treated with 10 mM glycine/HCl buffer, pH 2.0 containing 10 mM calcium chloride and 20% MPD overnight at 25° C. with tumbling; then proceeding with glycine/HCl buffer alone.

Samples may be studied for dissolution by centrifuging the samples at 14,000 rpm for 5 minutes after 5 hours and 24 hours. After centrifugation, the supernatant is passed through a 0.22 mm filter. The protein (antibody) content of the supernatant is then estimated then by removing 2 μl of the aliquot and placing it in 798 ml of deionized water. A 200 μl aliquot of Bio-Rad Protein assay reagent is added to this sample and is incubated at ambient temperature for 5 minutes and measured at 595 nm wavelength (Bio-Rad micro protein assay by Bradford's method). As a standard, 0-20 μg bovine IgG (Sigma) is used.

While we have described a number of embodiments of this invention, it is apparent that our basic examples may be altered to provide other embodiments which utilize the products and processes of this invention. Therefore, it will be appreciated that the scope of this invention is to be defined by the appended claims rather than by the specific embodiments which have been represented by way of example.

We claim:

1. A crystal of infliximab, wherein the crystal comprises infliximab, ethoxyethanol, lithium sulfate, and Tris buffer.

2. The crystal of claim 1, wherein the pH of the Tris buffer is 8.6.

3. A method of crystallizing infliximab, the method comprising:
combining infliximab, ethoxyethanol, lithium sulfate, and Tris buffer, thereby forming a crystallization solution; and
incubating the crystallization solution, thereby crystallizing infliximab.

4. The method of claim 3, wherein the method is performed at room temperature.

5. The method of claim 3, wherein the method is performed at pH 8.6.

6. The method of claim 3, wherein the concentration of infliximab in the crystallization solution is $$\frac{2.5}{0.15} mg/ml.$$

7. The method of claim 3, wherein the percentage of ethoxyethanol in the crystallization solution is $$\frac{3500}{150}\%.$$

8. The method of claim 3, wherein the concentration of lithium sulfate in the crystallization solution is $$\frac{20}{150}M.$$

9. The method of claim 3, wherein the concentration of Tris buffer in the crystallization solution is $$\frac{10}{150}M.$$

10. The method of claim 3, wherein the concentration of infliximab in the crystallization solution is $$\frac{2.5}{0.15} mg/ml,$$

the percentage of ethoxyethanol in the crystallization solution is $$\frac{3500}{150}\%,$$

the concentration of lithium sulfate in the crystallization solution is $$\frac{20}{150}M,$$

and the concentration of Tris buffer in the crystallization solution is $$\frac{10}{150}M.$$

11. A crystal of infliximab, wherein the crystal comprises infliximab, PEG-400, lithium sulfate, and Tris buffer.

12. The crystal of claim 11, wherein the pH of the Tris buffer is 8.5.

13. A method of crystallizing infliximab, the method comprising:

combining infliximab, PEG-400, lithium sulfate, and Tris buffer, thereby forming a crystallization solution; and incubating the crystallization solution, thereby crystallizing infliximab.

14. The method of claim 13, wherein the method is performed at room temperature.

15. The method of claim 13, wherein the method is performed at pH 8.5.

16. The method of claim 13, wherein the concentration of infliximab in the crystallization solution is $$\frac{2.5}{0.15} \text{ mg/ml.}$$

17. The method of claim 13, wherein the percentage of PEG-400 in the crystallization solution is $$\frac{4000}{150}\%.$$

18. The method of claim 13, wherein the concentration of lithium sulfate in the crystallization solution is $$\frac{20}{150} M.$$

19. The method of claim 13, wherein the concentration of Tris buffer in the crystallization solution is $$\frac{10}{150} M.$$

20. The method of claim 13, wherein the concentration of infliximab in the crystallization solution is $$\frac{2.5}{0.15} \text{ mg/ml,}$$

the percentage of PEG-400 in the crystallization solution is $$\frac{4000}{150}\%,$$

the concentration of lithium sulfate in the crystallization solution is $$\frac{20}{150} M,$$

and the concentration of Tris buffer in the crystallization solution is $$\frac{10}{150} M.$$

21. A crystal of infliximab, wherein the crystal comprises infliximab, polyethylene glycol monomethyl ether 550 (PEG MME 550), calcium chloride, and Tris HCl buffer.

22. The crystal of claim 21, wherein the pH of the Tris HCl buffer is 7.0.

23. A method of crystallizing infliximab, the method comprising:

combining infliximab, PEG MME 550, calcium chloride, and Tris HCl buffer, thereby forming a crystallization solution; and incubating the crystallization solution, thereby crystallizing infliximab.

24. The method of claim 23, wherein the method is performed at room temperature.

25. The method of claim 23, wherein the pH of the Tris HCl buffer is 7.0.

26. The method of claim 23, wherein the concentration of infliximab in the crystallization solution is $$\frac{1.25}{0.033} \text{ mg/ml.}$$

27. The method of claim 23, wherein the percentage of PEG MME 550 in the crystallization solution is $$\frac{500}{33}\%.$$

28. The method of claim 23, wherein the concentration of calcium chloride in the crystallization solution is $$\frac{3}{33} M.$$

29. The method of claim 23, wherein the concentration of Tris HCl buffer in the crystallization solution is $$\frac{2.5}{33} M.$$

30. The method of claim 23, wherein the concentration of infliximab in the crystallization solution is $$\frac{1.25}{0.033} \text{ mg/ml,}$$

the percentage of PEG MME 550 in the crystallization solution is $$\frac{500}{33}\%,$$

the concentration of calcium chloride in the crystallization solution is $$\frac{3}{33} \text{ M,}$$

and the concentration of Tris HCl buffer in the crystallization solution is $$\frac{2.5}{33} \text{ M.}$$

31. A crystal of infliximab, wherein the crystal comprises infliximab, PEG 300, Tris buffer, PEG 8000, and glycerol.

32. The crystal of claim 31, wherein the pH of the Tris buffer is 8.5.

33. A method of crystallizing infliximab, the method comprising:
   combining infliximab, PEG 300, Tris buffer, PEG 8000, and glycerol, thereby forming a crystallization solution; and
   incubating the crystallization solution, thereby crystallizing infliximab.

34. The method of claim 33, wherein the method is performed at room temperature.

35. The method of claim 33, wherein the pH is 8.5.

36. The method of claim 33, wherein the concentration of infliximab in the crystallization solution is $$\frac{0.5}{0.075} \text{ mg/ml.}$$

37. The method of claim 33, wherein the percentage of PEG 300 in the crystallization solution is $$\frac{1000}{75}\%.$$

38. The method of claim 33, wherein the concentration of Tris buffer in the crystallization solution is $$\frac{5}{75} \text{ M.}$$

39. The method of claim 33, wherein the percentage of PEG 8000 in the crystallization solution is $$\frac{250}{75}\%.$$

40. The method of claim 33, wherein the percentage of glycerol in the crystallization solution is $$\frac{500}{75}\%.$$

41. The method of claim 33, wherein the concentration of infliximab in the crystallization solution is $$\frac{0.5}{0.075} \text{ mg/ml,}$$

the percentage of PEG 300 in the crystallization solution is $$\frac{1000}{75}\%,$$

the concentration of Tris buffer in the crystallization solution is $$\frac{5}{75} \text{ M,}$$

the percentage of PEG 8000 in the crystallization solution is $$\frac{250}{75}\%,$$

and the percentage of glycerol in the crystallization solution is $$\frac{500}{75}\%.$$

* * * * *

SEQUENCE LISTING

<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Glu Val Gln Leu Val Gly Ser
 1               5

```
<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Ile Gln Met Thr Gln Ser
 1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Val Leu Ser Gln Ser
 1               5
```